(12) United States Patent
Bilodeau et al.

(10) Patent No.: US 7,569,589 B2
(45) Date of Patent: Aug. 4, 2009

(54) POTASSIUM CHANNEL INHIBITORS

(75) Inventors: Mark T. Bilodeau, Lansdale, PA (US); Christopher J. Dinsmore, Newton, MA (US); Jeffrey M. Bergman, Sellersville, PA (US); B. Wesley Trotter, Glenside, PA (US); Lou Anne Neilson, Sellersville, PA (US); Zhicai Wu, Quakertown, PA (US); Peter Manley, Harleysville, PA (US); John Hartnett, Conshohocken, PA (US)

(73) Assignee: Merck & Co., Inc., Rahway, NJ (US)

( * ) Notice: Subject to any disclaimer, the term of this patent is extended or adjusted under 35 U.S.C. 154(b) by 592 days.

(21) Appl. No.: 11/188,466

(22) Filed: Jul. 25, 2005

(65) Prior Publication Data

US 2006/0030595 A1 Feb. 9, 2006

Related U.S. Application Data

(60) Provisional application No. 60/592,242, filed on Jul. 29, 2004, provisional application No. 60/592,181, filed on Jul. 29, 2004.

(51) Int. Cl.
*C07D 403/14* (2006.01)
*A61K 31/44* (2006.01)

(52) U.S. Cl. ...................... 514/333; 546/256

(58) Field of Classification Search ........................ None
See application file for complete search history.

(56) References Cited

FOREIGN PATENT DOCUMENTS

| WO | WO 00/25770 | 5/2000 |
|---|---|---|
| WO | WO 00/25774 | 5/2000 |
| WO | WO 01/00573 | 1/2001 |
| WO | WO 01/25189 | 4/2001 |
| WO | WO 01/51519 | 7/2001 |
| WO | WO 02/24655 | 3/2002 |
| WO | WO 02/44137 | 6/2002 |
| WO | WO 02/46162 | 6/2002 |
| WO | WO 02/48131 | 6/2002 |
| WO | WO 02/100825 | 12/2002 |
| WO | WO 03/059873 | 7/2003 |
| WO | WO 2004/082716 | 9/2004 |
| WO | WO 2004/083157 | 9/2004 |
| WO | WO 2004/098525 | 11/2004 |
| WO | WO 2005/030129 | 4/2005 |
| WO | WO 2005/030130 | 4/2005 |
| WO | WO 2005/030217 | 4/2005 |
| WO | WO 2005/030726 | 4/2005 |
| WO | WO 2005/030727 | 4/2005 |
| WO | WO 2005/030729 | 4/2005 |
| WO | WO 2005/030791 | 4/2005 |
| WO | WO 2005/030792 | 4/2005 |

OTHER PUBLICATIONS

Brendel, J. "Blockers of the Kv1.5 channel for the treatment of atrial arrhythmias". Cardiovascular, Renal, Endocrine & Metabolic 2002, pp. 1589-1598.

R. Haberi, et al., Monatshefte Fuer Chemie, vol. 88, pp. 47-51 (1957) Database Accession No. 1957:71471.

W. Czuba, Bulletin DE L'Academie Polonaise Des Sciences, vol. 8, No. 6, pp. 281-284, 1960.

G.N. Walker, Organic Chemistry, vol. 27, pp. 2966-2967, 1962, Database Accession No. 1025723/BRN.

K.K. Chiu, et al., Chemical Society, Section C, Organic Chemistry, vol. 19, pp. 2758-2761, 1969.

K.K. Chiu, et al., Spectrochimica Acta Part A: Molecular and Biomolecular Spectroscopy, vol. 29, No. 11, pp. 1947-1952 (1973).

E.V. Brown, et al.,, "Pinacol Rearrangement of Quinoline Analogs of Benzopinacol and Evidence for Rearrangement . . . ", Journal of Heterocyclic Chemistry, vol. 6, No. 4, pp. 567-570 (1969).

E.F. Pratt, et al., "Oxidation by Solids. II. The Preparation of Either Tetraarylethanes of Diaryl Ketones by the Oxidation of . . . ", Journal of Organic Chemistry, vol. 28, pp. 638-642 (1963).

M.R. Kegelman, et al., "The Pinacol Rearrangement in the Heterocyclic Series. I. Pyridine Analogs of Benzopinacol", Journal of the American Chemical Society, vol. 75, pp. 4649-4651 (1953).

N.D. Heindel, et al., Tetrahedron Letters, No. 32, pp. 3579-3582 (1968).

V.J. Traynelis, et al., "Reactions of 4-Alkylpyridine N-Oxide With Dimethyl Sulfoxide", Tetrahedron Letters, No. 42, pp. 3619-3622 (1960).

S. Banks, et al., "Substituent Effect on the Electrochemical Oxidation of Arylmethyl Anions. 4. Effect of Pyridine Rings", Journal of Organic Chemistry, vol. 52, pp. 5105-5111 (1987).

(Continued)

*Primary Examiner*—Zinna N Davis
(74) *Attorney, Agent, or Firm*—Richard S. Parr; Mark R. Daniel

(57) ABSTRACT

The present invention relates to compounds having the structure

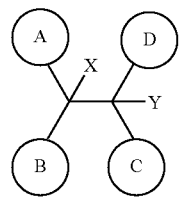

useful as potassium channel inhibitors to treat cardiac arrhythmias, and the like.

13 Claims, No Drawings

OTHER PUBLICATIONS

J.J. Eisch, et al., "Coordination-Induced Reductive Elimination and Titanium(II) Carbenoid Transfer in Reactions of", Organometallics, vol. 22, pp. 24-26 (2003).

M. Abe, et al., "Oxidative Ring-Opening Reaction of Cyclopropanone Acetals with Carbonyl Compounds via Photoinduced Electron Transfer.", Journal of Organic Chemistry, vol. 60, pp. 3065-3073 (1965).

H.E. Zimmermann, et al., "Control of the Sterochemistru pf Kinetic Protonation: Intramolecular Proton Delivery", Journal of Organic Chemistry, vol. 64, pp. 6635-6645 (1999).

E.V. Brown, et al., "Photochemical Preparation and Rearrangement of Some Symmetrical Methoxypyridyl Phenyl Glycols (Pinacols)", Journal of Heterocyclic Chemistry, vol. 8, No. 6, pp. 967-973 (1971).

M.L. Black, et al., "2-(2-Pyridyl)-1,2-diarylalkanols as Hypocholesteremic Agents", Journal of Medicinal Chemistry, vol. 10, No. 4, pp. 565-575 (1967).

F.J. Villani, et al., "Hypocholesteremic Agents. I. Substituted Stilbazoles and Dihydrostilbazoles", Journal of Medicinal Chemistry, vol. 13, No. 3, pp. 359-366 (1970).

A. Richardson Jr. et al., "Triarylpyridylethanols and Triarylpyridylethylenes. Chemistry and Antifertility Effects", Journal of Medicinal Chemistry, vol. 18, No. 7, pp. 689-691 (1975).

D.M. D'Alessandro, et al., Journal of Chemistry, vol. 56, No. 7, pp. 657-664 (2003).

M.R. Kegelman, et al. "The Pinacol Rearrangement in the Heterocyclic Series. III. Numerical Migratory Aptitudes", Journal of the American Chemical Society, vol. 76, pp. 2711-2713 (1954).

Search Report ROC (Taiwan Patent Application No. 094125011). Date of Completion of Search: Apr. 1, 2009.

J.H. Burckhalter, et al. "2-(2-pyridyl0-1,2-Diarylalkanols as Hypocholesteremic Agents" Journal of Medicinal Chemistry, 1967. vol. 10, No. 4, pp. 565-575. The pertinent section is - The Abstract and the compounds 76-81 on p. 566.

POTASSIUM CHANNEL INHIBITORS

This application claims the benefit of U.S. Provisional Application No. 60/592,181 filed Jul. 29, 2004 and 60/592,242 filed Jul. 29, 2004.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like.

Arial fibrillation (AF) is the most common sustained cardiac arrhythmia in clinical practice and is likely to increase in prevalence with the aging of the population. While AF is rarely fatal, it can impair cardiac function and lead to complications such as the development of congestive heart failure, thromboembolism, or ventricular fibrillation.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation*, 102:2665-2670), but pose an unacceptable risk of potentially lethal ventricular proarrhythmia and thus may increase mortality (Pratt, C M, Moye, L A, *Am J. Cardiol.*, 65:20B-29B, 1990; Waldo et al, *Lancet*, 348:7-12, 1996; Torp-Pedersen et al, *Expert Opin. Invest. Drugs*, 9:2695-2704, 2000). These observations demonstrate a clear unmet medical need to develop safer and more efficacious drugs for the treatment of atrial arrhythmias. Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation*, 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs*, 9:2695-2704, 2000). However, these agents have the major liability of an enhanced risk of proarrhythmia at slow heart rates.

The ultrarapid delayed rectifier K+ current, $I_{Kur}$, has been observed specifically in human atrium and not in ventricle. The molecular correlate of $I_{Kur}$ in the human atrium is the potassium channel designated Kv1.5. $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic afterdepolarizations and acquired long QT syndrome observed during treatment with current Class III drugs. Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

The invention concerns compounds of formula I which antagonizes the Kv1.5 potassium channel:

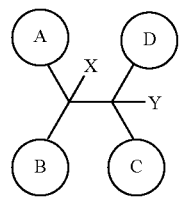

I

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention concerns compounds of formula I which antagonizes the Kv1.5 potassium channel:

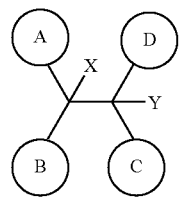

I wherein:
A, B and C are independently selected from the group consisting of:
  1) an aryl ring, and
  2) a heteroaryl ring, wherein the point of attachment to the heteroaryl ring is a carbon atom, and the heteroaryl ring is selected from the group consisting of:
     a) a 5-membered unsaturated monocyclic ring with 1, 2, 3, or 4 heteroatom ring atoms selected from the group consisting of N, O or S,
     b) a 6-membered unsaturated monocyclic ring with 1, 2, 3, or 4 heteroatom ring atoms selected from the group consisting of N, O or S, and
     c) an 8-, 9- or 10-membered unsaturated bicyclic ring with 1, 2, 3, or 4 heteroatom ring atoms selected from the group consisting of N, O or S, said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms; provided that at least one of substituents A, B and C is a heteroaryl ring;

D is selected from the group consisting of:
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S, and
3) a 4-6 membered saturated heterocyclic ring with 1, 2 or 3 heteroatom ring atoms selected from the group consisting of N, O and S, wherein the point of attachment to the heterocyclic ring is a carbon atom, said aryl, heteroaryl, saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

X and Y are independently selected from the group consisting of H, $OR^5$, $NR^5R^5$, F, CN, —NHS(O)$R^5$, $S(O)_{0-2}R^5$, $C(O)OR^5$, and $C(O)N(R^5)_2$;

$R^a$, in each instance in which it appears, is independently selected from the group consisting of
1) hydrogen,
2) $C_1$-$C_6$ alkyl,
3) halogen,
4) aryl,
5) heterocyclyl,
6) $C_3$-$C_{10}$ cycloalkyl, and
7) $OR^5$,
said alkyl, aryl, heterocyclyl and cycloalkyl is unsubstituted or substituted with at least one substituent selected from $R^6$;

$R^4$, in each instance in which it appears, is independently selected from the group consisting of
1) hydrogen,
2) halogen,
3) $NO_2$,
4) CN,
5) $CR^4$=$C(R^5)_2$,
6) C≡$CR^5$,
7) $(CR^a_2)_nOR^5$,
8) $(CR^a_2)_nN(R^5)_2$,
9) $(CR^a_2)_n C(O)R^5$,
10) $(CR^a_2)_nC(O)OR^5$,
11) $(CR^a_2)_nR^5$,
12) $(CR^a_2)_nS(O)_mR^5$,
13) $(CR^a_2)_nS(O)_mN(R^5)_2$,
14) $OS(O)_mR^5$,
15) $N(R^5)C(O)R^5$,
16) $N(R^5)S(O)_mR^5$,
17) $(CR^a_2)_nN(R^6)R^5$,
18) $(CR^a_2)_nN(R^5)(CR^a_2)_nC(O)N(R^5)_2$,
19) $(CR^a_2)_nN(R^5)(CR^a_2)_nC(O)OR^5$,
20) $N(R^5)(CR^a_2)_nR^5$,
21) $N(R^5)(CR^a_2)_nN(R^5)_2$,
22) $(CR^a_2)_nC(O)N(R^5)_2$,
23) $N_3$, and
22) =O;

$R^5$, in each instance in which it appears, is independently selected from the group consisting of
1) hydrogen,
2) unsubstituted or substituted $C_1$-$C_6$ alkyl,
3) unsubstituted or substituted $C_3$-$C_{10}$ cycloalkyl,
4) unsubstituted or substituted aryl,
5) unsubstituted or substituted heterocycle,
6) $CF_3$,
7) unsubstituted or substituted $C_2$-$C_6$ alkenyl, and
8) unsubstituted or substituted $C_2$-$C_6$ alkynyl,
or in the case where $R^5$ is attached to a nitrogen atom that is disubstituted with $R^5$, each $R^5$ is independently selected from $C_1$-$C_6$ alkyl, and the nitrogen atom together with each $R^5$ form a ring;

$R^6$, in each instance in which it appears, is independently selected from the group consisting of
1) hydrogen,
2) unsubstituted or substituted $C_1$-$C_6$ alkyl,
3) halogen,
4) $OR^5$,
5) $CF_3$,
6) unsubtituted or substituted aryl,
7) unsubstituted or substituted $C_3$-$C_{10}$ cycloalkyl,
8) unsubstituted or substituted heterocycle,
9) $S(O)_mN(R^5)_2$,
10) $C(O)OR^5$,
11) $C(O)R^5$,
12) CN,
13) $C(O)N(R^5)_2$,
14) $N(R^5)C(O)R^5$,
15) $N(R^5)C(O)OR^5$,
16) $N(R^5)C(O)N(R^5)_2$,
17) $OC(O)N(R^5)_2$,
18) $S(O)_mR^5$,
19) $OS(O)_mR^5$,
20) $NO_2$, and
21) $N(R^5)_2$;

m is independently 0, 1 or 2; and
n is independently 0, 1, 2, 3, 4, 5 or 6.

The phrase "provided that at least one of substituents A, B and C is a heteroaryl ring" means that the invention does not include compounds in which A, B, and C are simultaneously aryl. Compounds of the invention include those in which any one of A, B and C are a heteroaryl ring, those in which two of A, B and C are heteroaryl rings, and those in which all three of A, B and C are heteroaryl rings.

An embodiment of the invention is a compound wherein A is selected from the group consisting of:
1) an aryl ring, and
2) a heteroaryl ring, wherein the point of attachment to the heteroaryl ring is a carbon atom, wherein the heteroaryl ring is a 6-membered unsaturated monocyclic ring with 1, 2, 3, or 4 heteroatom ring atoms selected from the group consisting of N, O or S, said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

B is selected from the group consisting of:
1) an aryl ring, and
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S,
said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

C is selected from the group consisting of:
1) an aryl ring, and
2) a heteroaryl ring, wherein the point of attachment to the heteroaryl ring is a carbon atom, wherein the heteroaryl ring is a 6-membered unsaturated monocyclic ring with 1, 2, 3, or 4 heteroatom ring atoms selected from the group consisting of N, O or S,
said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

D is selected from the group consisting of:
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S, and
   b) a 6-membered unsaturated monocyclic ring with 1, 2, 3, or 4 heteroatom ring atoms selected from the group consisting of N, O or S, and
3) a 5-membered saturated heterocyclic ring with 1, 2 or 3 heteroatom ring atoms selected from the group consisting of N, O and S, wherein the point of attachment to the heterocyclic ring is a carbon atom,
said aryl, heteroaryl, saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms; and X and Y are independently selected from the group consisting of H, $OR^5$, and $—NHS(O)R^5$.

A preferred embodiment of the invention is a compound wherein

A is selected from the group consisting of:
1) an aryl ring, and
2) a heteroaryl ring, wherein the point of attachment to the heteroaryl ring is a carbon atom, wherein the heteroaryl ring is a 6-membered unsaturated monocyclic ring with 1 or 2 N ring atoms,
said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable N heteroaryl or heterocyclic ring atom is unsubstituted or substituted with oxo, said heteroaryl ring $R^4$ substitutions being on one or more heteroaryl ring carbon atoms;

B is selected from the group consisting of:
1) an aryl ring, and
2) a heteroaryl ring, wherein the point of attachment to the heteroaryl ring is a carbon atom, and the heteroaryl ring is selected from the group consisting of:
   a) a 5-membered unsaturated monocyclic ring with 1 or 2 N ring atoms and 0 or 1 O atoms, and
   b) a 6-membered unsaturated monocyclic ring with 1 or 2 N atoms,
said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable N heteroaryl or heterocyclic ring atom is unsubstituted or substituted with oxo, said heteroaryl ring $R^4$ substitutions being on one or more heteroaryl ring carbon atoms;

C is selected from the group consisting of:
1) an aryl ring, and
2) a heteroaryl ring, wherein the point of attachment to the heteroaryl ring is a carbon atom, wherein the heteroaryl ring is a 6-membered unsaturated monocyclic ring with 1 N atom,
said aryl and heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable N heteroaryl or heterocyclic ring atom is unsubstituted or substituted with oxo, said heteroaryl ring $R^4$ substitutions being on one or more heteroaryl ring carbon atoms; and D is selected from the group consisting of:
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 4 N ring atoms, and
   b) a 6-membered unsaturated monocyclic ring with 1 or 2 N ring atoms, and
3) a 5-membered saturated heterocyclic ring with 1 N ring atom, wherein the point of attachment to the heterocyclic ring is a carbon atom,
said aryl, heteroaryl, saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable N heteroaryl or heterocyclic ring atom is unsubstituted or substituted with oxo, said heteroaryl ring R⁴ substitutions being on one or more heteroaryl ring carbon atoms.

A more preferred embodiment of the invention is a compound wherein

X is selected from the group consisting of hydrogen and —OH;

Y is selected from the group consisting of hydrogen, —OH, and —NHS(O)C(CH$_3$)$_3$;

A is selected from the group consisting of

B is selected from the group consisting of

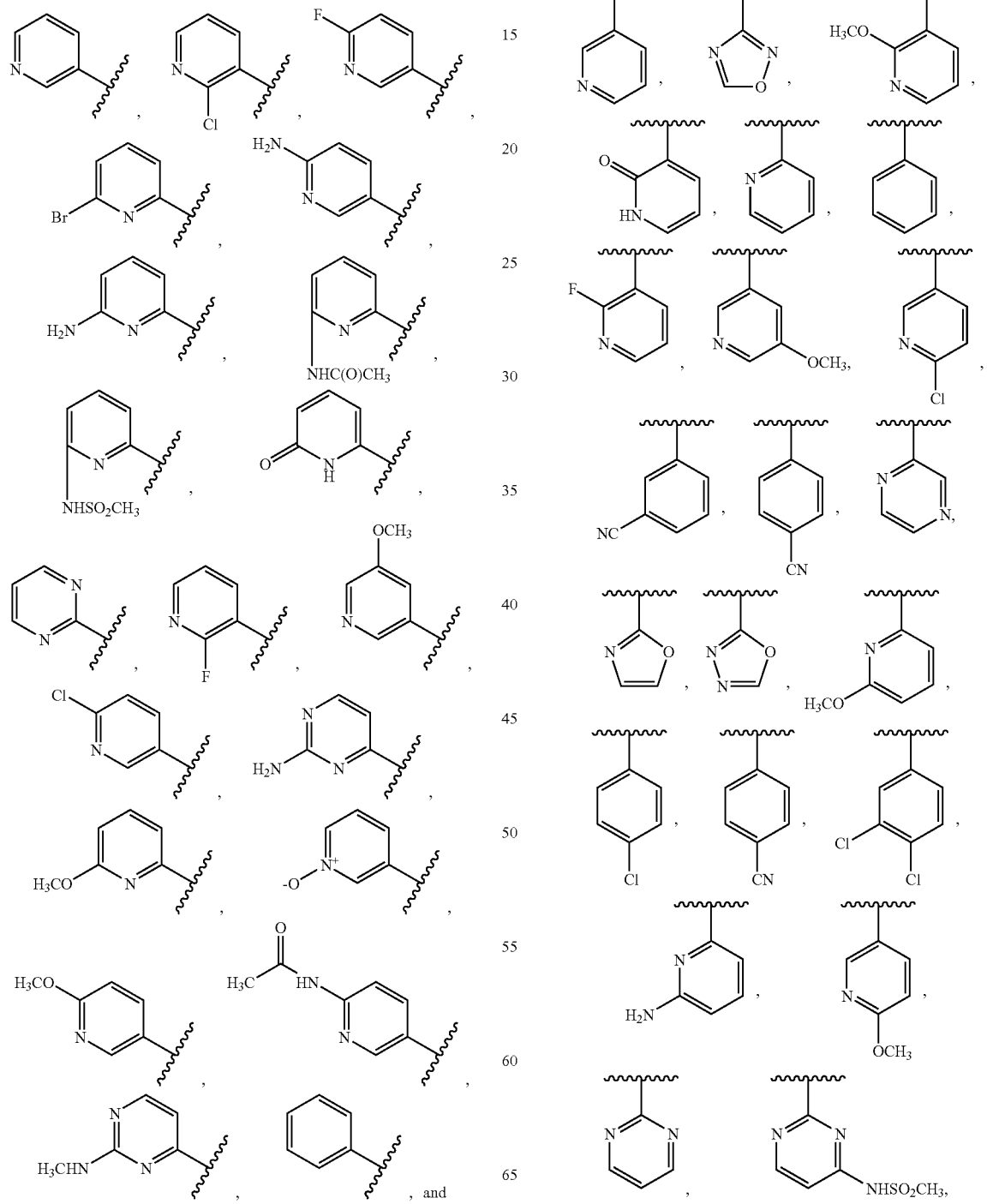

C is selected from the group consisting of
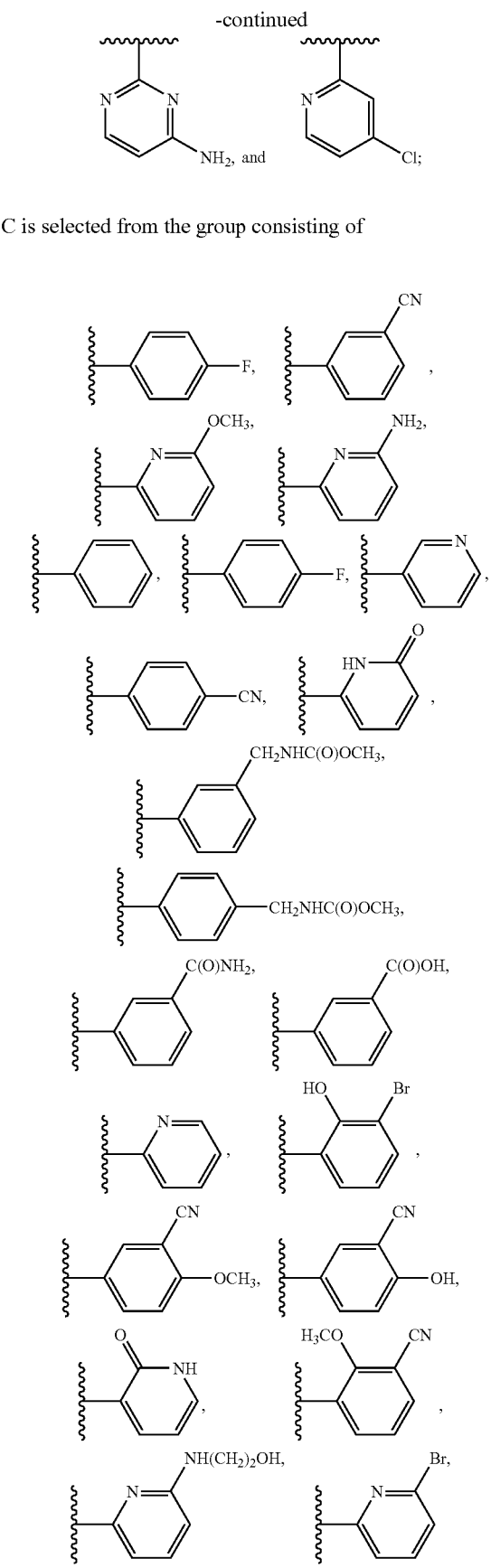
D is selected from the group consisting of

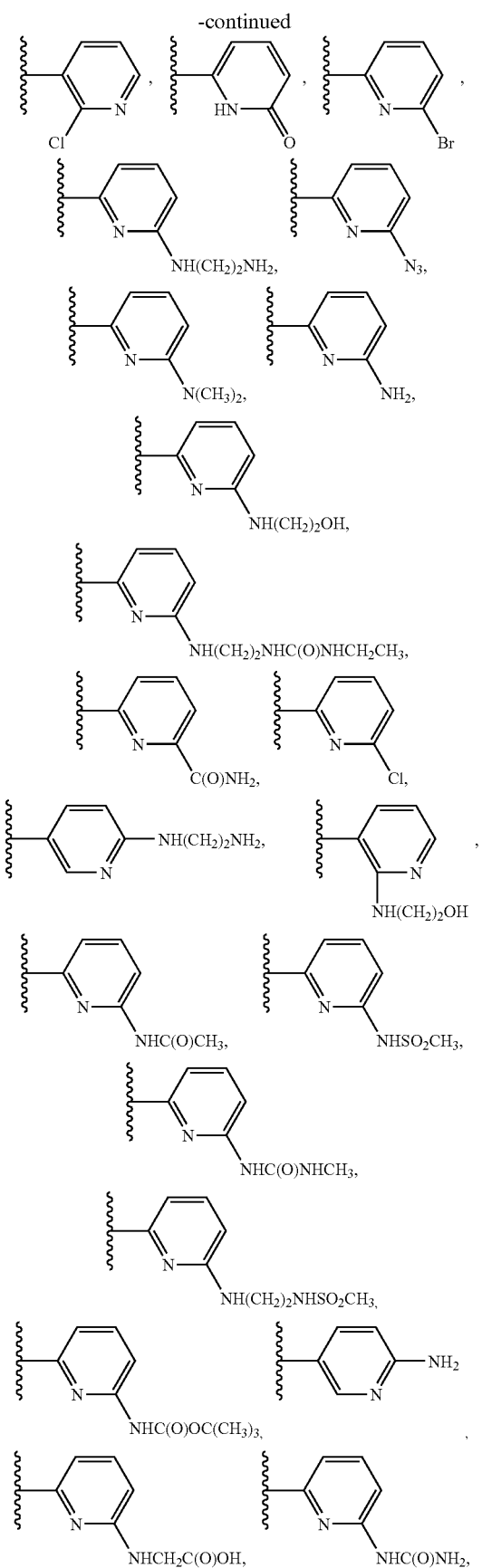
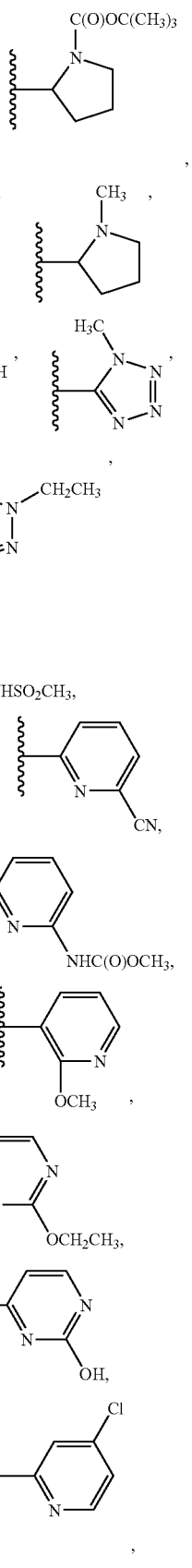

-continued
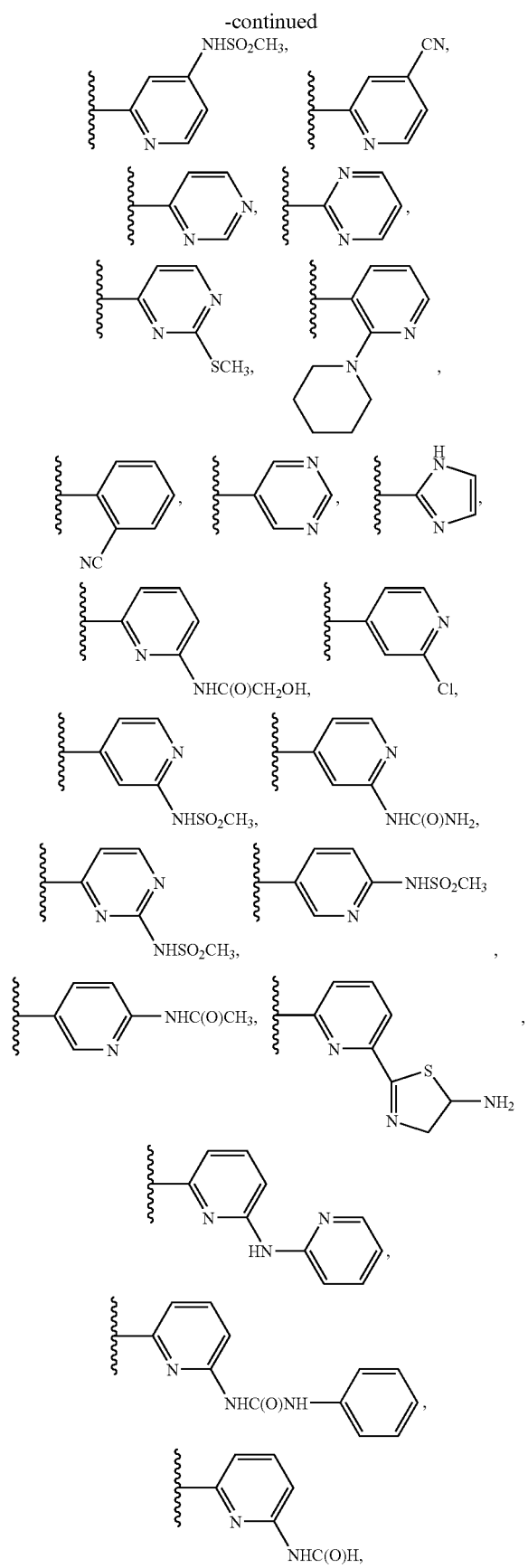
Another more preferred embodiment of the invention is a compound wherein
X is selected from the group consisting of hydrogen and —OH;
Y is selected from the group consisting of hydrogen, —OH, and —NHS(O)C(CH$_3$)$_3$;

A is selected from the group consisting of
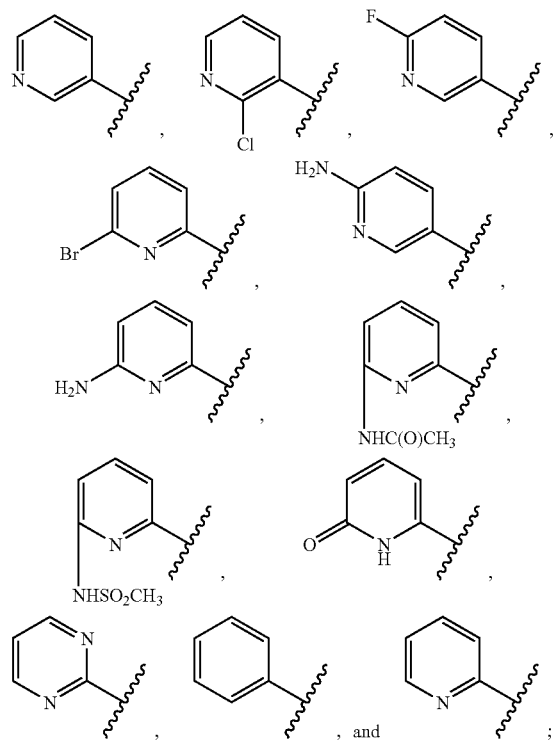
B is selected from the group consisting of
C is selected from the group consisting of
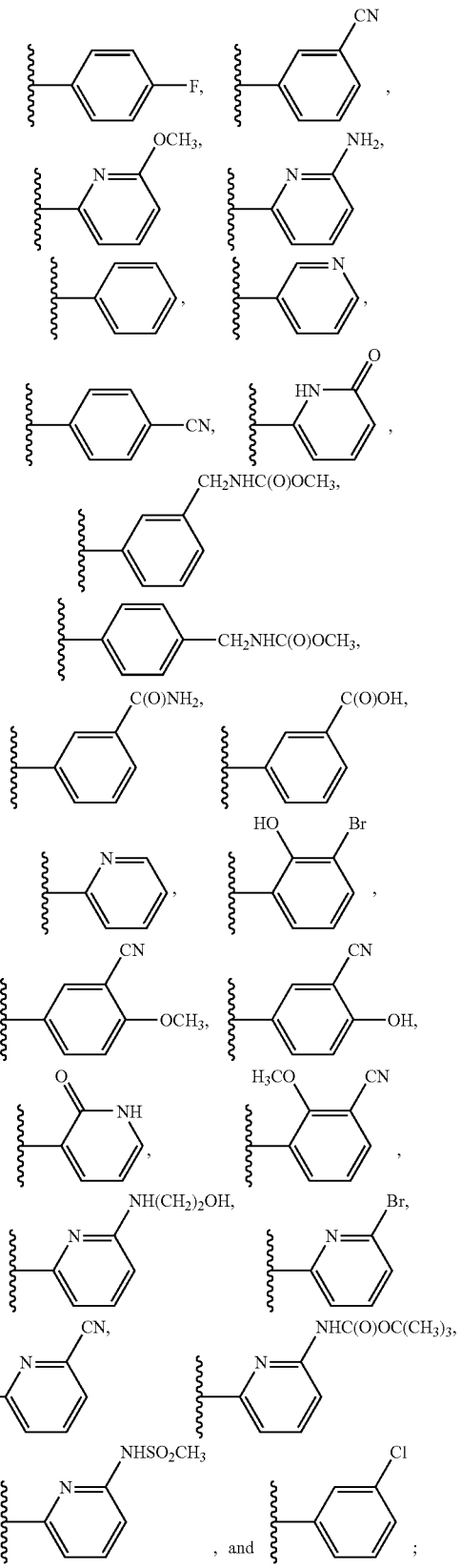

D is selected from the group consisting of
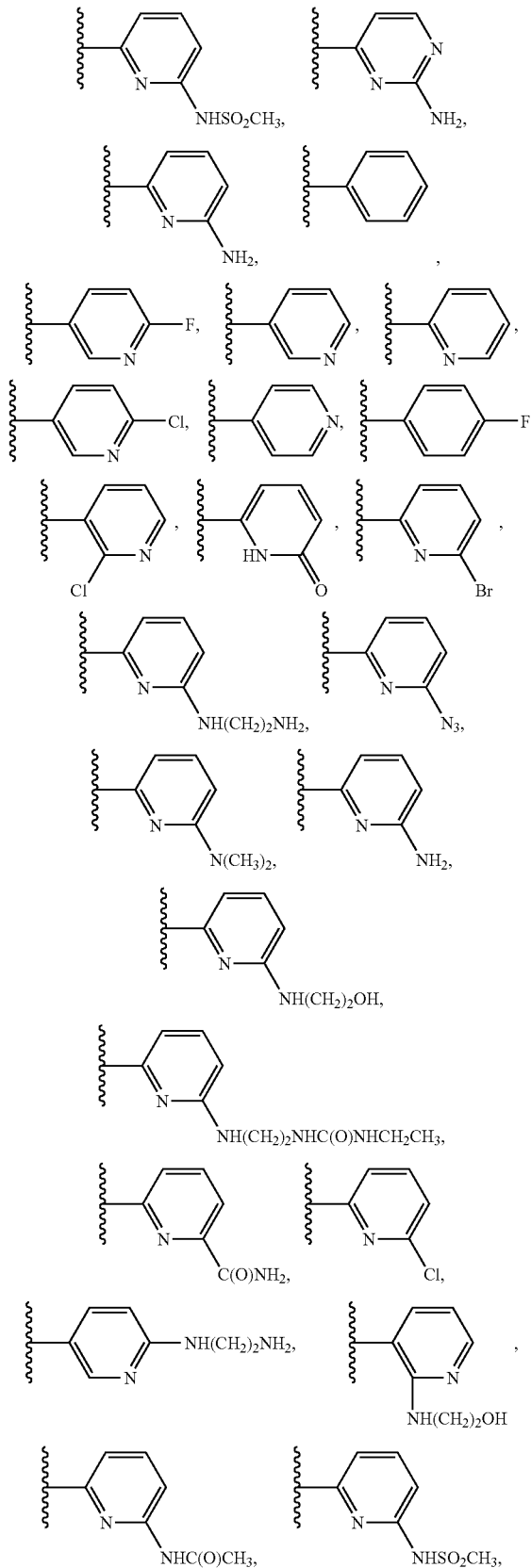
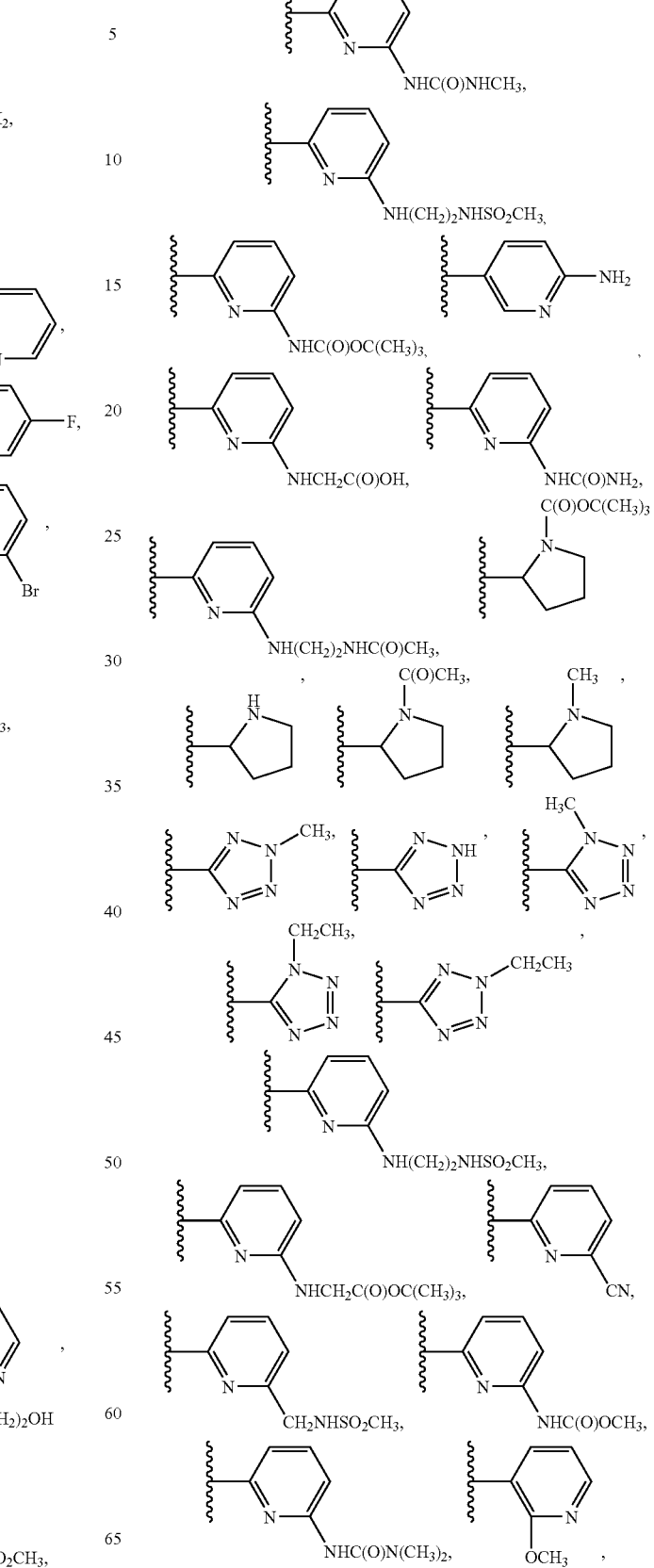

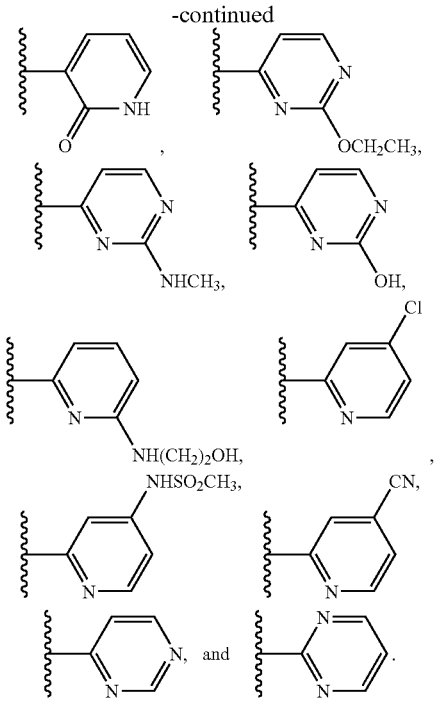

An example of a compound of the invention is a compound selected from the group consisting of
(R)-N-{6-[1-(4-fluorophenyl)-2,2-dipyridin-3-ylethyl]pyridin-2-yl}methanesulfonamide,
(S)-N-{6-[1-(4-fluorophenyl)-2,2-dipyridin-3-ylethyl]pyridin-2-yl}methanesulfonamide,
(R)-N-{6-[1-(3-cyanophenyl)-2,2-dipyridin-3-ylethyl]pyridin-2-yl}methanesulfonamide,
(S)-N-{6-[1-(3-cyanophenyl)-2,2-dipyridin-3-ylethyl]pyridin-2-yl}methanesulfonamide,
(R)-N-{6-[1-(6-methoxypyridin-2-yl)-2,2-dipyridin-3-ylethyl]pyridin-2-yl}methanesulfonamide,
(S)-N-{6-[1-(6-methoxypyridin-2-yl)-2,2-dipyridin-3-ylethyl]pyridin-2-yl}methanesulfonamide,
(R)-3-[1-(2-aminopyrimidin-4-yl)-2,2-dipyridin-3-ylethyl]benzonitrile,
(S)-3-[1-(2-aminopyrimidin-4-yl)-2,2-dipyridin-3-ylethyl]benzonitrile,
6-[1-(6-aminopyridin-2-yl)-2,2-dipyridin-3-ylethyl]pyridin-2-amine,
(±)-2-fluoro-5-[1-(4-fluorophenyl)-2,2-dipyridin-3-ylethyl]pyridine,
(±)-3-(1-pyridin-2-yl-2,2-dipyridin-3-ylethyl)benzonitrile,
(±)-4-(1-pyridin-2-yl-2,2-dipyridin-3-ylethyl)benzonitrile,
(±)-3-[1-(4-fluorophenyl)-2,2-dipyridin-3-ylethyl]pyridine,
(±)-2-[1-(4-fluorophenyl)-2,2-dipyridin-3-ylethyl]pyridine,
(±)-3-[2-(4-fluorophenyl)-1-pyridin-3-yl-2-pyridin-4-ylethyl]pyridine,
(±)-2-chloro-3-[2-(4-fluorophenyl)-2-pyridin-2-yl-1-pyridin-3-ylethyl]pyridine,
(±)-2-chloro-3-[2-(4-fluorophenyl)-2-pyridin-2-yl-1-pyridin-3-ylethyl]pyridine,
(±)-2-chloro-3-[1-(4-fluorophenyl)-2,2-dipyridin-3-ylethyl]pyridine,
(±)-2-fluoro-5-[2-(4-fluorophenyl)-2-pyridin-2-yl-1-pyridin-3-ylethyl]pyridine,
(±)-6-[1-(4-fluorophenyl)-2,2-dipyridin-3-ylethyl]-N,N-dimethylpyridin-2-amine,
(±)-6-[1-(4-fluorophenyl)-2,2-dipyridin-3-ylethyl]pyridin-2-amine,
(±)-2-({6-[1-(4-fluorophenyl)-2,2-dipyridin-3-ylethyl]pyridin-2-yl}amino)ethanol,
(±)-N-ethyl-N'-[2-({6-[1-(4-fluorophenyl)-2,2-dipyridin-3-ylethyl]pyridin-2-yl}amino)ethyl]urea,
(±)-6-[1-(4-fluorophenyl)-2,2-dipyridin-3-ylethyl]pyridine-2-carboxamide,
(±)-methyl 3-(1-pyridin-2-yl-2,2-dipyridin-3-ylethyl)benzylcarbamate,
(±)-methyl 4-(1-pyridin-2-yl-2,2-dipyridin-3-ylethyl)benzylcarbamate,
(±)-3-(1-pyridin-2-yl-2,2-dipyridin-3-ylethyl)benzamide,
(±)-3-(1-pyridin-2-yl-2,2-dipyridin-3-ylethyl)benzoic acid,
(±)-6-[1-(4-fluorophenyl)-2,2-dipyridin-3-ylethyl]pyridin-2-amine,
(±)-2-({3-[1-(4-fluorophenyl)-2,2-dipyridin-3-ylethyl]pyridin-2-yl}amino)ethanol,
(±)-N-{6-[1-(4-fluorophenyl)-2,2-dipyridin-3-ylethyl]pyridin-2-yl}acetamide,
(±)-N-{6-[1-(4-fluorophenyl)-2,2-dipyridin-3-ylethyl]pyridin-2-yl}methanesulfonamide,
(±)-N-[2-({6-[1-(4-fluorophenyl)-2,2-dipyridin-3-ylethyl]pyridin-2-yl}amino)ethyl]methanesulfonamide,
(±)-6-[1-(6-methoxypyridin-2-yl)-2,2-dipyridin-3-ylethyl]pyridin-2-amine,
(±)-5-[2-(4-fluorophenyl)-2-pyridin-2-yl-1-pyridin-3-ylethyl]pyridin-2-amine,
(±)-5-[1-(4-fluorophenyl)-2,2-dipyridin-3-ylethyl]pyridin-2-amine,
(±)-N-{6-[1-(4-fluorophenyl)-2,2-dipyridin-3-ylethyl]pyridin-2-yl}glycine,
(±)-3-[2-(6-aminopyridin-2-yl)-1-pyridin-2-yl-2-pyridin-3-ylethyl]benzonitrile,
(±)-3-[1-(6-aminopyridin-2-yl)-2,2-dipyridin-3-ylethyl]benzonitrile,
(±)-N-{6-[1-(3-cyanophenyl)-2,2-dipyridin-3-ylethyl]pyridin-2-yl}urea,
(±)-N-{6-[1-(3-cyanophenyl)-2,2-dipyridin-3-ylethyl]pyridin-2-yl}acetamide,
(±)-N-[2-({6-[1-(3-cyanophenyl)-2,2-dipyridin-3-ylethyl]pyridin-2-yl}amino)ethyl]acetamide,
(±)-N-[2-({6-[1-(3-cyanophenyl)-2,2-dipyridin-3-ylethyl]pyridin-2-yl}amino)ethyl]methanesulfonamide,
(±)-N-{6-[1-(6-methoxypyridin-2-yl)-2,2-dipyridin-3-ylethyl]pyridin-2-yl}acetamide,
(±)-N-{6-[1-(6-methoxypyridin-2-yl)-2,2-dipyridin-3-ylethyl]pyridin-2-yl}-N'-methylurea,
(±)-N-{6-[1-(4-cyanophenyl)-2,2-dipyridin-3-ylethyl]pyridin-2-yl}-N'-methylurea,
(±)-tert-butyl N-{6-[1-(3-cyanophenyl)-2,2-dipyridin-3-ylethyl]pyridin-2-yl}glycinate,
(±)-N-{6-[2-(3-cyanophenyl)-2-pyridin-2-yl-1-pyridin-3-ylethyl]pyridin-2-yl}acetamide,
(±)-N-{6-[2-(3-cyanophenyl)-2-pyridin-2-yl-1-pyridin-3-ylethyl]pyridin-2-yl}methanesulfonamide,
(±)-6-[1-(6-methoxypyridin-2-yl)-2,2-dipyridin-3-ylethyl]pyridine-2-carbonitrile,
(±)-N-[6-(1-pyridin-2-yl-2,2-dipyridin-3-ylethyl)pyridin-2-yl]acetamide,
(±)-6-(1-pyridin-2-yl-2,2-dipyridin-3-ylethyl)pyridin-2-amine,
(±)-N-({6-[1-(6-methoxypyridin-2-yl)-2,2-dipyridin-3-ylethyl]pyridin-2-yl}methyl)methanesulfonamide,
(±)-N-[6-(2-phenyl-2-pyridin-2-yl-1-pyridin-3-ylethyl)pyridin-2-yl]methanesulfonamide, (±)-N-{6-[2-(6-methoxypyridin-2-yl)-2-pyridin-2-yl-1-pyridin-3-ylethyl]pyridin-2-yl}methanesulfonamide,
(±)-N-{6-[2-(6-methoxypyridin-2-yl)-2-pyridin-2-yl-1-pyridin-3-ylethyl]pyridin-2-yl}methanesulfonamide,
(±)-N-[6-(2-phenyl-1,2-dipyridin-3-ylethyl)pyridin-2-yl]methanesulfonamide,
(±)-N-[6-(2-pyridin-2-yl-1,2-dipyridin-3-ylethyl)pyridin-2-yl]methanesulfonamide,
(±)-N-{6-[1-(4-fluorophenyl)-2,2-dipyridin-3-ylethyl]pyridin-2-yl}urea,
(±)-6-(2-phenyl-1,2-dipyridin-3-ylethyl)pyridin-2(1H)-one,
(±)-N-[6-(1,2,2-tripyridin-3-ylethyl)pyridin-2-yl]acetamide,
(±)-methyl 6-(1,2,2-tripyridin-3-ylethyl)pyridin-2-ylcarbamate,
(±)-tert-butyl 6-(1,2,2-tripyridin-3-ylethyl)pyridin-2-ylcarbamate,
(±)-6-(1,2,2-tripyridin-3-ylethyl)pyridin-2-amine,
(±)-2-methoxy-3-(1,2,2-tripyridin-3-ylethyl)pyridine,
(±)-2-methoxy-3-(1-pyridin-2-yl-2,2-dipyridin-3-ylethyl)benzonitrile,
3-(1,2-dipyridin-3-yl-2-pyrimidin-2-ylethyl)benzonitrile,
(±)-3-[1-(2-ethoxypyrimidin-4-yl)-2,2-dipyridin-3-ylethyl]benzonitrile,
(±)-3-{1-[2-(methylamino)pyrimidin-4-yl]-2,2-dipyridin-3-ylethyl}benzonitrile,
(±)-2-[(6-{1-[6-(2-hydroxyethyl)aminopyridin-2-yl]-2,2-dipyridin-3-ylethyl}pyridin-2-yl)amino]ethanol,
(±)-6-[2-(6-aminopyridin-2-yl)-1-pyridin-3-yl-2-pyridin-3-ylethyl]pyridin-2-amine,
(±)-6-[2-(6-aminopyridin-2-yl)-1-pyridin-2-yl-2-pyridin-3-ylethyl]pyridin-2-amine,
(±)-6-[1-(6-aminopyridin-2-yl)-2-pyridin-2-yl-2-pyridin-3-ylethyl]pyridin-2-amine,
(±)-6-[1-(6-aminopyridin-2-yl)-2-phenyl-2-pyridin-3-ylethyl]pyridin-2-amine,
(±)-6-[1-(6-aminopyridin-2-yl)-2-phenyl-2-pyridin-3-ylethyl]pyridin-2-amine,
(±)-2-(1-pyridin-2-yl-2,2-dipyridin-3-ylethyl)isonicotinonitrile,
(±)-3-(2,2-dipyridin-3-yl-1-pyrimidin-2-ylethyl)benzonitrile,
(±)-3-[2-(4-aminopyrimidin-2-yl)-1-(6-ammoniopyridin-2-yl)-2-(3-cyanophenyl)ethyl]pyridine,
2,2',2'',2'''-Ethane-1,1,2,2-tetrayltetrapyridine,
(±)-4-chloro-2-(1,2,2-tripyridin-3-ylethyl)pyridine,
(±)-1,2,2-tripyridin-3-yl-1-pyrimidin-4-ylethanol,
(±)-1-phenyl-2,2-dipyridin-3-yl-1-pyrimidin-2-ylethanol,
(±)-1,2,2-tripyridin-3-yl-1-pyrimidin-2-ylethanol,
1,1-diphenyl-2,2-dipyridin-3-ylethanol,
(±)-tert-Butyl 2-(2-hydroxy-1-phenyl-2,2-dipyridin-3-ylethyl)pyrrolidine-1-carboxylate,
(±)-2-(4-fluorophenyl)-2-(2-methyl-2H-tetrazol-5-yl)-1,1-dipyridin-3-ylethanol,
(±)-6-[1-(6-aminopyridin-2-yl)-2-(6-aminopyridin-2-yl)-2-pyridin-3-ylethyl]pyridin-2-amine,
(±)-4-[1-(6-methoxypyridin-2-yl)-2,2-dipyridin-3-ylethyl]-2-(methylthio)pyrimidine,
(±)-4-[1-(6-methoxypyridin-2-yl)-2,2-dipyridin-3-ylethyl]pyrimidin-2-amine,
(±)-methyl 6-[1-(4-fluorophenyl)-2,2-bis(2-fluoropyridin-3-yl)ethyl]pyridin-2-ylcarbamate,
(±)-N-{6-[1-(4-fluorophenyl)-2,2-bis(2-fluoropyridin-3-yl)ethyl]pyridin-2-yl}methanesulfonamide,
(±)-N-{6-[1-(4-fluorophenyl)-2,2-bis(2-fluoropyridin-3-yl)ethyl]pyridin-2-yl}urea,
(±)-methyl 6-[1-(4-fluorophenyl)-2,2-bis(5-methoxypyridin-3-yl)ethyl]pyridin-2-ylcarbamate, (±)-N-{6-[2,2-bis(6-chloropyridin-3-yl)-1-(4-fluorophenyl)ethyl]pyridin-2-yl}methanesulfonamide,
(±)-N-{6-[2,2-bis(6-aminopyridin-3-yl)-1-(4-fluorophenyl)ethyl]pyridin-2-yl}methanesulfonamide,
(±)-4-[1-(4-chlorophenyl)-2-(2-aminopyrimidin-4-yl)-2-pyridin-3-ylethyl]-2-aminopyrimidine,
N-{6-[2-(3-cyanophenyl)-1-(4-fluorophenyl)-2-pyridin-3-ylethyl]pyridin-2-yl}methanesulfonamide,
N-{6-[2-(4-cyanophenyl)-1-(4-fluorophenyl)-2-pyridin-3-ylethyl]pyridin-2-yl}methanesulfonamide,
N-{6-[(1S)-2-(4-cyanophenyl)-1-(4-fluorophenyl)-2-pyridin-3-ylethyl]pyridin-2-yl}methanesulfonamide,
N-{6-[(1R)-2-(4-cyanophenyl)-1-(4-fluorophenyl)-2-pyridin-3-ylethyl]pyridin-2-yl}methanesulfonamide,
4-[2-(6-aminopyridin-2-yl)-2-(4-fluorophenyl)-1-pyridin-3-ylethyl]benzonitrile,
2-[2-(6-bromopyridin-2-yl)-1,2-dipyridin-3-ylethyl]pyrazine,
2-[2-(6-bromopyridin-2-yl)-1,2-dipyridin-3-ylethyl]pyrazine,
6-(2-pyrazin-2-yl-1,2-dipyridin-3-ylethyl)pyridin-2-amine,
6-(2-pyrazin-2-yl-1,2-dipyridin-3-ylethyl)pyridin-2-amine,
N-[6-(2-pyrazin-2-yl-1,2-dipyridin-3-ylethyl)pyridin-2-yl]acetamide,
2-methoxy-3-[1-(2-methoxypyridin-3-yl)-2,2-dipyridin-3-ylethyl]pyridine,
3-[1-(4-fluorophenyl)-2,2-dipyridin-3-ylethyl]-2-piperidin-1-ylpyridine,
3-{1-[2-(2-hydroxyethoxy)pyridin-3-yl]-2,2-dipyridin-3-ylethyl}benzonitrile,
3-(2,2-dipyridin-3-yl-1-pyrimidin-5-ylethyl)benzonitrile,
N-{6-[1-(2-methoxypyridin-3-yl)-2,2-dipyridin-3-ylethyl]pyridin-2-yl}methanesulfonamide,
4-[1-(2-methoxypyridin-3-yl)-2,2-dipyridin-3-ylethyl]pyrimidin-2-amine,
N-{6-[1-(4-fluorophenyl)-2-(1,3-oxazol-2-yl)-2-pyridin-3-ylethyl]pyridin-2-yl}methanesulfonamide,
N-{6-[1-(4-fluorophenyl)-2-(1,3-oxazol-2-yl)-2-pyridin-3-ylethyl]pyridin-2-yl}methanesulfonamide,
N-{6-[1-(4-fluorophenyl)-2-(1,3,4-oxadiazol-2-yl)-2-pyridin-3-ylethyl]pyridin-2-yl}methanesulfonamide,
N-{6-[1-(4-fluorophenyl)-2-(1,3,4-oxadiazol-2-yl)-2-pyridin-3-ylethyl]pyridin-2-yl}methanesulfonamide,
4-[1-(2-aminopyrimidin-4-yl)-2-(1,3-oxazol-2-yl)-2-pyridin-3-ylethyl]benzonitrile,
4-[1-(2-aminopyrimidin-4-yl)-2-(1,3-oxazol-2-yl)-2-pyridin-3-ylethyl]benzonitrile,
3-[2-(1H-imidazol-2-yl)-2-phenyl-1-pyridin-3-ylethyl]pyridine,
2-hydroxy-n-{6-[1-(6-methoxypyridin-2-yl)-2,2-dipyridin-3-ylethyl]pyridin-2-yl}acetamide,
(±)-6-[1-(6-aminopyridin-2-yl)-2,2-di-(6-methoxypyridin-2-yl)-ethyl]pyridin-2-amine,
2-chloro-4-[1-(6-methoxypyridin-2-yl)-2,2-dipyridin-3-ylethyl]pyridine,
(±)-6-[1-(6-aminopyridin-2-y)-2-(6-methoxypyridin-2-yl)-2-pyridin-2-ylethyl]pyridin-2-amine,
3-[2,2-bis(6-aminopyridin-2-yl)-1-(6-methoxypyridin-2-yl)ethyl]benzonitrile,
N-{4-[1-(6-methoxypyridin-2-yl)-2,2-dipyridin-3-ylethyl]pyridin-2-yl}methanesulfonamide,
N-{4-[1-(6-methoxypyridin-2-yl)-2,2-dipyridin-3-ylethyl]pyridin-2-yl}urea,
N-{4-[1-(4-fluorophenyl)-2,2-dipyridin-3-ylethyl]pyrimidin-2-yl}methanesulfonamide,
N-{6-[1-(4-fluorophenyl)-2-(1-oxidopyridin-3-yl)-2-pyridin-3-ylethyl]pyridin-2-yl}methanesulfonamide, N-{5-[1-(4-fluorophenyl)-2,2-dipyridin-3-ylethyl]pyridin-2-yl}methanesulfonamide,
N-{5-[1-(4-fluorophenyl)-2,2-dipyridin-3-ylethyl]pyridin-2-yl}acetamide,
5-{6-[1-(4-fluorophenyl)-2,2-dipyridin-3-ylethyl]pyridin-2-yl}-1,3,4-thiadiazol-2-amine,
6-[1-(4-fluorophenyl)-2,2-dipyridin-3-ylethyl]-N-pyridin-3-ylpyridin-2-amine,
(±)-6-[1-(6-aminopyridin-2-yl)-2-(2-fluoropyridin-3-yl-2-(4-chlrophenyl)ethy]pyridin-2-amine,
4-[2,2-bis(6-aminopyridin-2-yl)-1-(2-fluoropyridin-3-yl)ethyl]benzonitrile,
(±)-6-[1-(6-aminopyridin-2-yl)-2-(3,4-dichlorophenyl)-2-pyridin-3-ylethyl]pyridin-2-amine,
4-[1,2-bis(6-aminopyridin-2-yl)-2-pyridin-3-ylethyl]benzonitrile,
4-[1,2-bis(6-aminopyridin-2-yl)-2-(2-fluoropyridin-3-yl)ethyl]benzonitrile,
4-[2-(2-aminopyrimidin-4-yl)-2-(4-chlorophenyl)-1-pyridin-3-ylethyl]benzonitrile,
N-{6-[2-(2-aminopyrimidin-4-yl)-2-(4-chlorophenyl)-1-pyridin-3-ylethyl]pyridin-2-yl}methanesulfonamide,
4-[2-(6-aminopyridin-2-yl)-1-(4-chlorophenyl)-2-pyridin-3-ylethyl]pyrimidin-2-amine,
4-[1,2-bis(2-aminopyrimidin-4-yl)-2-pyridin-3-ylethyl]benzonitrile,
(±)-4-[1-(4-chlorophenyl)-2-(2-aminopyrimidin-4-yl)-2-(2-fluoropyridin-3-yl)ethyl]-2-aminopyrimidine,
ethyl 6-(1,2,2-tripyridin-3-ylethyl)pyridin-2-ylcarbamate,
N-phenyl-N'-[6-(1,2,2-tripyridin-3-ylethyl)pyridin-2-yl]urea,
6-(1,2,2-tripyridin-3-ylethyl)pyridin-2-ylformamide,
ethyl {[6-(1,2,2-tripyridin-3-ylethyl)pyridin-2-yl]amino}carbonylcarbamate,
N-[6-(1,2,2-tripyridin-3-ylethyl)pyridin-2-yl]piperidine-1-carboxamide,
N-({6-[1-(6-methoxypyridin-2-yl)-2,2-dipyridin-3-ylethyl]pyridin-2-yl}methyl)acetamide,
6-[1-(6-methoxypyridin-2-yl)-2,2-dipyridin-3-ylethyl]-N-[2-(1 H-1,2,3-triazol-1-yl)ethyl]pyridin-2-amine,
4-[1,2,2-tris(6-aminopyridin-2-yl)ethyl]fluorobenzene,
3-[1,2,2-tris(6-aminopyridin-2-yl)ethyl]benzonitrile,
N~2~-{6-[1-(6-methoxypyridin-2-yl)-2,2-dipyridin-3-ylethyl]pyridin-2-yl}-N1,N1-dimethylglycinamide,
N-{6-[1-(4-fluorophenyl)-2,2-bis(6-methoxypyridin-3-yl)ethyl]pyridin-2-yl}methanesulfonamide,
methyl 6-[1-(6-methoxypyrimidin-2-yl)-2-(6-methoxypyridin-2-yl)-2-(6-methylcarbonylaminopyridin-3-yl)ethyl]pyridin-2-ylcarbamate,
(±)-6-[1-(4-fluorophenyl)-2-(6-aminopyridin-3-y)-2-(6-methoxypyridin-2-yethyl]pyridin-2-amine,
2-{2,2-dipyridin-3-yl-1-[6-(pyrrolidin-1-ylcarbonyl)pyridin-2-yl]ethyl}-6-methoxypyridine,
N~2~-{4-[1-(3-cyanophenyl)-2,2-dipyridin-3-ylethyl]pyrimidin-2-yl}-N1,N1-dimethylglycinamide,
4-[1-(6-methoxypyridin-3-yl)-2,2-dipyridin-3-ylethyl]pyrimidin-2-amine,
4-[1-(6-methoxypyridin-3-yl)-2,2-dipyridin-3-ylethyl]pyrimidin-2-amine,
N-{6-[1-(4-fluorophenyl)-2-(2-fluoropyridin-3-yl)-2-pyridin-3-ylethyl]pyridin-2-yl}methanesulfonamide,
N-{6-[1-(4-fluorophenyl)-2-(2-fluoropyridin-3-yl)-2-pyridin-3-ylethyl]pyridin-2-yl}methanesulfonamide,
methyl 6-[1-(4-fluorophenyl)-2-(2-fluoropyridin-3-yl)-2-pyridin-3-ylethyl]pyridin-2-ylcarbamate,
methyl 6-[1-(4-fluorophenyl)-2-(2-fluoropyridin-3-yl)-2-pyridin-3-ylethyl]pyridin-2-ylcarbamate,
N-{6-[1-(6-methoxypyridin-3-yl)-2,2-dipyridin-3-ylethyl]pyridin-2-yl}methanesulfonamide,
6-[1-(6-methoxypyridin-2-yl)-2,2-dipyridin-3-ylethyl]-N-pyridin-2-ylpyridine-2-carboxamide,
methyl 6-[1-(6-methoxypyridin-3-yl)-2,2-dipyridin-3-ylethyl]pyridin-2-ylcarbamate,
N-{6-[1-(3,4-dichlorophenyl)-2,2-dipyridin-3-ylethyl]pyridin-2-yl}methanesulfonamide,
N-{6-[1-(4-chlorophenyl)-2,2-dipyridin-3-ylethyl]pyridin-2-yl}methanesulfonamide,
N-(6-{2,2-dipyridin-3-yl-1-[4-(trifluoromethyl)phenyl]ethyl}pyridin-2-yl)methanesulfonamide,
4-[1-(4-chlorophenyl)-2,2-dipyridin-3-ylethyl]pyrimidin-2-amine,
4-[1-(6-aminopyridin-3-yl)-2,2-dipyridin-3-ylethyl]pyrimidin-2-amine bis(trifluoroacetate),
N-{6-[1-(4-chlorophenyl)-2-(2-fluoropyridin-3-yl)-2-pyridin-3-ylethyl]pyridin-2-yl}methanesulfonamide,
N-{6-[2-(2-fluoropyridin-3-yl)-1-(6-methoxypyridin-3-yl)-2-pyridin-3-ylethyl]pyridin-2-yl}methanesulfonamide,
N-{6-[2-(2-fluoropyridin-3-yl)-1-(6-methoxypyridin-3-yl)-2-pyridin-3-ylethyl]pyridin-2-yl}methanesulfonamide,
4-[1-(4-chlorophenyl)-2,2-dipyridin-3-ylethyl]-n-methylpyrimidin-2-amine,
N-{6-[1-(4-cyanophenyl)-2-(2-fluoropyridin-3-yl)-2-pyridin-3-ylethyl]pyridin-2-yl}methanesulfonamide,
N-{6-[1-(4-cyanophenyl)-2-(2-fluoropyridin-3-yl)-2-pyridin-3-ylethyl]pyridin-2-yl}methanesulfonamide,
4-[1-(6-chloropyridin-3-yl)-2,2-dipyridin-3-ylethyl]pyrimidine,
4-(1,2,2-tripyridin-3-ylethyl)pyrimidine,
4-[1-(2-aminopyrimidin-4-yl)-2,2-dipyridin-3-ylethyl]benzonitrile,
4-[1-(2-aminopyrimidin-4-yl)-2,2-dipyridin-3-ylethyl]benzonitrile,
5-(2,2-dipyridin-3-yl-1-pyrimidin-4-ylethyl)pyridin-2-amine,
4-[1-(3,4-dichlorophenyl)-2,2-dipyridin-3-ylethyl]pyrimidin-2-amine,
4-{2,2-dipyridin-3-yl-1-[4-(trifluoromethyl)phenyl]ethyl}pyrimidin-2-amine,
4-[1-(6-aminopyridin-2-yl)-2-(4-chlorophenyl)-2-pyridin-3-ylethyl]pyrimidin-2-amine,
4-[1-(6-aminopyridin-2-yl)-2-(4-chlorophenyl)-2-pyridin-3-ylethyl]pyrimidin-2-amine,
methyl 6-[1-(2-aminopyrimidin-4-yl)-2-(4-chlorophenyl)-2-pyridin-3-ylethyl]pyridin-2-ylcarbamate,
methyl 6-[1-(2-aminopyrimidin-4-yl)-2-(4-chlorophenyl)-2-pyridin-3-ylethyl]pyridin-2-ylcarbamate,
N-{2-[1-(4-fluorophenyl)-2,2-dipyridin-3-ylethyl]pyrimidin-4-yl}methanesulfonamide,
N-{4-[1-(3-bromophenyl)-2,2-dipyridin-3-ylethyl]pyrimidin-2-yl}methanesulfonamide,
2-[-(3-chlorophenyl)-2,2-dipyridin-3-ylethyl]-4-(methylthio)pyrimidine,
2-[1-(3-chlorophenyl)-2,2-dipyridin-3-ylethyl]pyrimidin-4-amine,
3-[1-(4-aminopyrimidin-2-yl)-2,2-dipyridin-3-ylethyl]benzonitrile,
3-[1-(4-chloropyrimidin-2-yl)-2-pyrazin-2-yl-2-pyridin-3-ylethyl]benzonitrile,
2-[2-(4-ammoniopyrimidin-2-yl)-2-(3-cyanophenyl)-1-pyridinium-3-ylethyl]pyrazin-1-ium tris(trifluoroacetate) and
2-[2-(4-ammoniopyrimidin-2-yl)-2-(3-cyanophenyl)-1-pyridinium-3-ylethyl]pyrazin-1-ium tris(trifluoroacetate).
A particular example of a compound of the invention is a compound selected from the group consisting of (R)-N-{6-[1-(4-fluorophenyl)-2,2-dipyridin-3-ylethyl]pyridin-2-yl}methanesulfonamide,
(S)-N-{6-[1-(4-fluorophenyl)-2,2-dipyridin-3-ylethyl]pyridin-2-yl}methanesulfonamide,
(R)-N-{6-[1-(3-cyanophenyl)-2,2-dipyridin-3-ylethyl]pyridin-2-yl}methanesulfonamide,
(S)-N-{6-[1-(3-cyanophenyl)-2,2-dipyridin-3-ylethyl]pyridin-2-yl}methanesulfonamide,
(R)-N-{6-[1-(6-methoxypyridin-2-yl)-2,2-dipyridin-3-ylethyl]pyridin-2-yl}methanesulfonamide,
(S)-N-{6-[1-(6-methoxypyridin-2-yl)-2,2-dipyridin-3-ylethyl]pyridin-2-yl}methanesulfonamide,
(R)-3-[1-(2-aminopyrimidin-4-yl)-2,2-dipyridin-3-ylethyl]benzonitrile, and
(S)-3-[1-(2-aminopyrimidin-4-yl)-2,2-dipyridin-3-ylethyl]benzonitrile.

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppresant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an antitachycardia device (e.g. a defibrillator or a pacemaker) in combination with a compound of claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —$CH_2C(O)$— groups (keto forms) may undergo tautomerism to form hydroxyl —$CH=C(OH)$— groups (enol forms). Both keto and enol forms are included within the scope of the present invention.

In addition compounds with carbon-carbon double bonds may occur in Z- and E- forms with all isomeric forms of the compounds being included in the present invention.

List of Abbreviations:
AAS atomic absorption spectroscopy
AIDS acquired immunodeficiency syndrome
AF atrial fibrillation
ACE angiotensin converting enzyme
APD action potential duration
Ar argon
Boc butoxycarbonyl
$Boc_2O$ di-tert-butyl dicarbonate
CHO Chinese hamster ovary
dba dibenzylidineacetone
DEA diethylamine
DMF dimethylformamide
DMSO dimethylsulfoxide
EDTA ethylenediaminetetraacetic acid
EGTA ethylenebis(oxyethylenenitrilo)tetraacetic acid
ESI electrospray ionization
$Et_3N$ triethylamine
EtOAc ethyl acetate
$Et_2O$ diethyl ether
$Et_3OBF_4$ triethyloxonium tetrafluoroborate
EtOH ethanol
FAAS flame atomic absorption spetroscopy
FBS fetal bovine serum
HBSS Hank's balanced salt solution
HEPES N-2-hydroxyethylpiperazine-N'-2-ethanesulphonic acid
HPLC high pressure liquid chromatography
HRMS high resolution mass spectrum
i-PrMgCl isopropyl magnesium chloride
i-PrOH isopropanol
INH inhibition
LDA lithium diisopropylamide
LiHMDS lithium hexamethyldisilazide
LRMS low resolution mass spectrum
LYS lysate
MeOH methanol
MS mass spectrum
n-BuLi n-butyllithium
NMR nuclear magnetic resonance
NSAID non-steroidal antiinflammatory drug
PBS phosphate-buffered saline
SUP supernatant
TAFI thrombin-activatable fibrinolysis inhibitor
TFA trifluoroacetic acid
THF tetrahydrofuran
TsOH p-toluenesulfonic acid As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH₃, ethyl may be represented by "Et" or CH₂CH₃, propyl may be represented by "Pr" or CH₂CH₂CH₃, butyl may be represented by "Bu" or CH₂CH₂CH₂CH₃, etc. "$C_1$-$C_6$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "CH₂CH₂" or alternatively, by "H₂C=CH₂". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetlyene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

Unless otherwise specifically noted as only "unsubstituted" or only "substituted", alkyl, alkenyl and alkynyl groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl) $CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH ($C_1$-$C_6$ alkyl), —NH($C_1$-$C_6$ alkyl)NHSO$_2$($C_1$-$C_6$ alkyl), —($C_1$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

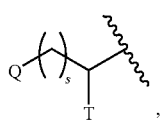

wherein s is an integer equal to zero, 1 or 2, the structure is

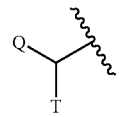

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

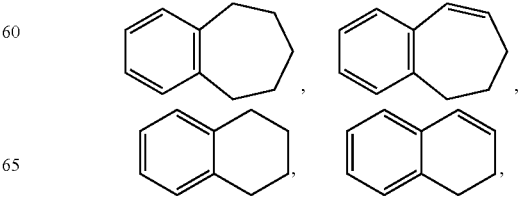

-continued

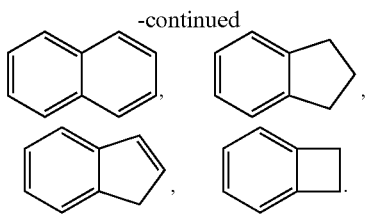

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH-, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

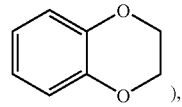), imidazo(2,1-b)(1,3)thiazole, (i.e.,

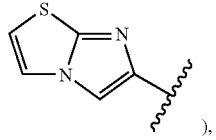), and benzo-1,3-dioxolyl (i.e.,

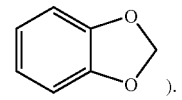).

In certain contexts herein,

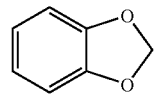

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

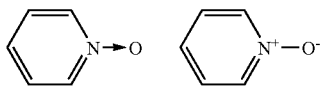

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

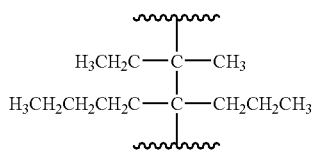

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto.

SCHEME I

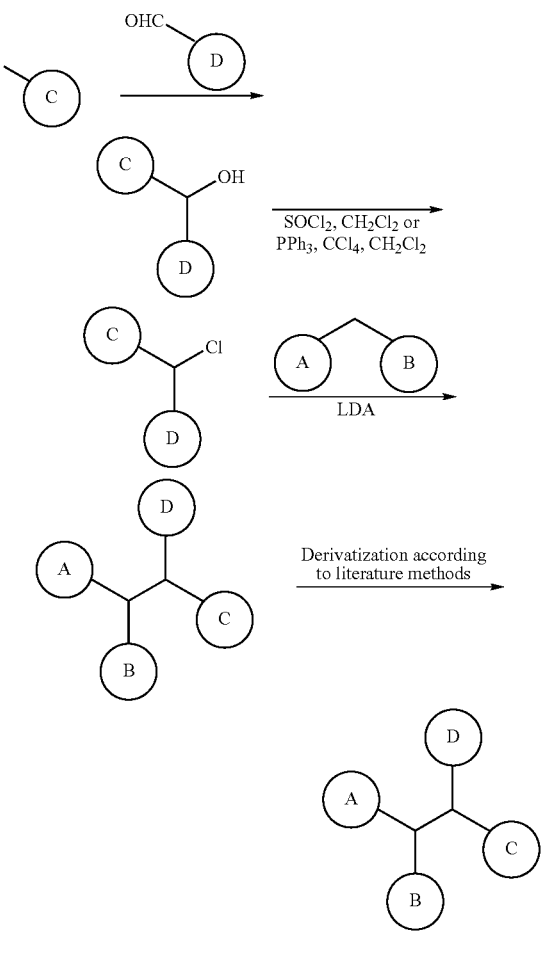

The variables A, B, C and D in the scheme are as defined in "Formula I".

EXAMPLE I-1

(R and S) N-{6-[1-(4-fluorophenyl)-2,2-dipyridin-3-ylethyl]pyridin-2-yl}methanesulfonamide

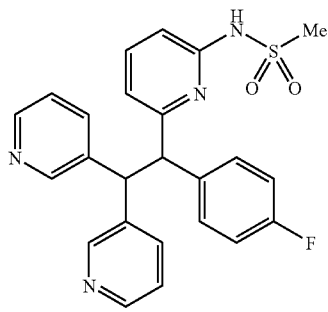

Step A

To a mixture of the 6-Bromo-2-pyridine carboxaldehyde (6.12 g, 32.90 mmol) in anhydrous THF (150 mL) @ −78° C.

under N₂ was added 4-fluorophenylmagnesium bromide (2M in diethyl ether, 17.27 mL) dropwise. The reaction was warmed to 0° C. and stirred for 1.5 hr. The reaction was quenched with saturated aqueous NH₄Cl. The combined organics were dried (anhd. Na₂SO₄), filtered, and concentrated to give (6-bromopyridin-2-yl)(4-fluorophenyl)methanol. ¹H NMR (500 MHz, CDCl₃) δ 7.50 (t, 1H, J=7.7), 7.40 (d, 1H, J=7.8), 7.38-7.32 (m, 2H), 7.10 (d, 1H, J=7.6), 7.03 (t, 2H, J=8.7), 5.73 (d, 1H, J=4.2), 4.43 (d, 1H, J=4.4), LRMS m/z (M+H) Calcd.: 282.0, found: 282.0.

Step B

To a mixture of (6-bromopyridin-2-yl)(4-fluorophenyl)methanol in CH₂Cl₂ (120 mL) @ 0° C. was added SOCl₂ (5.870 g, 49.34 mmol). The mixture was allowed to slowly warm to rt and stirred for 16 hr. The mixture was cooled back to 0° C. and quenched with saturated aqueous NaHCO₃. The resulting mixture was extracted 3× with CH₂Cl₂. The combined organics were dried (anhd. Na₂SO₄), filtered, and concentrated. The resulting residue was purified by silica gel chromatography (20-30% CH₂Cl₂ in Hexanes) to give 2-bromo-6-[chloro(4-fluorophenyl)methyl]pyridine. ¹H NMR (500 MHz, CDCl₃) δ 7.58 (t, 1H, J=7.7), 7.51 (d, 1H, J=7.6), 7.47-7.39 (m, 3H), 7.04 (t, 2H, J=8.7), 6.08 (s, 1H), LRMS m/z (M+H) Calcd.: 300.0, found: 300.0.

Step C

To a solution of 3-(pyridine-3-ylmethyl)pyridine (2.5 g, 14.69 mmol) in anhydrous THF (75 mL) under N2. The mixture was cooled to −78° C. and LDA (12.24 mL, 1.8 M) was added dropwise. The mixture was stirred @ −78° C. for 1 hr and 2-bromo-6-[chloro(4-fluorophenyl)methyl]pyridine (4.64 g, 15.42 mmol) was added. The mixture was warmed to 0° C. and stirred for 2 hr. The reaction was quenched with saturated aqueous NH₄Cl and extracted 3× with EtOAc. The combined organics were dried (anhd. Na₂SO₄) filtered, and concentrated. The resulting residue was purified by silica gel chromatography (1-3% MeOH in CH₂Cl₂) to give 2-bromo-6-[1-(4-fluorophenyl)-2,2-dipyridin-3-ylethyl]pyridine. ¹H NMR (500 MHz, CDCl₃) δ 8.55 (d, 1H, J=2.0), 8.45 (d, 1H, J=2.0), 8.35-8.29 (m, 2H), 7.60 (dt, 1H, J=7.9, 1.9), 7.49 (dt, 1H, J=7.9, 1.9), 7.35-7.24 (m, 3H), 7.17 (d, 1H, J=7.8), 7.14-7.07 (m, 2H), 7.05 (d, 1H, J=7.6), 6.86 (t, 2H, J=8.7), 5.13 (d, 1H, J=12.2), 4.78 (d, 1H, J=12.0) LRMS m/z (M+H) Calcd.: 434.0, found: 434.0. The racemic mixture was separated by ChiralPak AD (30% iPrOH in Hexane+DEA 1 mL/L). The first peak was enantiomer A of 2-bromo-6-[1-(4-fluorophenyl)-2,2-dipyridin-3-ylethyl]pyridine; HRMS m/z (M+H) Calcd.: 434.0663, found: 434.0648. And the second peak was enantiomer B of 2-bromo-6-[1-(4-fluorophenyl)-2,2-dipyridin-3-ylethyl]pyridine; HRMS m/z (M+H) Calcd.: 434.0633, found: 434.0646.

Step D

A mixture of 2-bromo-6-[1-(4-fluorophenyl)-2,2-dipyridin-3-ylethyl] (enantiomer A) (0.550 g, 1.266 mmol), methanesulfonamide (0.144 g, 1.518 mmol), Cs₂CO₃ (0.578 g, 1.774 mmol), Pd₂(dba)₃ (23 mg, 0.025 mmol) and xantphos (44 mg, 0.076 mmol) were stirred in anhydrous dioxane (5 mL). The mixture was degassed (3× pump/N₂) and heated to 100° C. for 16 hr under N₂. The mixture was cooled to rt, diluted with CHCl₃ and filtered through a pad of celite. The celite was washed with CHCl₃ and EtOAc. The filtrate was concentrated and purified by silica gel chromatography (1-5% MeOH in CH₂Cl₂) to give enantiomer A of N-{6-[1-(4-fluorophenyl)-2,2-dipyridin-3-ylethyl]pyridin-2-yl}methanesulfonamide. ¹H NMR(500 MHz, d₆ DMSO) δ 10.51 (s, 1H), 8.64 (d, 1H, J=2.0), 8.59 (d, 1H, J=2.0), 8.23 (dd, 2H, J=4.6, 1.5), 7.90 (dt, 1H, J=8.0, 1.9), 7.87 (d, 1H, J=7.8), 7.60-7.52 (m, 2H), 7.47 (t, 1H, J=7.8), 7.24-7.15 (m, 2H), 7.01 (d, 1H, J=7.3), 6.96 (t, 2H, J=8.9), 6.54 (d, 1H, J=8.0), 5.37 (d, 1H, J=12.2), 5.13 (d, 1H, J=12.5), 3.43 (s, 3H), HRMS m/z (M+H) Calcd: 449.1442, found: 449.1450. Enantiomer B of N-{6-[1-(4-fluorophenyl)-2,2-dipyridin-3-ylethyl]pyridin-2-yl}methanesulfonamide (HRMS m/z (M+H) Calcd.: 449.1442, found: 449.1459) was synthesized using the method described above except with enantiomer B of 2-bromo-6-[1-(4-fluorophenyl)-2,2-dipyridin-3-ylethyl]pyridine.

EXAMPLE I-2

(R and S) N-{6-[1-(3-cyanophenyl)-2,2-dipyridin-3-ylethyl]pyridin-2-yl}methanesulfonamide

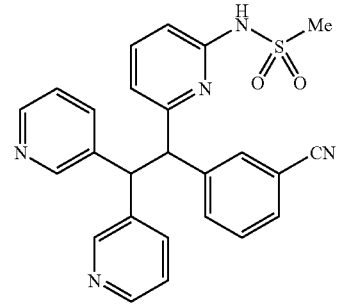

Step A

To a mixture of 2,6-dibromopyridine (6 g, 25.33 mmol) in anhydrous THF (150 mL) under N₂ @−78° C. was added n-BuLi (10.13 mL, 2.5M) dropwise. The mixture was stirred @ −78° C. for 15 min and 3-cyanobenzaldehyde (3.32 g, 25.33 mmol) in anhydrous THF (10 mL, rinsed with 5 mL) was added. The mixture was stirred for 20 min @ −78° C. then warmed to 0° C. and stirred for 1 hr. The mixture was quenched with saturated aqueous NH₄Cl, and the resulting mixture was extracted 3× with EtOAc. The combined organics were dried (anhd. Na₂SO₄), filtered, and concentrated. The residue was purified by silica gel chromatography (15-30% EtOAc in Hexanes) to give 3-[(6-bromopyridin-2-yl)(hydroxy)methyl]benzonitrile. LRMS m/z (M+H) Calcd.: 289.0, found 289.1.

Step B

To a mixture of 3-[(6-bromopyridin-2-yl)(hydroxy)methyl]benzonitrile (4.88 g, 16.88 mmol) in CH₂Cl₂ (60 mL) @ 0° C. under N₂ was added SOCl₂ (2.01 mL, 16.88 mmol). The mixture was warmed to rt and stirred for 48 hr. The mixture was cooled to 0° C. and quenched with saturated aqueous sodium bicarbonate and extracted 3× with CH₂Cl₂. The combined organics were dried (anhd. Na₂SO₄), filtered, and concentrated. The residue was purified by silica gel chromatography (25-50% CH₂Cl₂ in Hexanes) to give 3-[(6-bromopyridin-2-yl)(chloro)methyl]benzonitrile. LRMS m/z (M+H) Calcd.: 307.0, found: 307.0.

Step C

To a mixture of 3-(pyridine-3-ylmethyl)pyridine (0.700 g, 4.11 mmol) in anhydrous THF (20 mL) @ −78° C. under N₂ was added LDA (3.43 mL, 1.8 M) dropwise. The mixture was stirred for 1 hr @ −78° C., and 3-[(6-bromopyridin-2-yl)(chloro)methyl]benzonitrile was added. The reaction was warmed to 0° C., and stirred for 2 hr. The resulting mixture was quenched with saturated aqueous NH₄Cl, and extracted 3× with EtOAc. The combined organics were dried (anhd. Na₂SO₄), filtered, and concentrated. The residue was purified by silica gel chromatography (1-4% MeOH in CH₂Cl₂) to give racemic 3-[1-(6-bromopyridin-2-yl)-2,2-dipyridin-3-ylethyl]benzonitrile. LRMS m/z (M+H) Calcd.: 441.0, found: 441.0. The racemic mixture was separated by ChiralPak AD (40% iPrOH in Hexanes+1 mL/L DEA to 80% iPrOH in Hexanes+1 mL/L DEA over 45 min). The first peak was enantiomer A of 3-[1-(6-bromopyridin-2-yl)-2,2-dipyridin-3-ylethyl]benzonitrile, and the second peak was enantiomer B of 3-[1-(6-bromopyridin-2-yl)-2,2-dipyridin-3-ylethyl]benzonitrile.

Step D

A mixture of enantiomer A of 3-[1-(6-bromopyridin-2-yl)-2,2-dipyridin-3-ylethyl]benzonitrile (0.318 g, 0.721 mmol), methanesulfonamide (0.082 g, 0.865 mmol), Cs₂CO₃ (0.329 g, 1.01 mmol), Pd₂(dba)₃ (13 mg, 0.014 mmol) and xantphos (25 mg, 0.043 mmol) were stirred in anhydrous dioxane (5 mL). The mixture was degassed (3× pump/N₂) and heated to 100° C. for 16 hr under N₂. The reaction was cooled to rt, diluted with CHCl₃, and filtered through a pad of celite. The celite was washed with CHCl₃ and EtOAc to get rid of impurities. The celite was then washed with MeOH. The filtrate was concentrated and purified by silica gel chromatography (1-5% MeOH in CH₂Cl₂) to give enantiomer A of N-{6-[1-(3-cyanophenyl)-2,2-dipyridin-3-yethyl]pyridin-2-yl}methanesulfonamide. ¹H NMR (500 MHz d₆ DMSO) δ 10.57 (s, 1H), 8.63 (dd, 2H, J=5.6, 2.0), 8.29-8.20 (m, 2H), 8.04 (s, 1H), 7.90 (d, 2H, J=8.1), 7.84 (d, 1H, J=7.8), 7.55-7.45 (m, 2H), 7.35 (t, 1H, J=7.8), 7.20 (dd, 2H, J=7.9, 4.8), 7.03 (d, 1H, J=7.3), 6.57 (d, 1H, J=8.0), 5.47 (d, 1H, J=12.5), 5.15 (d, 1H, J=12.2), 3.46 (s, 3H), HRMS m/z (M+H) Calcd.: 456.1489, found: 456.1460. Enantiomer B of N-{6-[1-(3-cyanophenyl)-2,2-dipyridin-3-ylethyl]pyridin-2-yl}methanesulfonamide (HRMS m/z (M+H) Calcd.: 456.1489, found: 456.1469) was synthesized using the method described above except with enantiomer B of 3-[1-(6-bromopyridin-2-yl)-2,2-dipyridin-3-ylethyl]benzonitrile.

EXAMPLE I-3

(R and S) N-{6-[1-(6-methoxypyridin-2-yl)-2,2-dipyridin-3-ylethyl]pyridin-2-yl}methanesulfonamide

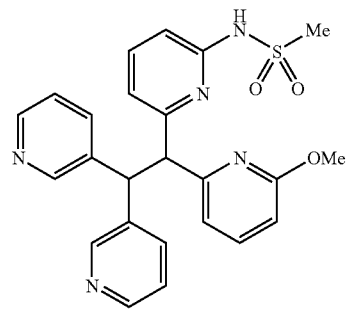

Step A

To a mixture of 2-bromo-6-methoxy-pyridine (5.00 g, 26.59 mmol) in anhydrous THF (100 mL) @ -78° C. under N₂ was added n-BuLi (11.701 mL, 2.5 M) dropwise. The mixture was stirred for 20 min and 6-Bromo-2-pyridine carboxaldehyde (4.95 g, 26.93 mmol was added. The mixture was warmed to 0° C. and stirred for 1 hr. The resulting mixture was quenched with saturated aqueous NH₄Cl, and extracted 3× with EtOAc. The combined organics were dried (anhd. Na₂SO₄), filtered, and concentrated. The residue was purified by silica gel chromatography (15% EtOAc in hexanes) to give (6-bromopyridin-2-yl)(6-methoxypyridin-2-yl)methanol. ¹H NMR (500 MHz, CDCl₃) δ 7.60-7.49 (m, 3H), 7.37 (dd, 1H, J=7.1, 1.5), 7.12 (d, 1H, J=7.3), 6.64 (d, 1H, J=8.3), 5.78 (d, 1H, J=5.4), 5.27 (d, 1H, J=5.4), 3.97 (s, 3H), LRMS m/z, (M+H) Calcd.: 295.0, found 295.1.

Step B

To a mixture of (6-bromopyridin-2-yl)(6-methoxypyridin-2-yl)methanol (5.11 g, 17.31 mmol) in CH2Cl2 (56 mL) @ 0° C. under N₂ was added SOCl₂ (3.09 g, 25.97 mmol). The mixture was then allowed to warm to rt and stirred for 3 hr. The mixture was then cooled back to 0° C. and quenched with saturated aqueous sodium bicarbonate. The resulting mixture was extracted 3× with CH₂Cl₂. The combined organics were dried (Na₂SO₄), filtered, and concentrated. The resulting residue was purified by silica gel chromatography (25-35% CH₂Cl₂ in Hexanes) to give 2-bromo-6-[chloro(6-methoxypyridin-2-yl)methyl]pyridine. ¹H NMR (500 MHz, CDCl₃) δ 7.76 (d, 1H, J=7.8), 7.61-7.54 (m, 2H), 7.41 (d, 1H, J=7.8), 7.12 (d, 1H, J=7.1), 6.66 (d, 1H, J=8.3), 6.02 (s, 1H), 3.86 (s, 3H), LRMS m/z (M+H) Calcd.: 313.0, found: 312.9.

Step C

To a mixture of 3-(pyridine-3-ylmethyl)pyridine (2 g, 11.75 mmol) in anhydrous THF (40 mL) @ -78° C. under N₂. was added LDA (9.79 mL, 1.8 M) dropwise. The mixture was stirred @ -78° C. for 1 hr and 2-bromo-6-[chloro(6-methoxypyridin-2-yl)methyl]pyridine was added. The mixture was warmed to 0° C. and stirred for 2 hr. The reaction was quenched with saturated aqueous NH₄Cl, and extracted 3× with EtOAc. The combined organics were dried (anhd. Na₂SO₄), filtered, and concentrated. The residue was purified by silica gel chromatography (1-5% MeOH in CH2Cl2) to give 2-bromo-6-[1-(6-methoxypyridin-2-yl)-2,2-dipyridin-3-ylethyl]pyridine. ¹H NMR (500 MHz, CDCl₃) δ 8.51 (t, 2H, J=2.7), 8.36-8.28 (m, 2H), 7.69 (dt, 1H, J=8.1, 2.0), 7.58 (dt, 1H, J=8.0, 1.9) 7.50 (d, 1H, J=7.6), 7.38-7.30 (m, 2H), 7.18 (d, 1H, J=7.8), 7.13 (dd, 1H, J=7.9, 4.8), 7.09 (dd, 1H, J=7.8, 4.9), 6.86 (d, 1H, J=7.3), 6.45 (d, 1H, J=8.1), 5.27 (d, 1H, J=12.2), 5.06 (d, 1H, J=12.5), 3.95 (s, 3H), LRMS m/z (M+H) Calcd.: 447.1, found: 447.1. The racemic mixture was separated by ChiralPak AD (40% EtOH in Hexanes+DEA 1 mL/L). The first peak was enantiomer A of 2-bromo-6-[1-(6-methoxypyridin-2-yl)-2,2-dipyridin-3-ylethyl]pyridine, and the second peak was enantiomer B of 2-bromo-6-[1-(6-methoxypyridin-2-yl)-2,2-dipyridin-3-ylethyl]pyridine.

Step D

A mixture of enantiomer A of 2-bromo-6-[1-(6-methoxypyridin-2-yl)-2,2-dipyridin-3-ylethyl]pyridine (1.00 g, 2.235 g), methanesulfonamide (0.255 g, 2.683 mmol), Cs₂CO₃ (1.02 g, 3.13 mmol), Pd₂(dba)₃ (41 mg, 0.045 mmol), and xantphos (78 mg, 0.134 mmol) in anhydrous dioxane (10 mL) under N₂ was degassed (3× pump/N₂) and heated to 100° C. for 16 hr. The mixture was cooled to rt and diluted with CHCl₃. The mixture was filtered through a pad of celite and washed with CHCl₃ and EtOAc. The filterate was concentrated and purified by silica gel chromatography (1-5% MeOH in CH₂Cl₂). The mixture was then purified by acidic reverse phase HPLC (95% H₂0:5% CH₃CN to 100% CH₃CN +0.1% TFA). The fractions were concentrated then quenched with saturated aqueous. sodium bicarbonate, and extracted 3× with EtOAc. The combined organic were dried (anhd. $Na_2SO_4$), filtered and concentrated to give N-{6-[1-(6-methoxypyridin-2-yl)-2,2-dipyridin-3-ylethyl]pyridin-2-yl}methanesulfonamide. $^1$H NMR (500 MHz, $d_6$ DMSO) δ 10.43 (s, 1H), 8.64 (d, 2H, J=8.3), 8.22 (t, 2H, J =5.2), 7.91 (td, 2H, J=6.2, 1.8, 7.55-7.40 (m, 2H), 7.25-7.10 (m, 3H) 7.06 (d, 1H, J=7.3), 6.55 (d, 1H, J=7.6), 6.44 (d, 1H, J=8.1), 5.43 (d, 1H, J=12.2), 5.39 (d, 1H, J=12.2), 3.82 (s, 3H), 3.45 (s, 3H), LRMS m/z (M+H) Calcd: 462.1595, found 462.1597. Enantiomer B of N-{6-[1-(6-methoxypyridin-2-yl)-2,2-dipyridin-3-ylethyl]pyridin-2-yl}methanesulfonamide (LRMS m/z (M+H) Calcd.: 462.1595, found 462.1597) was synthesized using the method described above except with enantiomer B of 2-bromo-6-[1-(6-methoxypyridin-2-yl)-2,2-dipyridin-3-ylethyl]pyridine.

EXAMPLE I-4

(R and S)-3-[1-(2-aminopyrimidin-4-yl-2,2-dipyridin-3-ylethyl]benzonitrile

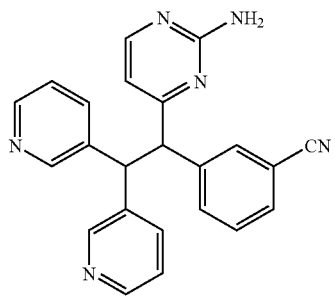

Step A

To the solution of 4-iodo-2-(methylthio)pyrimidine (2.52 g, 10 mmol) in THF (50 mL) at 0 ° C. was added i-PrMgCl (5 mL, 2.0 M, 10 mmol) and stirred for 1 h. 3-cyanobenzaldehyde (1.31 g, 10 mmol) was added. The mixture was stirred at 0° C. for 2 h. The reaction was quenched with saturated aqueous $NH_4Cl$ solution and extracted with $CH_2Cl_2$. The combined organic layer was dried, filtered, and concentrated. The residue was purified by silica gel chromatography (20-50% EtOAc in hexane) to give 3-{hydroxy[2-(methylthio)pyrimidin-4-yl]methyl}benzonitrile. $^1$H-NMR (500 MHz, $CDCl_3$) δ 8.46 (d, 1H, J=5.1), 7.72 (s, 1H), 7.65 (d, 1H, J=7.9), 7.61 (d, 1H, J=7.8), 7.48 (t, 1H, J=7.6), 6.84 (d, 1H, J=5.1), 5.69 (d, 1H, J=3.7), 4.58 (d, 1H, J=4.1), 2.60 (s, 3H). LRMS m/z (M+H) Calcd: 258.3, found: 258.1.

Step B

To the solution of 3-{hydroxy[2-(methylthio)pyrimidin-4-yl]methyl}benzonitrile (1.65 g, 6.41 mmol) in $CCl_4$ (10 mL) and $CH_2Cl_2$(10 mL) was added triphenylphophine (2.36 g, 8.98 mmol) and stirred for 4 h. The mixture was concentrated and the residue was purified by silica gel chromatography (20% EtOAc in hexane) to give 3-{chloro[2-(methylthio)pyrimidin-4-yl]methyl}benzonitrile. $^1$H-NMR (500 MHz, $CDCl_3$) δ 8.58 (d, 1H, J=5.1), 7.79 (s, 1H), 7.70 (d, 1H, J=8.1), 7.62 (d, 1H, J=7.8), 7.49 (t, 1H, J=7.8), 7.25 (d, 1H, J=4.9), 5.92 (1H), 2.51 (s, 3H). LRMS m/z (M+H) Calcd: 276.8, found: 276.0.

Step C

To the solution of 3-(pyridin-3-ylmethyl)pyridine (1.24 g, 7.26 mmol) in THF (32 mL) at −78° C. was added LDA (4.4 mL, 1.8 M) and stirred for 1 h. 3-{chloro[2-(methylthio)pyrimidin-4-yl]methyl}benzonitrile (2.0 g, 7.25 mmol) in THF (5 mL) was added. The mixture was stirred at 0° C. for 2 h. The reaction was quenched with ice and extracted with $CH_2Cl_2$. The combined organic layer was dried, filtered, and concentrated to give a solid. The solid was purified by silica gel chromatography (3% MeOH in $CH_2Cl_2$) to give (±)-3-{1-[2-(methylthio)pyrimidin-4-yl]-2,2-dipyridin-3-ylethyl}benzonitrile. LRMS m/z (M+H) Calcd: 410.5, found: 410.1.

Step D

To the solution of 3-{1-[2-(methylthio)pyrimidin-4-yl]-2,2-dipyridin-3-ylethyl}benzonitrile (1.2 g, 2.93 mmol) in $CHCl_3$ (15 mL) at 0° C. was added m-chloroperoxybenzoic acid (0.657 g, 77%, 2.93 mmol) and stirred for 1 h. The reaction mixture was concentrated and purified by silica gel chromatography (6% MeOH in $CH_2Cl_2$) to give a diastereomeric mixture of (±)-3-{1-[2-(methylsulfinyl)pyrimidin-4-yl]-2,2-dipyridin-3-ylethyl}benzonitrile. LRMS m/z (M+H) Calcd: 426.6, found: 426.1.

Step E

The solution of diastereomeric mixture of (±)-3-{1-[2-(methylsulfinyl)pyrimidin-4-yl]-2,2-dipyridin-3-ylethyl}benzonitrile (0.11 g, 0.25 mmol) in $NH_3$ saturated DMSO(2 mL) was heated to 100 ° C. in microwave for 2 h. The mixture was concentrated and the residue was purified by silica gel chromatography (5% MeOH in $CH_2Cl_2$) to give (±)-3-[1-(2-aminopyrimidin-4-yl)-2,2-dipyridin-3-ylethyl]benzonitrile. $^1$H-NMR (500 MHz, DMSO-$d_6$) δ 8.68 (d, 1H, J=1.5), 8.60 (d, 1H, J=1.5), 8.29 (d, 1H, J=4.6), 8.23 (d, 1H, J=4.6), 8.00 (d, 1H, J=4.8), 7.95 (s, 1H), 7.90(t, 2H, J=9.4), 7.80(d, 1H, J=8.0), 7.55 (d, 1H, J=7.6), 7.40 (t, 1H, J=7.8), 7.25(dd, 1H, J=7.8, 4.6), 7.19(dd, 1H, J=8.0, 4.6), 6.67(d, 1H, J=5.1), 6.54(s,2H), 5.25 (d, 1H, J=12.5), 5.20 (d, 1H, J=12.4). LRMS m/z (M+H) Calcd: 379.4, found: 379.2.

The racemic mixture was separated by Chiralcel OD (50% i-PrOH in hexane). The first peak was (−)-3-[1-(2-aminopyrimidin-4-yl)-2,2-dipyridin-3-ylethyl]benzonitrile. The second peak was (+)-3-[1-(2-aminopyrimidin-4-yl)-2,2-dipyridin-3-ylethyl]benzonitrile.

EXAMPLE I-5

6-[1-(6-aminopyridin-2-yl)-2,2-dipyridin-3-ylethyl]pyridin-2-amine

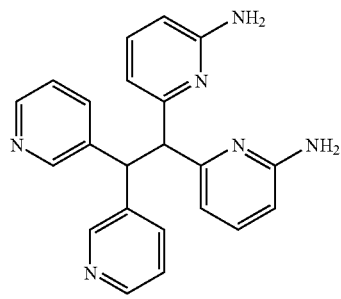

Step A

To the solution of 2,6-dibromopyridine (4.72 g, 19.93 mmol) in THF (100 mL) at −78° C. was added n-BuLi (8.8 mL, 2.5 M, 22 mmol) and stirred for 20 min. 6-Bromo-2-pyridinecarboxaldehyde (3.71 g, 19.93 mmol) was added. The mixture was stirred at 0° C. for 2 h. The reaction was quenched with ice and extracted with $CH_2Cl_2$. The combined organic layer was dried, filtered, and concentrated to give a solid. The solid was purified by silica gel chromatography (15% EtOAc in hexane) to give bis(6-bromopyridin-2-yl)methanol. LRMS m/z (M+H) Calcd: 345.0, found: 344.9.

Step B

To the solution of bis(6-bromopyridin-2-yl)methanol (1.07 g, 3.11 mmol) in $CCl_4$ (15 mL) and $CH_2Cl_2$ (15 mL) was added triphenylphophine (1.14 g, 4.36 mmol) and stirred overnight. The mixture was concentrated and the residue was purified by silica gel chromatography (5-10% EtOAc in hexane) to give 2-bromo-6-[(6-bromopyridin-2-yl)(chloro)methyl]pyridine. LRMS m/z (M+H) Calcd: 362.5, found: 362.8.

Step C

To the solution of 3-(pyridin-3-ylmethyl)pyridine (0.085 g, 0.5 mmol) in THF (5 mL) at −78° C. was added LDA (0.3 mL, 1.8 M) and stirred for 1 h. 2-Bromo-6-[(6-bromopyridin-2-yl)(chloro)methyl]pyridine (0.181 g, 0.5 mmol) in THF (2 mL) was added. The mixture was stirred at 0° C. for 1 h. The reaction was quenched with ice and extracted with $CH_2Cl_2$. The combined organic layer was dried, filtered, and concentrated to give a solid. The solid was purified by silica gel chromatography (50% EtOAc in hexane) to give 2-bromo-6-[1-(6-bromopyridin-2-yl)-2-pyridin-2-yl-2-pyridin-3-ylethyl]pyridine. $^1$H-NMR (500 MHz, $CDCl_3$) δ 8.58 (d, 1H, J=1.9), 8.47 (d, 1H, J=4.9), 8.30 (dd, 1H, J=4.7, 1.5), 7.95 (d, 1H, J=8.1), 7.44 (td, 1H, J=7.6, 1.7), 7.39 (t, 2H, J=7.7), 7.28-7.33 (m, 2H), 7.20 (d, 1H, J=7.6), 7.15 (dd, 2H, J=7.7, 4.7), 7.10 (dd, 1H, J=7.9, 4.8), 6.97 (dd, 1H, J=7.4, 4.8), 5.45 (d, 1H, J=12.0), 5.29 (d, 1H, J=12.0). LRMS m/z (M+H) Calcd: 497.2, found: 496.9.

Step D

The mixture of 2-bromo-6-[1-(6-bromopyridin-2-yl)-2-pyridin-2-yl-2-pyridin-3-ylethyl]pyridine (0.180 g, 0.363 mmol), tert-butylcarbamate (0.102 g, 0.871 mmol), $Pd_2(dba)_3$ (0.017 g, 0.018 mmol), xantphos (0.031 g, 0.054 mmol), $Cs_2CO_3$ (0.331 g, 1.016 mmol) in dioxane (5 mL) was degassed and heated to 100° C. for 14 h. The reaction mixture was diluted with water and extracted with $CH_2Cl_2$. The combined organic layer was dried, filtered, and concentrated to give a solid. The solid was purified by silica gel chromatography (2-4% MeOH in $CH_2Cl_2$) to give tert-butyl 6-(1-{6-[(tert-butoxycarbonyl)amino]pyridin-2-yl}-2,2-dipyridin-3-ylethyl)pyridin-2-ylcarbamate. LRMS m/z (M+H) Calcd: 569.7, found: 569.2.

Step E

To the solution of tert-butyl 6-(1-{6-[(tert-butoxycarbonyl)amino]pyridin-2-yl}-2-pyridin-2-yl-2-pyridin-3-ylethyl)pyridin-2-ylcarbamate (0.12 g, 0.211 mmol) in $CH_2Cl_2$ (2 mL) was added $CF_3COOH$ (2 mL) and stirred for 1 h. The mixture was concentrated and the residue was dissolved in MeOH (3 mL). Potassium carbonate (200 mg) was added and stirred for 0.5 h. The mixture was filtered and the filtrate concentrated. The residue was purified by silica gel chromatography (10% MeOH in $CH_2Cl_2$) to give the title compound. $^1$H-NMR (500 MHz, DMSO-$d_6$) δ 8.60 (s, 2H), 8.32 (d, 2H, J=4.6), 7.92 (d, 2H, J=7.8), 7.41 (s, 2H), 7.28 (dd, 2H, J=7.7, 4.7), 7.15 (broad, 4H), 6.60 (d, 2H, J=7.4), 6.46 (s,2H), 5.25 (d, 1H, J=10.3), 4.98 (broad, 1H). LRMS m/z (M+H) Calcd: 369.4, found: 369.1.

The following compounds were made according to Scheme I where intermediates in the scheme were modified according to literature methods. Examples I-130- I-135 were prepared via addition of an appropriate aryllithium reagent to 4-chloro-6-carbomethoxy-pyridine. In each case, the resulting ketone was reduced ($NaBH_4$) to provide an alcohol which was elaborated in accordance with Scheme I.

EXAMPLES I-6-I-250

| Example | Compound | Name | MS (M + 1) |
|---|---|---|---|
| I-6 | (structure) | (±)-3-(2,2-diphenyl-1-pyridin-3-ylethyl)pyridine | 337.2 |

-continued

| Example | Compound | Name | MS (M + 1) |
|---|---|---|---|
| I-7 | | (±)-2-fluoro-5-[1-(4-fluorophenyl)-2,2-dipyridin-3-ylethyl]pyridine | 374.1 |
| I-8 | | (±)-3-(1,2,2-tripyridin-3-ylethyl)pyridine | 339.2 |
| I-9 | | (±)-3-(1-pyridin-2-yl-2,2-dipyridin-3-ylethyl)benzonitrile | 363.1 |
| I-10 | | (±)-4-(1-pyridin-2-yl-2,2-dipyridin-3-ylethyl)benzonitrile | 363.0 |
| I-11 | | (±)-2-chloro-5-[1-(4-fluorophenyl)-2,2-dipyridin-3-ylethyl]pyridine | 390.0 |

-continued

| Example | Compound | Name | MS (M + 1) |
|---|---|---|---|
| I-12 | | (±)-3-[1-(4-fluorophenyl)-2,2-dipyridin-3-ylethyl]pyridine | 356.1550 |
| I-13 | | (±)-2-[1-(4-fluorophenyl)-2,2-dipyridin-3-ylethyl]pyridine | 3561.1563 |
| I-14 | | (±)-3-[2-(4-fluorophenyl)-1-pyridin-3-yl-2-pyridin-4-ylethyl]pyridine | 356.1557 |
| I-15 | | (±)-3-[2,2-bis(4-fluorophenyl)-1-pyridin-3-ylethyl]pyridine | 373.1511 |
| I-16 | | (±)-2-[1-(4-fluorophenyl)-2-(1,2,4-oxadiazol-3-yl)-2-pyridin-3-ylethyl]pyridine (Diastereomer A) | 347.1325 |

-continued

| Example | Compound | Name | MS (M + 1) |
|---|---|---|---|
| I-17 | Diastereomer A | (±)-2-chloro-3-[2-(4-fluorophenyl)-2-pyridin-2-yl-1-pyridin-3-ylethyl]pyridine | 390.1162 |
| I-18 | Diastereomer B | (±)-2-chloro-3-[2-(4-fluorophenyl)-2-pyridin-2-yl-1-pyridin-3-ylethyl]pyridine | 390.1175 |
| I-19 | | (±)-2-chloro-3-[1-(4-fluorophenyl)-2,2-dipyridin-3-yletbyl]pyridine | 390.1167 |
| I-20 | Diastereomer A | (±)-2-fluoro-5-[2-(4-fluorophenyl)-2-pyridin-2-yl-1-pyridin-3-ylethyl]pyridine | 374.1484 |

-continued

| Example | Compound | Name | MS (M + 1) |
|---|---|---|---|
| I-21 | Diastereomer B | (±)-2-fluoro-5-[2-(4-fluorophenyl)-2-pyridin-2-yl-1-pyridin-3-ylethyl]pyridine | 374.1487 |
| I-22 | | (±)-3-[2-(6-bromopyridin-2-yl)-1-pyridin-2-yl-2-pyridin-3-ylethyl]benzonitrile Diastereomeric mixture | 441.0707 |
| I-23 | | (±)-3-[1-(6-oxo-1,6-dihydropyridin-2-yl)-2,2-dipyridin-3-ylethyl]benzonitrile | 379.1550 |
| I-24 | | (±)-2-bromo-6-[1-(4-fluorophenyl)-2,2-dipyridin-3-ylethyl]pyridine | 436.0 |
| I-25 | | (±)-N-{6-[1-(4-fluorophenyl)-2,2-dipyridin-3-ylethyl]pyridin-2-yl}ethane-1,2-diamine | 414.2 |

| Example | Compound | Name | MS (M + 1) |
| --- | --- | --- | --- |
| I-26 | | (±)-2-azido-6-[1-(4-fluorophenyl)-2,2-dipyridin-3-ylethyl]pyridine | 397.0 |
| I-27 | | (±)-6-[1-(4-fluorophenyl)-2,2-dipyridin-3-ylethyl]-N,N-dimethylpyridin-2-amine | 399.0 |
| I-28 | | (±)-6-[1-(4-fluorophenyl)-2,2-dipyridin-3-ylethyl]pyridin-2-amine | 371.0 |
| I-29 | | (±)-2-({6-[1-(4-fluorophenyl)-2,2-dipyridin-3-ylethyl]pyridin-2-yl}amino)ethanol | 415.1 |
| I-30 | | (±)-N-ethyl-N'-[2-({6-[1-(4-fluorophenyl)-2,2-dipyridin-3-ylethyl]pyridin-2-yl}amino)ethyl]urea | 485.1 |

-continued

| Example | Compound | Name | MS (M + 1) |
|---|---|---|---|
| I-31 | | (±)-6-[1-(4-fluorophenyl)-2,2-dipyridin-3-ylethyl]pyridine-2-carboxamide | 399.1 |
| I-32 | | (±)-2-bromo-6-[1-(6-methoxypyridin-2-yl)-2,2-dipyridin-3-ylethyl]pyridine | 447.0 |
| I-33 | | (±)-6-[1-(6-chloropyridin-2-yl)-2,2-dipyridin-3-ylethyl]pyridin-2(1H)-one | 389.0 |
| I-34 | | (±)-N-{5-[1-(4-fluorophenyl)-2,2-dipyridin-3-ylethyl]pyridin-2-yl}ethane-1,2-diamine | 414.1 |

-continued

| Example | Compound | Name | MS (M + 1) |
|---|---|---|---|
| I-35 | | (±)-methyl 3-(1-pyridin-2-yl-2,2-dipyridin-3-ylethyl)benzylcarbamate | 424.9 |
| I-36 | | (±)-methyl 4-(1-pyridin-2-yl-2,2-dipyridin-3-ylethyl)benzylcarbamate | 425.0 |
| I-37 | | (±)-3-(1-pyridin-2-yl-2,2-dipyridin-3-ylethyl)benzamide | 380.2 |
| I-38 | | (±)-3-( 1-pyridin-2-yl-2,2-dipyridin-3-ylethyl)benzoic acid | 382.1 |
| I-39 | | (±)-6-[1-(4-fluorophenyl)-2,2-dipyridin-3-ylethyl]pyridin-2-amine | 371.1682 |

-continued

| Example | Compound | Name | MS (M + 1) |
|---|---|---|---|
| I-40 | | (±)-2-({3-[1-(4-fluorophenyl)-2,2-dipyridin-3-ylethyl]pyridin-2-yl}amino)ethanol | 415.1920 |
| I-41 | | (±)-N-{6-[1-(4-fluorophenyl)-2,2-dipyridin-3-ylethyl]pyridin-2-yl}acetamide | 413.1763 |
| I-42 | | (±)-N-Δ6-[1-(4-fluorophenyl)-2,2-dipyridin-3-ylethyl]pyridin-2-yl}methanesulfonamide | 449.1424 |
| I-43 | | (±)-N-{6-[1-(4-fluorophenyl)-2,2-dipyridin-3-ylethyl]pyridin-2-yl}-N'-methylurea | 428.1863 |
| I-44 | | (±)-N-[2-({6-[1-(4-fluorophenyl)-2,2-dipyridin-3-ylethyl]pyridin-2-yl}amino)ethyl]methanesulfonamide | 492.1825 |

-continued

| Example | Compound | Name | MS (M + 1) |
|---|---|---|---|
| I-45 | | (±)-tert-butyl 6-[1-(4-fluorophenyl)-2,2-dipyridin-3-ylethyl]pyridin-2-ylcarbamate | 471.2179 |
| I-46 | | (±)-tert-butyl 6-[1-(6-methoxypyridin-2-yl)-2,2-dipyridin-3-ylethyl]pyridin-2-ylcarbamate | 484.2355 |
| I-47 | | (±)-6-[1-(6-methoxypyridin-2-yl)-2,2-dipyridin-3-ylethyl]pyridin-2-amine | 384.1816 |
| I-48 | | (±)-5-[2-(4-fluorophenyl)-2-pyridin-2-yl-1-pyridin-3-ylethyl]pyridin-2-amine Diastereomeric mixture | 371.1680 |
| I-49 | | (±)-5-[1-(4-fluorophenyl)-2,2-dipyridin-3-ylethyl]pyridin-2-amine | 371.1672 |

-continued

| Example | Compound | Name | MS (M + 1) |
|---|---|---|---|
| I-50 | | (±)-N-{6-[1-(4-fluorophenyl)-2,2-dipyridin-3-ylethyl]pyridin-2-yl}glycine | 429.1716 |
| I-51 | Diastereomer A | (±)-3-[2-(6-aminopyridin-2-yl)-1-pyridin-2-yl-2-pyridin-3-ylethyl]benzonitrile | 378.1709 |
| I-52 | Diastereomer B | (±)-3-[2-(6-aminopyridin-2-yl)-1-pyridin-2-yl-2-pyridin-3-ylethyl]benzonitrile | 378.1710 |
| I-53 | | (±)-3-[1-(6-aminopyridin-2-yl)-2,2-dipyridin-3-ylethyl]benzonitrile | 378.1711 |

-continued

| Example | Compound | Name | MS (M + 1) |
|---|---|---|---|
| I-54 | | (±)-N-{6-[1-(3-cyanophenyl)-2,2-dipyridin-3-ylethyl]pyridin-2-yl}urea | 421.1783 |
| I-55 | | (±)-N-{6-[1-(3-cyanophenyl)-2,2-dipyridin-3-ylethyl]pyridin-2-yl}acetamide | 420.1827 |
| I-56 | | (±)-N-[2-({6-[1-(3-cyanophenyl)-2,2-dipyridin-3-ylethyl]pyridin-2-yl}amino)ethyl]acetamide | 463.2237 |
| I-57 | | (±)-N-[2-({6-[1-(3-cyanophenyl)-2,2-dipyridin-3-ylethyl]pyridin-2-yl}amino)ethyl]methanesulfonamide | 499.1905 |

| Example | Compound | Name | MS (M + 1) |
| --- | --- | --- | --- |
| I-58 | | (±)-N-{6-[1-(6-methoxypyridin-2-yl)-2,2-dipyridin-3-ylethyl]pyridin-2-yl}acetamide | 426.1914 |
| I-59 | | (±)-N-{6-[1-(6-methoxypyridin-2-yl)-2,2-dipyridin-3-ylethyl]pyridin-2-yl}-N'-methylurea | 441.2028 |
| I-60 | | (±)-N-{6-[1-(4-cyanophenyl)-2,2-dipyridin-3-ylethyl]pyridin-2-yl}acetamide | 420.1819 |
| I-61 | | (±)-N-{6-[1-(4-cyanophenyl)-2,2-dipyridin-3-ylethyl]pyridin-2-yl}-N'-methylurea | 435.1922 |
| I-62 | | (±)-N-{6-[1-(4-cyanophenyl)-2,2-dipyridin-3-ylethyl]pyridin-2-yl}urea | 421.1766 |

| Example | Compound | Name | MS (M + 1) |
|---|---|---|---|
| I-63 | | (±)-N-{6-[1-(4-cyanophenyl)-2,2-dipyridin-3-ylethyl]pyridin-2-yl}methanesulfonamide | 456.1488 |
| I-64 | | (±)-4-[1-(6-aminopyridin-2-yl)-2,2-dipyridin-3-ylethyl]benzonitrile | 378.1693 |
| I-65 | | (±)-tert-butyl N-{6-[1-(3-cyanophenyl)-2,2-dipyridin-3-ylethyl]pyridin-2-yl}glycinate | 492.2374 |
| I-66 | Diastereomer A | (±)-N-{6-[2-(3-cyanophenyl)-2-pyridin-2-yl-1-pyridin-3-ylethyl]pyridin-2-yl}acetamide | 420.1805 |

-continued

| Example | Compound | Name | MS (M + 1) |
|---|---|---|---|
| I-67 | Diastereomer B | (±)-N-{6-[2-(3-cyanophenyl)-2-pyridin-2-yl-1-pyridin-3-ylethyl]pyridin-2-yl}acetamide | 420.1804 |
| I-68 | Diastereomer A | (±)-N-{6-[2-(3-cyanophenyl)-2-pyridin-2-yl-1-pyridin-3-ylethyl]pyridin-2-yl}methanesulfonamide | 456.1478 |
| I-69 | Diastereomer B | (±)-N-{6-[2-(3-cyanophenyl)-2-pyridin-2-yl-1-pyridin-3-ylethyl]pyridin-2-yl}methanesulfonamide | 456.1478 |
| I-70 | | (±)-6-[1-(6-methoxypyridin-2-yl)-2,2-dipyridin-3-ylethyl]pyridine-2-carbonitrile | 394.1650 |

| Example | Compound | Name | MS (M + 1) |
|---|---|---|---|
| I-71 | | (±)-N-[6-(1-pyridin-2-yl-2,2-dipyridin-3-ylethyl)pyridin-2-yl]acetamide | 396.1805 |
| I-72 | | (±)-N-[6-(1-pyridin-2-yl-2,2-dipyridin-3-ylethyl)pyridin-2-yl]methanesulfonamide | 432.1479 |
| I-73 | | (±)-N-methyl-N'-[6-(1-pyridin-2-yl-2,2-dipyridin-3-ylethyl)pyridin-2-yl]urea | 411.1931 |
| I-74 | | (±)-N-{6-[1-(6-methoxypyridin-2-yl)-2,2-dipyridin-3-ylethyl]pyridin-2-yl}urea | 397.1775 |
| I-75 | | (±)-6-(1-pyridin-2-yl-2,2-dipyridin-3-ylethyl)pyridin-2-amine | 354.1723 |

-continued

| Example | Compound | Name | MS (M + 1) |
|---|---|---|---|
| I-76 | | (±)-6-[1-(6-methoxypyridin-2-yl)-2,2-dipyridin-3-ylethyl]pyridine-2-carboxamide | 412.1767 |
| I-77 | | (±)-N-({6-[1-(6-methoxypyridin-2-yl)-2,2-dipyridin-3-ylethyl]pyridin-2-yl}methyl)methanesulfonamide | 476.1740 |
| I-78 | Diastereomer A | (±)-N-[6-(2-phenyl-2-pyridin-2-yl-1-pyridin-3-ylethyl)pyridin-2-yl]methanesulfonamide | 431.1525 |
| I-79 | Diastereomer B | (±)-N-[6-(2-phenyl-2-pyridin-2-yl-1-pyridin-3-ylethyl)pyridin-2-yl]methanesulfonamide | 431.1539 |

-continued

| Example | Compound | Name | MS (M + 1) |
|---|---|---|---|
| I-80 | | (±)-N-{6-[2-(6-methoxypyridin-2-yl)-2-pyridin-2-yl-1-pyridin-3-ylethyl]pyridin-2-yl}methanesulfonamide (Diastereomer A) | 462.1564 |
| I-81 | | (±)-N-{6-[2-(6-methoxypyridin-2-yl)-2-pyridin-2-yl-1-pyridin-3-ylethyl]pyridin-2-yl}methanesulfonamide (Diastereomer B) | 462.1566 |
| I-82 | | (±)-N-{6-[2-(6-methoxypyridin-2-yl)-2-pyridin-2-yl-1-pyridin-3-ylethyl]pyridin-2-yl}methanesulfonamide (Diastereomer A) | 456.1509 |
| I-83 | | (±)-N-{6-[2-(6-methoxypyridin-2-yl)-2-pyridin-2-yl-1-pyridin-3-ylethyl]pyridin-2-yl}methanesulfonamide (Diastereomer B) | 456.1490 |
| I-84 | | (±)-N-[6-(2-phenyl-1,2-dipyridin-3-ylethyl)pyridin-2-yl]methanesulfonamide (Diastereomer A) | 431.1530 |

-continued

| Example | Compound | Name | MS (M + 1) |
|---|---|---|---|
| I-85 | | (±)-N-[6-(2-phenyl-1,2-dipyridin-3-ylethyl)pyridin-2-yl]methanesulfonamide (Diastereomer B) | 431.1532 |
| I-86 | | (±)-N-[6-(2-pyridin-2-yl-1,2-dipyridin-3-ylethyl)pyridin-2-yl]methanesulfonamide (Diastereomer A) | 432.1479 |
| I-87 | | (±)-N-[6-(2-pyridin-2-yl-1,2-dipyridin-3-ylethyl)pyridin-2-yl]methanesulfonamide (Diastereomer B) | 432.1478 |
| I-88 | | (±)-6-(2-phenyl-2-pyridin-2-yl-1-pyridin-3-ylethyl)pyridin-2-amine (Diastereomer A) | 353.1770 |
| I-89 | | (±)-6-(2-phenyl-2-pyridin-2-yl-1-pyridin-3-ylethyl)pyridin-2-amine (Diastereomer B) | 353.1772 |

| Example | Compound | Name | MS (M + 1) |
|---|---|---|---|
| I-90 | | (±)-N-{6-[1-(4-fluorophenyl)-2,2-dipyridin-3-ylethyl]pyridin-2-yl}urea | 414.1732 |
| I-91 | | (±)-6-(2-phenyl-1,2-dipyridin-3-ylethyl)pyridin-2(1H)-one (Diastereomer A) | 354.1611 |
| I-92 | | (±)-2-bromo-6-(1,2,2-tripyridin-3-ylethyl)pyridine | 419.0 |
| I-93 | | (±)-N-[6-(1,2,2-tripyridin-3-ylethyl)pyridin-2-yl]acetamide | 396.1 |
| I-94 | | (±)-N-[6-(1,2,2-tripyridin-3-ylethyl)pyridin-2-yl]methanesulfonamide | 432.1 |

| Example | Compound | Name | MS (M + 1) |
|---|---|---|---|
| I-95 | | (±)-methyl 6-(1,2,2-tripyridin-3-ylethyl)pyridin-2-ylcarbamate | 412.0 |
| I-96 | | (±)-N,N-dimethyl-N'-[6-(1,2,2-tripyridin-3-ylethyl)pyridin-2-yl]urea | 425.1 |
| I-97 | | (±)-tert-butyl 6-(1,2,2-tripyridin-3-ylethyl)pyridin-2-ylcarbamate | 454.2 |
| I-98 | | (±)-6-(1,2,2-tripyridin-3-ylethyl)pyridin-2-amine | 354.1 |
| I-99 | | (±)-2-bromo-6-(1-pyridin-2-yl-2,2-dipyridin-3-ylethyl)phenol | 432.0702 |

-continued

| Example | Compound | Name | MS (M + 1) |
|---|---|---|---|
| I-100 | | (±)-2-methoxy-5-(1-pyridin-2-yl-2,2-dipyridin-3-ylethyl)benzonitrile | 393.1698 |
| I-101 | | (±)-2-hydroxy-5-(1-pyridin-2-yl-2,2-dipyridin-3-ylethyl)benzonitrile | 379.1535 |
| I-102 | | (±)-3-[1-(2-methoxypyridin-3-yl)-2,2-dipyridin-3-ylethyl]benzonitrile | 393.1686 |
| I-103 | | (±)-3-[1-(2-oxo-1,2-dihydropyridin-3-yl)-2,2-dipyridin-3-ylethyl]benzonitrile | 379.1535 |
| I-104 | | (±)-3-(1-pyridin-2-yl-2,2-dipyridin-3-ylethyl)pyridin-2(1H)-one | 355.1540 |
| I-105 | | (±)-2-methoxy-3-(1,2,2-tripyridin-3-ylethyl)pyridine | 369.1707 |

-continued

| Example | Compound | Name | MS (M + 1) |
|---|---|---|---|
| I-106 | | (±)-3-(1,2,2-tripyridin-3-ylethyl)pyridin-2(1H)-one | 355.1557 |
| I-107 | | (±)-2-methoxy-3-(1-pyridin-2-yl-2,2-dipyridin-3-ylethyl)benzonitrile | 393.1722 |
| I-108 | | (±)-2-hydroxy-3-(1-pyridin-2-yl-2,2-dipyridin-3-ylethyl)benzonitrile | 379.1557 |
| I-109 | | N-{6-[1-(6-methoxypyridin-2-yl)-2-pyridin-3-yl-2-pyrimidin-2-ylethyl]pyridin-2-yl}methanesulfonamide (mixture of diastereomers) | 463.1530 |
| I-110 | | 3-(1,2-dipyridin-3-yl-2-pyrimidin-2-ylethyl)benzonitrile (mixture of diastereomers) | 364.1543 |

-continued
| Example | Compound | Name | MS (M + 1) |
|---|---|---|---|
| I-111 | 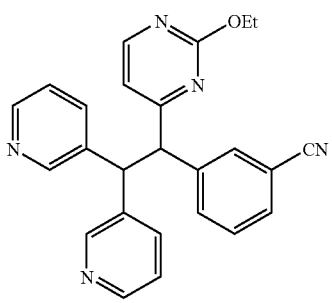 | (±)-3-[1-(2-ethoxypyrimidin-4-yl)-2,2-dipyridin-3-ylethyl]benzonitrile | 408.0 |
| I-112 | 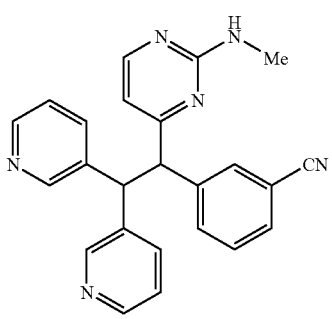 | (±)-3-{1-[2-(methylamino)pyrimidin-4-yl]-2,2-dipyridin-3-ylethyl}benzonitrile | 393.1 |
| I-113 | 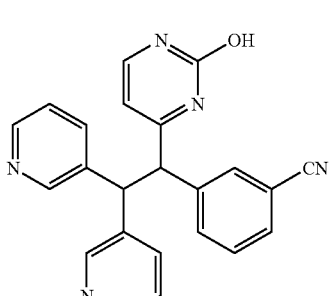 | (±)-3-[1-(2-hydroxypyrimidin-4-yl)-2,2-dipyridin-3-ylethyl]benzonitrile | 380.1 |
| I-114 | 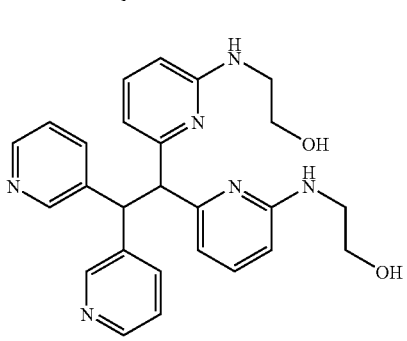 | (±)-2-[(6-{1-[6-(2-hydroxyethyl)aminopyridin-2-yl]-2,2-dipyridin-3-ylethyl}pyridin-2-yl)amino]ethanol | 457.2 |
| I-115 | 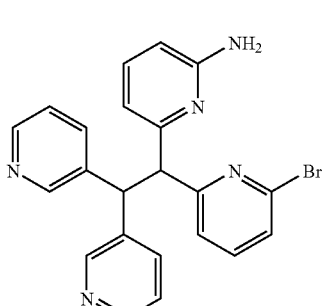 | (±)-6-[1-(6-bromopyridin-2-yl)-2,2-dipyridin-3-ylethyl]pyridin-2-amine | 432.0 |

| Example | Compound | Name | MS (M + 1) |
|---|---|---|---|
| I-116 | | (±)-6-[1-(6-bromopyridin-2-yl)-2,2-dipyridin-3-ylethyl]pyridine-2-carbonitrile | 389.1 |
| I-117 | | (±)-6-[2-(6-aminopyridin-2-yl)-1-pyridin-3-yl-2-pyridin-3-ylethyl]pyridin-2-amine (Diastereomer A) | 369.1801 |
| I-118 | | (±)-6-[2-(6-aminopyridin-2-yl)-1-pyridin-3-yl-2-pyridin-3-ylethyl]pyridin-2-amine (Diastereomer B) | 369.1809 |
| I-119 | | (±)-6-[2-(6-aminopyridin-2-yl)-1-pyridin-2-yl-2-pyridin-3-ylethyl]pyridin-2-amine (Diastereomer A) | 369.1812 |
| I-120 | | (±)-6-[2-(6-aminopyridin-2-yl)-1-pyridin-2-yl-2-pyridin-3-ylethyl]pyridin-2-amine (Diastereomer B) | 369.1813 |

-continued

| Example | Compound | Name | MS (M + 1) |
|---|---|---|---|
| I-121 | | (±)-2-bromo-6-[1-(6-bromopyridin-2-yl)-2-phenyl-2-pyridin-2-ylethyl]pyridine | 495.8 |
| I-122 | | (±)-2-bromo-6-[1-(6-bromopyridin-2-yl)-2-phenyl-2-pyridin-3-ylethyl]pyridine | 495.8 |
| I-123 | | (±)-2-bromo-6-[1-(6-bromopyridin-2-yl)-2-pyridin-2-yl-2-pyridin-3-ylethyl]pyridine | 496.9 |
| I-124 | | (±)-tert-butyl 6-(1-{6-[(tert-butoxycarbonyl)amino]pyridin-2-yl}-2-phenyl-2-pyridin-3-ylethyl)pyridin-2-ylcarbamate | 568.1 |
| I-125 | | (±)-tert-butyl 6-(1-{6-[(tert-butoxycarbonyl)amino]pyridin-2-yl}-2-phenyl-2-pyridin-2-ylethyl)pyridin-2-ylcarbamate | 568.1 |

-continued

| Example | Compound | Name | MS (M + 1) |
|---|---|---|---|
| I-126 | | (±)-tert-butyl 6-(1-{6-[(tert-butoxycarbonyl)amino]pyridin-2-yl}-2-pyridin-2-yl-2-pyridin-3-ylethyl)pyridin-2-ylcarbamate | 569.2 |
| I-127 | | (±)-6-[1-(6-aminopyridin-2-yl)-2-pyridin-2-yl-2-pyridin-3-ylethyl]pyridin-2-amine | 369.1 |
| I-128 | | (±)-6-[1-(6-aminopyridin-2-yl)-2-phenyl-2-pyridin-3-ylethyl]pyridin-2-amine | 368.1 |
| I-129 | | (±)-6-[1-(6-aminopyridin-2-yl)-2-phenyl-2-pyridin-2-ylethyl]pyridin-2-amine | 368.1 |
| I-130 | | 4-chloro-2-(1-pyridin-2-yl-2,2-dipyridin-3-ylethyl)pyridine | 373.1225 |

-continued

| Example | Name | MS (M + 1) |
|---|---|---|
| I-131 | N-[2-(1-pyridin-2-yl-2,2-dipyridin-3-ylethyl)pyridin-4-yl]methanesulfonamide | 432.1486 |
| I-132 | 2-(1-pyridin-2-yl-2,2-dipyridin-3-ylethyl)isonicotinonitrile | 364.1555 |
| I-133 | 2-[1-(6-bromopyridin-2-yl)-2,2-dipyridin-3-ylethyl]-4-chloropyridine | 451.0316 |
| I-134 | N-{6-[1-(4-chloropyridin-2-yl)-2,2-dipyridin-3-ylethyl]pyridin-2-yl}methanesulfonamide | 466.1074 |
| I-135 | N-{6-[1-(4-cyanopyridin-2-yl)-2,2-dipyridin-3-ylethyl]pyridin-2-yl}methanesulfonamide | 457.1434 |

-continued

| Example | Name | MS (M + 1) |
|---|---|---|
| I-136 | (±)-6-[1-(6-aminopyridin-2-yl)-2-(6-aminopyridin-2-yl)-2-pyridin-3-ylethyl]pyridin-2-amine | 384.15 |
| I-137 | (±)-4-[1-(6-methoxypyridin-2-yl)-2,2-dipyridin-3-ylethyl]-2-(methylthio)pyrimidine | 416.2 |
| I-138 | (±)-4-[1-(6-methoxypyridin-2-yl)-2,2-dipyridin-3-ylethyl]pyrimidin-2-amine | 385.2 |
| I-139 | (±)-methyl 6-[1-(4-fluorophenyl)-2,2-bis(2-fluoropyridin-3-yl)ethyl]pyridin-2-ylcarbamate | 465.2 |
| I-140 | (±)-N-{6-[1-(4-fluorophenyl)-2,2-bis(2-fluoropyridin-3-yl)ethyl]pyridin-2-yl}methanesulfonamide | 485.1 |

| Example | Compound | Name | MS (M + 1) |
|---|---|---|---|
| I-141 | | (±)-N-{6-[1-(4-fluorophenyl)-2,2-bis(2-fluoropyridin-3-yl)ethyl]pyridin-2-yl}urea | 450.17 |
| I-142 | | (±)-methyl 6-[1-(4-fluorophenyl)-2,2-bis(5-methoxypyridin-3-yl)ethyl]pyridin-2-ylcarbamate | 489.2 |
| I-143 | | (±)-N-{6-[2,2-bis(6-chloropyridin-3-yl)-1-(4-fluorophenyl)ethyl]pyridin-2-yl}methanesulfonamide | 517.1 |
| I-144 | | (±)-N-{6-[2,2-bis(6-aminopyridin-3-yl)-1-(4-fluorophenyl)ethyl]pyridin-2-yl}methanesulfonamide | 479.3 |

-continued

| Example | Compound | Name | MS (M + 1) |
|---|---|---|---|
| I-145 | | (±)-4-[1-(4-chlorophenyl)-2-(2-aminopyrimidin-4-yl)-2-pyridin-3-ylethyl]-2-aminopyrimidine (Diastereomer A) | 404.3 |
| I-146 | | (±)-4-[1-(4-chlorophenyl)-2-(2-aminopyrimidin-4-yl)-2-pyridin-3-ylethyl]-2-aminopyrimidine (Diastereomer B) | 404.3 |
| I-147 | | N-{6-[2-(3-cyanophenyl)-1-(4-fluorophenyl)-2-pyridin-3-ylethyl]pyridin-2-yl}methanesulfonamide (Diastereomer A) | 473.1417 |
| I-148 | | N-{6-[2-(3-cyanophenyl)-1-(4-fluorophenyl)-2-pyridin-3-ylethyl]pyridin-2-yl}methanesulfonamide (Diastereomer B) | 473.1415 |
| I-149 | | N-{6-[2-(4-cyanophenyl)-1-(4-fluorophenyl)-2-pyridin-3-ylethyl]pyridin-2-yl}methanesulfonamide (Diastereomer A) | 473.1443 |

-continued

| Example | Compound | Name | MS (M + 1) |
|---|---|---|---|
| I-150 | | N-{6-[2-(4-cyanophenyl)-1-(4-fluorophenyl)-2-pyridin-3-ylethyl]pyridin-2-yl}methanesulfonamide (Diastereomer B) | 473.144 |
| I-151 | | N-{6-[(1s)-2-(4-cyanophenyl)-1-(4-fluorophenyl)-2-pyridin-3-ylethyl]pyridin-2-yl}methanesulfonamide (Enantiomer A of I-149) | 473.1438 |
| I-152 | | N-{6-[(1S)-2-(4-cyanophenyl)-1-(4-fluorophenyl)-2-pyridin-3-ylethyl]pyridin-2-yl}methanesulfonamide (Enantiomer A of I-150) | 473.1437 |
| I-153 | | N-{6-[(1R)-2-(4-cyanophenyl)-1-(4-fluorophenyl)-2-pyridin-3-ylethyl]pyridin-2-yl}methanesulfonamide (Enantiomer B of I-149) | 473.1425 |

-continued

| Example | Compound | Name | MS (M + 1) |
|---|---|---|---|
| I-154 | | 4-[2-(6-aminopyridin-2-yl)-2-(4-fluorophenyl)-1-pyridin-3-ylethyl]benzonitrile (Diastereomer A) | 395.1688 |
| I-155 | | 4-[2-(6-aminopyridin-2-yl)-2-(4-fluorophenyl)-1-pyridin-3-ylethyl]benzonitrile (Diastereomer B) | 395.169 |
| I-156 | | 2-[2-(6-bromopyridin-2-yl)-1,2-dipyridin-3-ylethyl]pyrazine | 418.069 |
| I-157 | | 2-[2-(6-bromopyridin-2-yl)-1,2-dipyridin-3-ylethyl]pyrazine | 418.0693 |

-continued

| Example | Name | MS (M + 1) |
|---|---|---|
| I-158 | 6-(2-pyrazin-2-yl-1,2-dipyridin-3-ylethyl)pyridin-2-amine | 355.1678 |
| I-159 | 6-(2-pyrazin-2-yl-1,2-dipyridin-3-ylethyl)pyridin-2-amine | 355.1676 |
| I-160 | N-[6-(2-pyrazin-2-yl-1,2-dipyridin-3-ylethyl)pyridin-2-yl]acetamide, tris(tfa) salt | 397.1789 |
| I-161 | 2-methoxy-3-[1-(2-methoxypyridin-3-yl)-2,2-dipyridin-3-ylethyl]pyridine | 399.1821 |
| I-162 | 3-[1-(4-fluorophenyl)-2,2-dipyridin-3-ylethyl]-2-piperidin-1-ylpyridine | 439.2 |

| Example | Compound | Name | MS (M + 1) |
|---|---|---|---|
| I-163 | | 3-{1-[2-(2-hydroxyethoxy)pyridin-3-yl]-2,2-dipyridin-3-ylethyl}benzonitrile | 423.1832 |
| I-164 | | 3-(2,2-dipyridin-3-yl-1-pyrimidin-5-ylethyl)benzonitrile | 364.1543 |
| I-165 | | N-{6-[1-(2-methoxypyridin-3-yl)-2,2-dipyridin-3-ylethyl]pyridin-2-yl}methanesulfonamide | 462.1614 |
| I-166 | | 4-[1-(2-methoxypyridin-3-yl)-2,2-dipyridin-3-ylethyl]pyrimidin-2-amine | 385.1783 |
| I-167 | | N-{6-[1-(4-fluorophenyl)-2-(1,3-oxazol-2-yl)-2-pyridin-3-ylethyl]pyridin-2-yl}methanesulfonamide | 439.1218 |

-continued

| Example | Compound | Name | MS (M + 1) |
|---------|----------|------|------------|
| I-168 | | N-{6-[1-(4-fluorophenyl)-2-(1,3-oxazol-2-yl)-2-pyridin-3-ylethyl]pyridin-2-yl}methanesulfonamide | 439.1215 |
| I-169 | | N-{6-[1-(4-fluorophenyl)-2-(1,3,4-oxadiazol-2-yl)-2-pyridin-3-ylethyl]pyridin-2-yl}methanesulfonamide | 440.1175 |
| I-170 | | N-{6-[1-(4-fluorophenyl)-2-(1,3,4-oxadiazol-2-yl)-2-pyridin-3-ylethyl]pyridin-2-yl}methanesulfonamide | 440.1174 |
| I-171 | | 4-[1-(2-aminopyrimidin-4-yl)-2-(1,3-oxazol-2-yl)-2-pyridin-3-ylethyl]benzonitrile | 369.1454 |
| I-172 | | 4-[1-(2-aminopyrimidin-4-yl)-2-(1,3-oxazol-2-yl)-2-pyridin-3-ylethyl]benzonitrile | 369.1453 |

-continued

| Example | Compound | Name | MS (M + 1) |
|---|---|---|---|
| I-173 | | 3-[2-(1H-imidazol-2-yl)-2-phenyl-1-pyridin-3-ylethyl]pyridine | 327.1620 |
| I-174 | | 2-hydroxy-n-{6-[1-(6-methoxypyridin-2-yl)-2,2-dipyridin-3-ylethyl]pyridin-2-yl}acetamide | 442.1862 |
| I-175 | | (±)-6-[1-(6-aminopyridin-2-yl)-2,2-di-(6-methoxypyridin-2-yl)-ethyl]pyridin-2-amine | 429.2015 |
| I-176 | | 2-chloro-4-[1-(6-methoxypyridin-2-yl)-2,2-dipyridin-3-ylethyl]pyridine | 403.1298 |
| I-177 | | (±)-6-[1-(6-aminopyridin-2-yl)-2-(6-methoxypyridin-2-yl)-2-pyridin-2-ylethyl]pyridin-2-amine | 399.1910 |

-continued

| Example | Compound | Name | MS (M + 1) |
|---|---|---|---|
| I-178 | | 3-[2,2-bis(6-aminopyridin-2-yl)-1-(6-methoxypyridin-2-yl)ethyl]benzonitrile | 423.1910 |
| I-179 | | N-{4-[1-(6-methoxypyridin-2-yl)-2,2-dipyridin-3-ylethyl]pyridin-2-yl}methanesulfonamide | 462.1607 |
| I-180 | | N-{4-[1-(6-methoxypyridin-2-yl)-2,2-dipyridin-3-ylethyl]pyridin-2-yl}urea | 427.1889 |
| I-181 | | N-{4-[1-(4-fluorophenyl)-2,2-dipyridin-3-ylethyl]pyrimidin-2-yl}methanesulfonamide | 450.1420 |
| I-182 | | N-{6-[1-(4-fluorophenyl)-2-(1-oxidopyridin-3-yl)-2-pyridin-3-ylethyl]pyridin-2-yl}methanesulfonamide | 465.1421 |

-continued

| Example | Compound | Name | MS (M + 1) |
|---|---|---|---|
| I-183 | (structure with NHSO₂Me) | N-{5-[1-(4-fluorophenyl)-2,2-dipyridin-3-ylethyl]pyridin-2-yl}methanesulfonamide | 449.1487 |
| I-184 | (structure with NHCOMe) | N-{5-[1-(4-fluorophenyl)-2,2-dipyridin-3-ylethyl]pyridin-2-yl}acetamide | 413.1777 |
| I-185 | (structure with thiadiazole-NH₂) | 5-{6-[1-(4-fluorophenyl)-2,2-dipyridin-3-ylethyl]pyridin-2-yl}-1,3,4-thiadiazol-2-amine | 455.1425 |
| I-186 | (structure with NH-pyridinyl) | 6-[1-(4-fluorophenyl)-2,2-dipyridin-3-ylethyl]-N-pyridin-3-ylpyridin-2-amine | 448.1931 |

-continued

| Example | Compound | Name | MS (M + 1) |
|---|---|---|---|
| I-187 | | (±)-6-[1-(6-aminopyridin-2-yl)-2-(2-fluoropyridin-3-yl-2-(4-chlrophenyl)ethyl]pyridin-2-amine | 440.1401 |
| I-188 | | 4-[2,2-bis(6-aminopyridin-2-yl)-1-(2-fluoropyridin-3-yl)ethyl]benzonitrile | 411.1713 |
| I-189 | | (±)-6-[1-(6-aminopyridin-2-yl)-2-(3,4-dichlorophenyl)-2-pyridin-3-ylethyl]pyridin-2-amine | 402.1495 |
| I-190 | | 4-[1,2-bis(6-aminopyridin-2-yl)-2-pyridin-3-ylethyl]benzonitrile | 393.1835 |

-continued

| Example | Compound | Name | MS (M + 1) |
|---|---|---|---|
| I-191 | | 4-[1,2-bis(6-aminopyridin-2-yl)-2-pyridin-3-ylethyl]benzonitrile (Diastereomer 2) | 393.1828 |
| I-192 | | 4-[1,2-bis(6-aminopyridin-2-yl)-2-(2-fluoropyridin-3-yl)ethyl]benzonitrile (Diastereomer A) | 411.1744 |
| I-193 | | 4-[1,2-bis(6-aminopyridin-2-yl)-2-(2-fluoropyridin-3-yl)ethyl]benzonitrile (Diastereomer B) | 411.1744 |
| I-194 | | 4-[2-(2-aminopyrimidin-4-yl)-2-(4-chlorophenyl)-1-pyridin-3-ylethyl]benzonitrile (Diastereomer A) | 412.1321 |

-continued

| Example | Compound | Name | MS (M + 1) |
|---|---|---|---|
| I-195 | | N-{6-[2-(2-aminopyrimidin-4-yl)-2-(4-chlorophenyl)-1-pyridin-3-ylethyl]pyridin-2-yl}methanesulfonamide (Diastereomer A) | 481.03 |
| I-196 | | N-{6-[2-(2-aminopyrimidin-4-yl)-2-(4-chlorophenyl)-1-pyridin-3-ylethyl]pyridin-2-yl}methanesulfonamide (Diasteremer B) | 481.1201 |
| I-197 | | 4-[2-(6-aminopyridin-2-yl)-1-(4-chlorophenyl)-2-pyridin-3-ylethyl]pyrimidin-2-amine (Diastereomer A) | 403.1429 |
| I-198 | | 4-[2-(6-aminopyridin-2-yl)-1-(4-chlorophenyl)-2-pyridin-3-ylethyl]pyrimidin-2-amine (Diasteremoer B) | 403.1420 |
| I-199 | | 4-[1,2-bis(2-aminopyrimidin-4-yl)-2-pyridin-3-ylethyl]benzonitrile (Mixture od Diastereomers) | 395.1688 |

-continued

| Example | Compound | Name | MS (M + 1) |
|---|---|---|---|
| I-200 | | (±)-4-[1-(4-chlorophenyl)-2-(2-aminopyrimidin-4-yl)-2-(2-fluoropyridin-3-yl)ethyl]-2-aminopyrimidine (Diastereomer A) | 421.96 |
| I-201 | | (±)-4-[1-(4-chlorophenyl)-2-(2-aminopyrimidin-4-yl)-2-(2-fluoropyridin-3-yl)ethyl]-2-aminopyrimidine (Diastereomer B) | 421.95 |
| I-202 | | ethyl 6-(1,2,2-tripyridin-3-ylethyl)pyridin-2-ylcarbamate | 426.2 |
| I-203 | | N-phenyl-N'-[6-(1,2,2-tripyridin-3-ylethyl)pyridin-2-yl]urea | 473.2 |
| I-204 | | 6-(1,2,2-tripyridin-3-ylethyl)pyridin-2-ylformamide | 382.1691 |

| Example | Compound | Name | MS (M + 1) |
|---|---|---|---|
| I-205 | | ethyl {[6-(1,2,2-tripyridin-3-ylethyl)pyridin-2-yl]amino}carbonylcarbamate | 469.2 |
| I-206 | | N-[6-(1,2,2-tripyridin-3-ylethyl)pyridin-2-yl]piperidine-1-carboxamide | 465.3 |
| I-207 | | N-({6-[1-(6-methoxypyridin-2-yl)-2,2-dipyridin-3-ylethyl]pyridin-2-yl}methyl)acetamide | 440.20 |
| I-208 | | 6-[1-(6-methoxypyridin-2-yl)-2,2-dipyridin-3-ylethyl]-N-[2-(1H-1,2,3-triazol-1-yl)ethyl]pyridin-2-amine | 479.25 |

-continued

| Example | Compound | Name | MS (M + 1) |
|---|---|---|---|
| I-209 | | 4-[1,2,2-tris(6-aminopyridin-2-yl)ethyl]fluorobenzene | 401.2 |
| I-210 | | 3-[1,2,2-tris(6-aminopyridin-2-yl)ethyl]benzonitrile | 408.2 |
| I-211 | | N~-2~-{6-[1-(6-methoxypyridin-2-yl)-2,2-dipyridin-3-ylethyl]pyridin-2-yl}-N$^1$,N$^1$-dimethylglycinamide | 469.2 |
| I-212 | | N-{6-[1-(4-fluorophenyl)-2,2-bis(6-methoxypyridin-3-yl)ethyl]pyridin-2-yl}methanesulfonamide | 509.1 |

-continued

| Example | Compound | Name | MS (M + 1) |
|---|---|---|---|
| I-213 | | methyl 6-[1-(6-methoxypyrimidin-2-yl)-2-(6-methoxypyridin-2-yl)-2-(6-methylcarbonylamino-pyridin-3-yl)ethyl]pyridin-2-ylcarbamate (diastereomer A) | 513.2 |
| I-214 | | methyl 6-[1-(6-methoxypyrimidin-2-yl)-2-(6-methoxypyridin-2-yl)-2-(6-methylcarbonylamino-pyridin-3-yl)ethyl]pyridin-2-ylcarbamate (diastereomer B) | 513.2 |
| I-215 | | (±)-6-[1-(4-fluorophenyl)-2-(6-aminopyridin-3-yl)-2-(6-methoxypyridin-2-yl)ethyl]pyridin-2-amine (diastereomer A) | 416.2 |
| I-216 | | (±)-6-[1-(4-fluorophenyl)-2-(6-aminopyridin-3-yl)-2-(6-methoxypyridin-2-yl)ethyl]pyridin-2-amine (diastereomer B) | 416.2 |
| I-217 | | 2-{2,2-dipyridin-3-yl-1-[6-(pyrrolidin-1-ylcarbonyl)pyridin-2-yl]ethyl}-6-methoxypyridine | 466.20 |

-continued

| Example | Compound | Name | MS (M + 1) |
|---|---|---|---|
| I-218 | | N~2~-{4-[1-(3-cyanophenyl)-2,2-dipyridin-3-ylethyl]pyrimidin-2-yl}-N$^1$,N$^1$-dimethylglycinamide | 464.2 |
| I-219 | | 4-[1-(6-methoxypyridin-3-yl)-2,2-dipyridin-3-ylethyl]pyrimidin-2-amine | 385.1 |
| I-220 | | 4-[1-(6-methoxypyridin-3-yl)-2,2-dipyridin-3-ylethyl]pyrimidin-2-amine | 385.1 |
| I-221 | | N-{6-[1-(4-fluorophenyl)-2-(2-fluoropyridin-3-yl)-2-pyridin-3-ylethyl]pyridin-2-yl}methanesulfonamide | 467.2 |
| I-222 | | N-{6-[1-(4-fluorophenyl)-2-(2-fluoropyridin-3-yl)-2-pyridin-3-ylethyl]pyridin-2-yl}methanesulfonamide | 467.2 |

| Example | Compound | Name | MS (M + 1) |
|---|---|---|---|
| I-223 | | methyl 6-[1-(4-fluorophenyl)-2-(2-fluoropyridin-3-yl)-2-pyridin-3-ylethyl]pyridin-2-ylcarbamate | 447.2 |
| I-224 | | methyl 6-[1-(4-fluorophenyl)-2-(2-fluoropyridin-3-yl)-2-pyridin-3-ylethyl]pyridin-2-ylcarbamate | 447.2 |
| I-225 | | N-{6-[1-(6-methoxypyridin-3-yl)-2,2-dipyridin-3-ylethyl]pyridin-2-yl}methanesulfonamide | 462.2 |
| I-226 | | 6-[1-(6-methoxypyridin-2-yl)-2,2-dipyridin-3-ylethyl]-N-pyridin-2-ylpyridine-2-carboxamide | 489.2 |
| I-227 | | methyl 6-[1-(6-methoxypyridin-3-yl)-2,2-dipyridin-3-ylethyl]pyridin-2-ylcarbamate | 442.3 |

| Example | Compound | Name | MS (M + 1) |
|---|---|---|---|
| I-228 | | N-{6-[1-(3,4-dichlorophenyl)-2,2-dipyridin-3-ylethyl]pyridin-2-yl}methanesulfonamide | 499.2 |
| I-229 | | N-{6-[1-(4-chlorophenyl)-2,2-dipyridin-3-ylethyl]pyridin-2-yl}methanesulfonamide | 465.3 |
| I-230 | | N-(6-{2,2-dipyridin-3-yl-1-[4-(trifluoromethyl)phenyl]ethyl}pyridin-2-yl)methanesulfonamide | 499.2 |
| I-231 | | 4-[1-(4-chlorophenyl)-2,2-dipyridin-3-ylethyl]pyrimidin-2-amine | 388.3 |
| I-232 | | 4-[1-(6-aminopyridin-3-yl)-2,2-dipyridin-3-ylethyl]pyrimidin-2-amine bis(trifluoroacetate) | 370.2 |

| Example | Compound | Name | MS (M + 1) |
|---|---|---|---|
| I-233 | | N-{6-[1-(4-chlorophenyl)-2-(2-fluoropyridin-3-yl)-2-pyridin-3-ylethyl]pyridin-2-yl}methanesulfonamide | 483.2 |
| I-234 | | N-{6-[2-(2-fluoropyridin-3-yl)-1-(6-methoxypyridin-3-yl)-2-pyridin-3-ylethyl]pyridin-2-yl}methanesulfonamide | 480.3 |
| I-235 | | N-{6-[2-(2-fluoropyridin-3-yl)-1-(6-methoxypyridin-3-yl)-2-pyridin-3-ylethyl]pyridin-2-yl}methanesulfonamide | 480.3 |
| I-236 | | 4-[1-(4-chlorophenyl)-2,2-dipyridin-3-ylethyl]-n-methylpyrimidin-2-amine | 402.3 |
| I-237 | | N-{6-[1-(4-cyanophenyl)-2-(2-fluoropyridin-3-yl)-2-pyridin-3-ylethyl]pyridin-2-yl}methanesulfonamide | 474.3 |

-continued

| Example | Name | MS (M + 1) |
|---|---|---|
| I-238 | N-{6-[1-(4-cyanophenyl)-2-(2-fluoropyridin-3-yl)-2-pyridin-3-ylethyl]pyridin-2-yl}methanesulfonamide | 474.3 |
| I-239 | 4-[1-(6-chloropyridin-3-yl)-2,2-dipyridin-3-ylethyl]pyrimidine | 374.1 |
| I-240 | 4-(1,2,2-tripyridin-3-ylethyl)pyrimidine | 340.2 |
| I-241 | 4-[1-(2-aminopyrimidin-4-yl)-2,2-dipyridin-3-ylethyl]benzonitrile | 379.3 |
| I-242 | 4-[1-(2-aminopyrimidin-4-yl)-2,2-dipyridin-3-ylethyl]benzonitrile | 379.3 |

| Example | Compound | Name | MS (M + 1) |
|---|---|---|---|
| I-243 | | 5-(2,2-dipyridin-3-yl-1-pyrimidin-4-ylethyl)pyridin-2-amine | 355.3 |
| I-244 | | No name | 467.2 |
| I-245 | | 4-[1-(3,4-dichlorophenyl)-2,2-dipyridin-3-ylethyl]pyrimidin-2-amine | 422.1 |
| I-246 | | 4-{2,2-dipyridin-3-yl-1-[4-(trifluoromethyl)phenyl]ethyl}pyrimidin-2-amine | 422.1 |

-continued

| Example | Compound | Name | MS (M + 1) |
|---|---|---|---|
| I-247 | | 4-[1-(6-aminopyridin-2-yl)-2-(4-chlorophenyl)-2-pyridin-3-ylethyl]pyrimidin-2-amine | 403.1 |
| I-248 | | 4-[1-(6-aminopyridin-2-yl)-2-(4-chlorophenyl)-2-pyridin-3-ylethyl]pyrimidin-2-amine | 403.1 |
| I-249 | | methyl 6-[1-(2-aminopyrimidin-4-yl)-2-(4-chlorophenyl)-2-pyridin-3-ylethyl]pyridin-2-ylcarbamate | 461.1 |
| I-250 | | methyl 6-[1-(2-aminopyrimidin-4-yl)-2-(4-chlorophenyl)-2-pyridin-3-ylethyl]pyridin-2-ylcarbamate | 461.1 |

SCHEME II

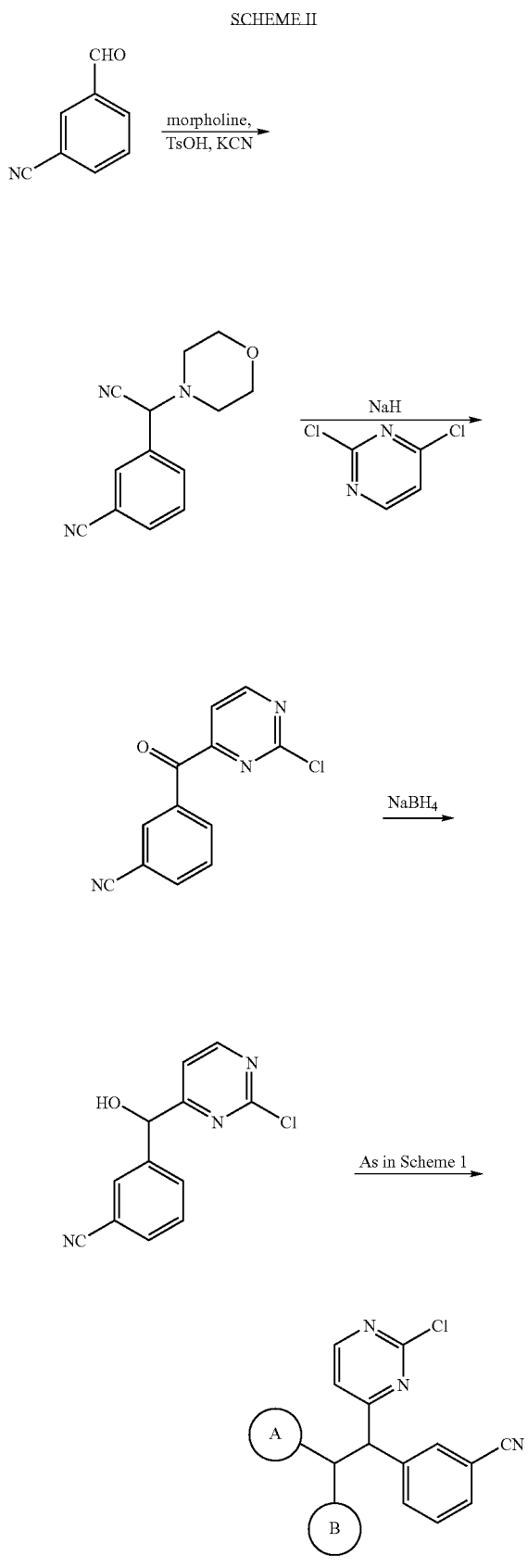

3-[(2-Chloropyrimidin-4-yl)(hydroxy)methyl]benzonitrile was prepared in accordance with Scheme II above and Steps A-C below, and this alcohol intermediate was converted to EXAMPLES II-1 to II-3 in accordance with Scheme I. Examples II-4 and II-5 were prepared in the same manner, substituting 2-chloropyrimidine for 2,4-dichloropyrimidine in Step B.

Step A

To 3-cyanobenzaldehyde (8.0 g, 61.0 mmol) was added morpholine (10.63 g, 122.0 mmol), p-toluenesulfonic acid (12.18 g, 64.05 mmol), and then a solution of potassium cyanide (3.97 g, 61.0 mmol) in 12mL water. The mixture was refluxed for 75 minutes then cooled to room temperature and partitioned between satd. sodium bicarbonate and methylene chloride. The aqueous portion was extracted with methylene chloride (1×), and the resulting organic portion washed with satd. sodium bisulfite (1×). The organic portion was dried over sodium sulfate and concentrated in vacuo. Crystallization from hot ethanol gave 3-[cyano(morpholin-4-yl)methyl]benzonitrile (11.83 g, 85%). LRMS m/z (M+H) Calcd: 228.3, found: 228.1.

Step B

3-[cyano(morpholin-4-yl)methyl]benzonitrile (5 g, 22.0 mmol) was dissolved in 175 mL dry DMF and cooled to 0° C. Add sodium hydride (Aldrich, 0.58 g, 24.2 mmol) in one portion and stir for 25 minutes at 0° C. Add 2,4-dichloropyrimidine (Aldrich, 9.83 g, 66.0 mmol) in one portion. After 10 minutes, additional sodium hydride (1.16 g, 48.4 mmol) was added in one portion and the bath allowed to warm to room temperature. After 15 h, the reaction was quenched with water and partitioned between ethyl acetate and saturated sodium bicarbonate. The aqueous portion was extracted with ethyl acetate (2×). The combined organic portion was dried over sodium sulfate and concentrated in vacuo. The crude material was taken up in 175 mL of 70% (v/v) acetic acid/water and refluxed for 45 min. The reaction mixture was cooled to room temperature, diluted with water, then extracted with ethyl acetate (2×). The combined organic portion was washed with saturated sodium bicarbonate (1×), dried over sodium sulfate, and concentrated in vacuo. The crude material was purified by silica gel chromatography (3-35% ethyl acetate in hexanes) and the product-containing fractions concentrated in vacuo to give 3-[(2-chloropyrimidin-4-yl)carbonyl]benzonitrile (3.0 g, 56%). LRMS m/z (M+H) Calcd: 244.7, found 244.0.

Step C

3-[(2-chloropyrimidin-4-yl)carbonyl]benzonitrile (3 g, 12.31 mmol) was dissolved in 90 mL dry methanol and cooled to 0 C. Sodium borohydride (Acros, 0.512 g, 13.54 mmol) was dissolved in 30 mL dry methanol and added slowly via syringe, and the reaction mixture stirred at 0 C for 100 min. Additional sodium borohydride (0.256 g, 6.77 mmol) was dissolved in 15 mL dry methanol and added via syringe. After 20 minutes the reaction mixture was diluted with methylene chloride and quenched with saturated sodium bicarbonate. The resulting mixture was partitioned between methylene chloride and saturated sodium bicarbonate. The aqueous portion was extracted with methylene chloride (3×), and the combined organic portion dried over sodium sulfate and concentrated in vacuo to give 3-[(2-chloropyrimidin-4-yl)(hydroxy)methyl]benzonitrile (2.9 g, 96%). LRMS m/z (M+H) Calcd: 246.7, found: 246.0.

EXAMPLES II-1-II-13

| | | | |
|---|---|---|---|
| II-1 | | (±)-N-{4-[1-(3-chlorophenyl)-2,2-dipyridin-3-ylethyl]pyrimidin-2-yl}methanesulfonamide | 466.1090 |
| II-2 | | (±)-N-{4-[1-(3-cyanophenyl)-2,2-dipyridin-3-ylethyl]pyrimidin-2-yl}methanesulfonamide | 457.1436 |
| II-3 | | (±)-3-[2-(6-aminopyridin-2-yl)-1-(2-aminopyrimidin-4-yl)-2-pyridin-3-ylethyl]benzonitrile<br>1:1 mixture of diastereomers | 394.1436 |
| II-4 | | (±)-2-[1-(3-chlorophenyl)-2,2-dipyridin-3-ylethyl]pyrimidine | 373.1217 |
| II-5 | | (±)-3-(2,2-dipyridin-3-yl-1-pyrimidin-2-ylethyl)benzonitrile | 364.1539 |
| II-6 | | N-{2-[1-(4-fluorophenyl)-2,2-dipyridin-3-ylethyl]pyrimidin-4-yl}methanesulfonamide | 450.1379 |

-continued
| | | | |
|---|---|---|---|
| II-7 | 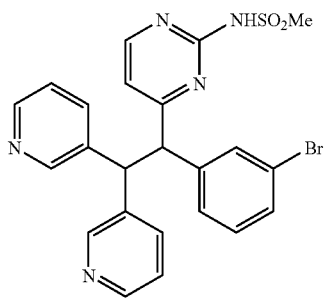 | N-{4-[1-(3-bromophenyl)-2,2-dipyridin-3-ylethyl]pyrimidin-2-yl}methanesulfonamide | 510.0576 |
| II-8 | 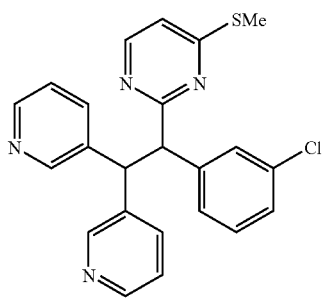 | 2-[1-(3-chlorophenyl)-2,2-dipyridin-3-ylethyl]-4-(methylthio)pyrimidine | 419.1092 |
| II-9 | 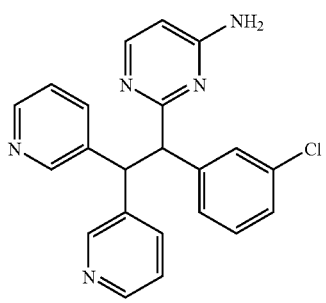 | 2-[1-(3-chlorophenyl)-2,2-dipyridin-3-ylethyl]pyrimidin-4-amine | 388.1 |
| II-10 | 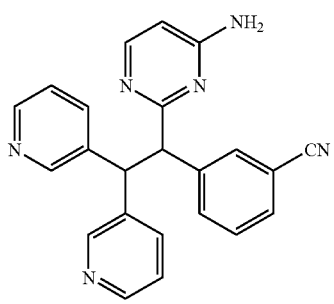 | 3-[1-(4-aminopyrimidin-2-yl)-2,2-dipyridin-3-ylethyl]benzonitrile | 379.1657 |
| II-11 | 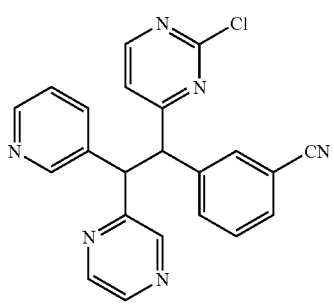 | 3-[1-(4-chloropyrimidin-2-yl)-2-pyrazin-2-yl-2-pyridin-3-ylethyl]benzonitrile | 399.1137 |

| | | | |
|---|---|---|---|
| II-12 | | 2-[2-(4-ammoniopyrimidin-2-yl)-2-(3-cyanophenyl)-1-pyridinium-3-ylethyl]pyrazin-1-ium tris(trifluoroacetate) | 380.1619 |
| II-13 | | 2-[2-(4-ammoniopyrimidin-2-yl)-2-(3-cyanophenyl)-1-pyridinium-3-ylethyl]pyrazin-1-ium tris(trifluoroacetate) | 380.1633 |

SCHEME III

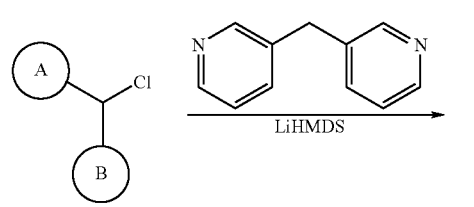

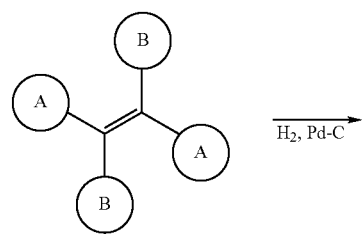

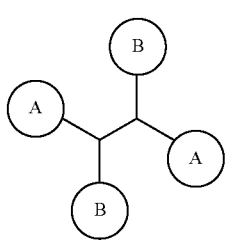

The variables A and B in the scheme are as defined in "Formula I".

EXAMPLE III-1

2,2',2'',2'''-Ethane-1,1,2,2-tetrayltetrapyridine

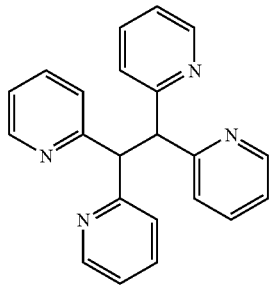

Step A

Cool a solution of bis(3-pyridyl)methane (128 mg) in 5 mL THF to −78 C. Add LiHMDS (0.753 mL of a 1 M solution in THF) and stir at −78 C. for 1.25 h. Add a solution of 4-chloro-2-[chloro(pyridin-2-yl)methyl]pyridine (150 mg, see Scheme 1) in 2 mL THF via cannula. Stir 3 min at −78 C., then warm to 0 C. and stir for 1 h. Remove ice bath and stir for 20 h at ambient temperature. Quench with sat $NH_4Cl$, partition between $CH_2Cl_2$ and bicarb, and extract the aqueous solution once more with $CH_2Cl_2$. Dry the combined organic solutions over $Na_2SO_4$ and concentrate. Flash chromatography (0-8% MeOH-$NH_3$/$CH_2Cl_2$) gave a tan oil, which was further purified by reverse phase HPLC to give 109 mg of a 2:1 mixture of the pictured olefin isomers.

Step B

The above mixture of olefin isomers (40 mg) was combined with a suspension of 10% Pd-C (10 mg) in ~1 mL of 95% EtOH. The mixture was purged with Ar, then purged briefly with $H_2$ and stirred under an $H_2$ balloon for 8 h at room temperature. The balloon was removed, and the reaction was flushed with Argon. Filtration through celite, rinsing with EtOH, and concentration gave a residue that was purified by reverse phase HPLC to give the titled compound. HRMS [M+H] $C_{22}H_{18}N_4$, found 339.1614.

The following compounds were made in accordance with Scheme III, and were isolated as products of Step B above.

EXAMPLES III-2-III-3

| Example | Compound | Name | MS (M + 1) |
|---|---|---|---|
| III-2 | | (±)-4-chloro-2-(1,2,2-tripyridin-2-ylethyl)pyridine | 373.1222 |
| III-3 | | 4-chloro-2-[2-(4-chloropyridin-2-yl)-1,2-dipyridin-2-ylethyl]pyridine 1:1 mixture dl:meso | 407.0823 |

SCHEME IV

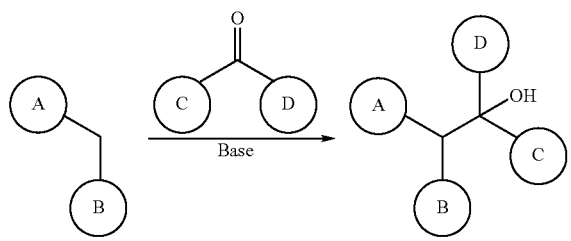

EXAMPLE IV-1

(±)-1,2,2-tripyridin-3-yl-1-pyrimidin-4-ylethanol

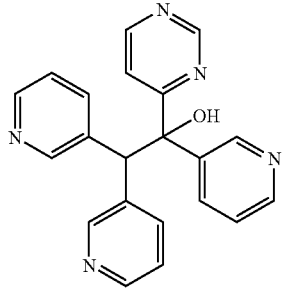

In a flame dried flask under $N_2$, diisopropylamine (0.079 mL, 0.56 mmol) was dissolved in THF (1 mL). The solution was cooled to 0° C. n-Butyl-lithium (2.5 M solution in hexanes, 0.215 mL, 0.54 mmol) was slowly added and the reaction was stirred at 0° C. for 15 min. A solution of 3-(pyridin-3-ylmethyl)pyridine (0.087 g, 0.51 mmol) in THF (1mL) was slowly added drop-wise. The reaction became dark red. After 10 min. a solution of pyridin-3-yl(pyrimidin-4-yl)methanone (0.099 g, 0.54 mmol, *J. Heterocyclic Chem.*, 34, 17 (1997)) in THF (1 mL) was slowly added drop-wise. The reaction was stirred at 0° C. for 3 hr then removed from the ice bath. Sat. aq. $NH_4Cl$ (20 mL) was added and the reaction was stirred vigorously. The product was extracted with EtOAc (4×50 mL). The combined organics were dried over $Na_2SO_4$, filtered and concentrated to afford an oil which was purified by reverse phase HPLC (5-95% $CH_3CN/H_2O$+0.05% $NH_4OH$). The fractions were combined and concentrated in vacuo to afford the title compound as a white solid. $^1H$ NMR ($CDCl_3$) δ 9.01 (d, 1H, J=1.22 Hz), 8.85 (d, 1H, J=1.95 Hz), 8.70 (d, 1H, J=5.37 Hz), 8.58 (d, 1H, J=2.19 Hz), 8.42 (dd, 1H, J=1.46 Hz), 8.38-8.33 (m, 3H), 7.94-7.87 (m, 2H), 7.70-7.67 (m, 1H), 7.07 (dd, 1H, J=1.22 Hz), 7.19-7.14 (m, 1H), 7.13-7.08 (m, 2H), 5.98 (s, 1H), 5.12 (s, 1H). HRMS m/z (M+H) Calculated: 356.1506, found: 356.1519.

The following compounds were made in accordance with Scheme IV, where intermediates in the scheme were modified according to literature methods.

EXAMPLES IV-2-V-4

| Example | Compound | Name | MS (M + 1) |
|---|---|---|---|
| IV-2 | | 1-phenyl-2,2-dipyridin-3-yl-1-pyrimidin-2-ylethanol | 355.1550 |

155
-continued

| Example | Compound | Name | MS (M + 1) |
|---|---|---|---|
| IV-3 | 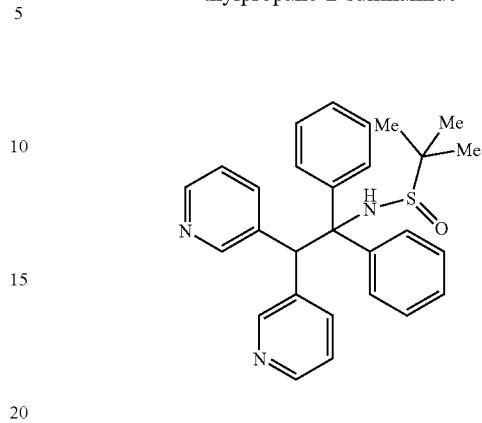 | 1,2,2-tripyridin-3-yl-1-pyrimidin-2-ylethanol | 356.1510 |
| IV-4 | | 1,1-diphenyl-2,2-dipyridin-3-ylethanol | 353.2 |

SCHEME V

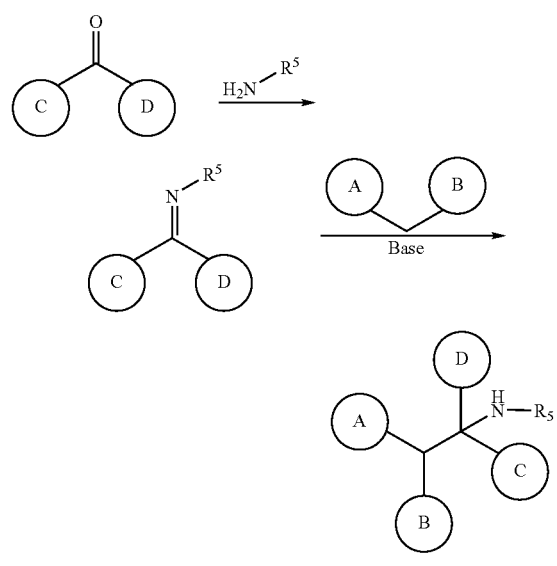

156

EXAMPLE V-1

(S)-N-(1,1-diphenyl-2,2-dipyridin-3-ylethyl)-2-methylpropane-2-sulfinamide

Step A

In a flame dried flask under $N_2$, benzophenone (0.514 g, 2.82 mmol) was dissolved in anhydrous dioxane (5 mL). Ti(IV) ethoxide (1.479 mL, 7.05 mmol) was added followed by (S)-(−)-2-methyl-2-propanesulfinamide (0.376 g, 3.10 mmol). The rxn was heated to 105° C. After 4.5 hr the reaction was cooled to RT and brine (15 mL) was added. A precipitate formed and the reaction was rapidly stirred for 10 min. The suspension was filtered through celite and the filter cake was washed with brine and ethyl acetate. The layers of the filtrate were separated. The organic layer was dried over $Na_2SO_4$, filtered, and concentrated in vacuo to afford a yellow oil. The oil was purified by flash column chromatography (90:10 hexanes/ethyl acetate). The fractions were combined and concentrated in vacuo to afford (S)-N-(diphenylmethylene)-2-methylpropane-2-sulfinamide as a light yellow oil. $^1$H NMR ($CDCl_3$) δ 7.51-7.43 (broad m, 10H), 1.30 (s, 9H). [M+H]+=286.1.

Step B

In a flame dried flask under $N_2$, 3-(pyridin-3-ylmethyl) pyridine (0.072 g, 0.42 mmol) was dissolved in THF (3 mL). The solution was cooled to 0° C. Lithium bis(trimethylsilyl)-amide (1 M solution in THF, 0.465 mL, 0.47 mmol) was slowly added and the reaction was stirred at 0° C. for 15 min. The reaction became dark red. A solution of N-(diphenylmethylene)-2-methylpropane-2-sulfinamide (0.121 g, 0.42 mmol) in THF (1 mL) was slowly added drop-wise. The reaction was stirred at 0° C. for 1 hr then removed from the ice bath. Sat. aq. $NH_4Cl$ (20 mL) was added and the reaction was stirred vigorously. The product was extracted with EtOAc (3×50 mL). The combined organics were dried over $Na_2SO_4$, filtered and concentrated to afford an oil which was purified by flash column chromatography (0-5% MeOH/$CH_2Cl_2$). The fractions were combined and concentrated in vacuo to afford the title compound as a white solid. (S) Enantiomer at Sulfur: $^1$H NMR ($CD_3OD$) δ 8.49 (d, 1H, J=2.20 Hz), 8.46 (dd, 1H, J=1.46 Hz), 8.36 (dd, 1H, J=5.37 Hz), 8.30 (d, 1H, J=2.20 Hz), 7.49-7.33 (m, 11H), 7.25-7.23 (m, 3H), 5.78 (s, 1H), 1.08 (s, 1H ). HRMS m/z (M+H) found: 478.1920 (M+Na).

SCHEME VI

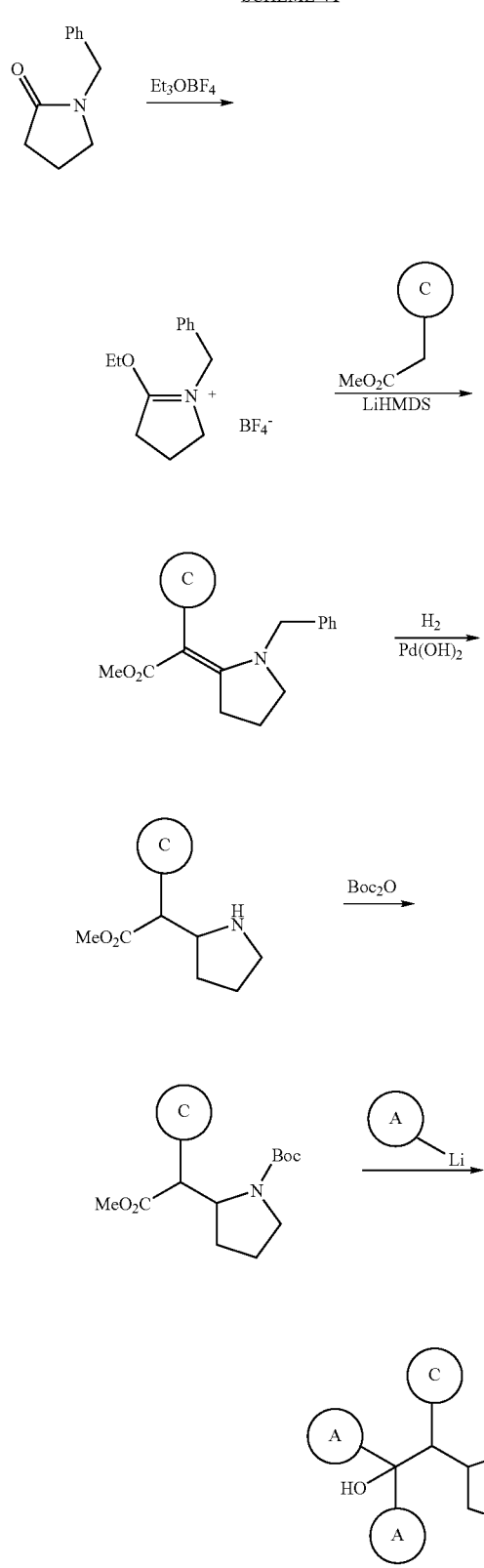

The variables C and A in the scheme are as defined in "Formula I".

EXAMPLE VI-1

(±)-tert-Butyl 2-(2-hydroxy-1-phenyl-2,2-dipyridin-3-ylethyl)pyrrolidine-1-carboxylate (diastereomer A)

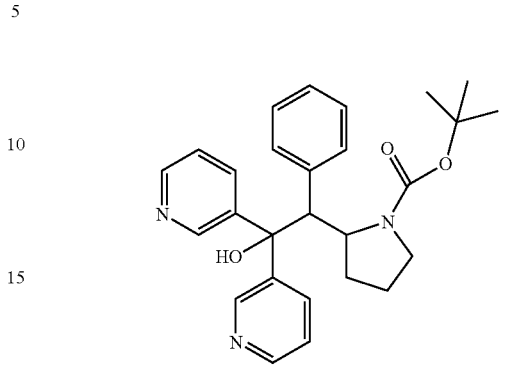

Step A:

To a solution of N-benzylpyrrolidinone (2.18 g, 12.4 mmol) in 25 mL of ether was added at 0° C. triethyloxonium tetrafluoroborate (2.15 g, 11.3 mmol). The reaction was allowed to warm to ambient temperature and stir for 30 minutes, during which a solid product precipitated from the reaction. The ether was decanted off, and the remaining residue washed three times with ether. Residual solvent was removed in vacuo to provide 1-benzyl-5-ethoxy-3,4-dihydro-2H-pyrrolium tetrafluoroborate.

Step B:

Lithium hexamethyldisilazide solution (8.39 mL of 1M in tetrahydrofuran, 8.39 mmol) was added to dry THF and cooled to −78° C. Methyl phenylacetate (1.15 mL, 7.99 mmol) was added dropwise, and the reaction stirred for 15 minutes. A solution of 1-benzyl-5-ethoxy-3,4-dihydro-2H-pyrrolium tetrafluoroborate in 5 mL of tetrahydrofuran was added dropwise, and after one hour the reaction was allowed to warm to room temperature. The mixture was quenched with saturated $NaHCO_3$ solution, warmed to ambient temperature and poured into water. The aqueous layer was extracted with EtOAc and the organic extract was washed with brine, dried with $Na_2SO_4$, filtered and concentrated in vacuo. The residue was purified by silica gel chromatography (25-30% EtOAc/hexane), providing methyl 2-(1-benzylpyrrolidin-2-ylidene)(phenyl)acetate. ESI+MS: 308.3 $[M+H]^+$.

Step C:

To a solution of methyl 2-(1-benzylpyrrolidin-2-ylidene)(phenyl)acetate (0.505 g, 1.64 mmol) in 5 mL of methanol was added palladium(II) hydroxide (231 mg, 1.64 mmol), and the reaction was stirred under a balloon of hydrogen gas. After 3 days, the mixture was filtered through celite, the pad was rinsed with $CH_2Cl_2$/MeOH, and the filtrate was concentrated in vacuo to provide methyl phenyl(pyrrolidin-2-yl)acetate as a mixture of two diastereomers. ESI+MS: 220.2 $[M+H]^+$.

Step D:

To a solution of methyl phenyl(pyrrolidin-2-yl)acetate (0.360 g, 1.64 mmol) in 5 mL of tetrahydrofuran was added di-tert-butyl dicarbonate (717 mg, 3.28 mmol), and the reaction was stirred overnight. The mixture was concentrated in vacuo, then purified by silica gel chromatography (20% EtOAc/hexane), to provide tert-butyl 2-(2-methoxy-2-oxo-1-phenylethyl)pyrrolidine-1-carboxylate. ESI+MS: 264.2 $[M+H-isobutylene]^+$.

Step E:

3-Bromopyridine (0.790 mL, 8.20 mmol) was dissolved in 30 mL of dry Et$_2$O and was cooled to −78° C. n-Butyl lithium (3.28 mL, 2.5M solution in hexanes, 8.20 mmol) was added dropwise via syringe over 10 minutes. After stirring for 15 minutes, a solution of tert-butyl 2-(2-methoxy-2-oxo-1-phenylethyl)pyrrolidine-1-carboxylate (0.524 g, 1.64 mmol) in 5 mL of ether was added dropwise. The reaction was stirred for 45 minutes at −78° C., quenched with saturated aqueous NaHCO$_3$ solution and poured into saturated aqueous NaHCO$_3$ solution and EtOAc. The organic layer was extracted with brine, dried Na$_2$SO$_4$, filtered and concentrated in vacuo. The residue was purified by preparative reverse-phase HPLC, and the combined pure fractions were partitioned between CH$_2$Cl$_2$ and saturated aqueous NaHCO$_3$ solution. Concentration of the organic fraction provided a single diastereomer of the titled compound. $^1$H NMR (500 MHz, CDCl$_3$): δ 9.03 (br s, 1H), 8.56 (br s, 1H), 8.52 (d, J=4.4 Hz, 1H), 8.18 (d, J=8.3 Hz, 1H), 8.15 (d, J=4.4 Hz, 1H), 7.75 (d, J=7.8 Hz, 1H), 7.43 (br s, 1H), 7.36 (dd, J=7.8 and 4.8 Hz, 1H), 7.06-7.12 (m, 4H), 7.02 (dd, J=7.8 and 4.8 Hz, 1H), 5.1 (br s, 1H), 4.28 (d, J=6.6 Hz, 1H), 3.93 (s, 1H), 3.22 (m, 1H), 2.25 (m, 1H), 2.17 (m, 1H), 1.96 (m, 1H), 1.50 (m, 9H), 1.30 (m, 1H). HRMS [M+H] C$_{27}$H$_{32}$N$_3$O$_3$ calcd 446.2438, found 446.2424.

The following compounds were made according to Scheme VI, where intermediates in the scheme were modified according to literature methods. Example VI-2 was prepared by acid deprotection of carbamate VI-1. Acetylation of VI-2 using acetic anhydride gave VI-3. Examples VI-4 and VI-5 were made from N-methylpyrrolidinone in accordance with the Scheme, omitting the Boc protection step.

EXAMPLES VI-2-VI-5

| Example | Compound | Name | MS (M + 1) |
|---|---|---|---|
| VI-2 | | (±)-2-phenyl-1,1-dipyridin-3-yl-2-pyrrolidin-2-ylethanol (diastereomer A) | 346.1902 |
| VI-3 | | (±)-2-(1-acetylpyrrolidin-2-yl)-2-phenyl-1,1-dipyridin-3-ylethanol (diastereomer A) | 388.2009 |
| VI-4 | | (±)-2-(4-fluorophenyl)-2-(1-methylpyrrolidin-2-yl)-1,1-dipyridin-3-ylethanol (diastereomer A) | 378.1974 |
| VI-5 | | (±)-2-(4-fluorophenyl)-2-(1-methylpyrrolidin-2-yl)-1,1-dipyridin-3-ylethanol (diastereomer B) | 378.1976 |

SCHEME VII

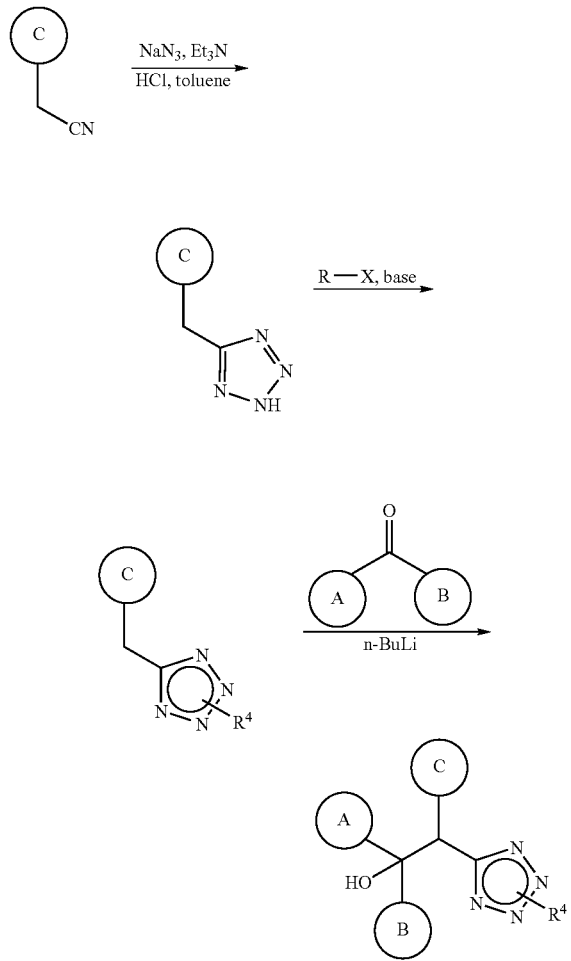

The variables A, B, C and R⁴ in the scheme are as defined in "Formula I". X is a leaving group, such as a halide.

EXAMPLE VII-1

(±)-2-(4-fluorophenyl)-2-(2-methyl-2H-tetrazol-5-yl)-1,1-dipyridin-3-ylethanol

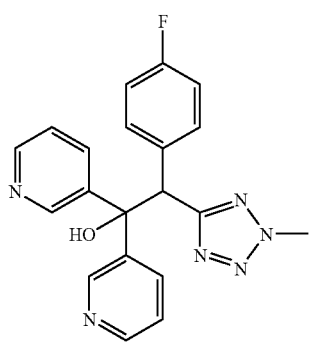

Step A:

To a solution of (4-fluorophenyl)acetonitrile (5.00 g, 37.0 mmol) in 100 mL of toluene was added sodium azide (7.22 g, 111 mmol), triethylamine (15.5 mL, 111 mmol), and concentrated aqueous HCl solution (9.25 mL, 111 mmol). The reaction was heated at 90° C. overnight. The solution was cooled to room temperature and extracted with water and 1N NaOH solution. The combined aqueous layers were washed with ether (3×), acidified with concentrated aqueous HCl solution, and the resulting precipitate was collected by filtration and rinsed with 0.1N HCL solution. The resulting solid was azeotroped from toluene to provide 5-(4-fluorobenzyl)-2H-tetrazole. ESI+MS: 178.9 [M+H]⁺.

Step B:

To a solution of 5-(4-fluorobenzyl)-2H-tetrazole (0.500 g, 2.81 mmol) in 10 mL of acetonitrile was added N,N-diisopropylethylamine (9.8 mL, 56 mmol) and iodomethane (0.227 mL, 3.65 mmol). The solution was subjected to microwave irradiation at 60° C. for two hours, then cooled to room temperature. The mixture was partitioned between water and EtOAc, and the organic layer was extracted with 1N NaOH solution and brine. The organic layer was dried (Na₂SO₄), filtered and concentrated in vacuo to provide a 1:1 mixture of 5-(4-fluorobenzyl)-2-methyl-2H-tetrazole and 5-(4-fluorobenzyl)-1-methyl-1H-tetrazole, which was azeotroped from toluene before use in the next reaction. ESI+MS: 193.2 [M+H]⁺ for both isomers.

Step C:

To a 1:1 mixture of 5-(4-fluorobenzyl)-2-methyl-2H-tetrazole and 5-(4-fluorobenzyl)-1-methyl-1H-tetrazole, (0.209 g, 1.09 mmol) in 10 mL of 1:1 ether:tetrahydrofuran at −78° C. was added dropwise n-BuLi (0.434 mL of 2.5 M in hexane, 1.09 mmol). After stirring for one hour, a solution of dipyridin-3-ylmethanone (200 mg, 1.09 mmol) in 3 mL of tetrahydrofuran was added dropwise. Afterh 30 minutes, the reaction was quenched by transferring it via cannula to a −78° C. solution of 100 mL of ether containing 1 mL of concentrated aqueous HCl solution. After concentrating the mixture in vacuo, the resulting residue was taken up in EtOAc and extracted with 10% aqueous Na₂CO₃ solution and brine, dried (Na₂SO₄), filtered and concentrated in vacuo. The residue was purified by preparative reverse-phase HPLC to provide the titled compound, along with a regioisomer (Example VII-4). $^1$H NMR (500 MHz, d₆-DMSO): δ 8.91 (br s, 1H), 8.66 (br s, 1H), 8.36 (d, J=4.4 Hz, 1H), 8.24 (d, J=4.4 Hz, 1H), 8.07 (br d, J=8.3 Hz, 1H), 7.82 (br d, J=8.0 Hz, 1H), 7.51 (dd, J=8.7 and 5.6 Hz, 2H), 7.29 (dd, J=8.3 and 4.9 Hz, 1H), 7.16 (dd, J=8.0 and 4.6 Hz, 1H), 6.95 (t, J=9.0 Hz, 2H), 6.16 (s, 1H), 6.05 (s, 1H), 4.23 (s, 3H). HRMS [M+H] C₂₀H₁₈FN₆O calcd 377.1521, found 377.1527.

The following compounds were made according to Scheme VII, where intermediates in the scheme were modified according to literature methods. Example VII-2 was prepared by acid deprotection of 2-phenyl-1,1-dipyridin-3-yl-2-(2-trityl-2H-tetrazol-5-yl)ethanol.

EXAMPLES VII-2-VII-6

| Example | Compound | Name | MS (M + 1) |
|---|---|---|---|
| VII-2 | | (±)-2-phenyl-1,1-dipyridin-3-yl-2-(2H-tetrazol-5-yl)ethanol | 345.1468 |
| VII-3 | | (±)-2-(2-methyl-2H-tetrazol-5-yl)-2-phenyl-1,1-dipyridin-3-ylethanol | 359.1630 |
| VII-4 | | (±)-2-(4-fluorophenyl)-2-(1-methyl-1H-tetrazol-5-yl)-1,1-dipyridin-3-ylethanol | 377.1526 |
| VII-5 | | (±)-2-(1-ethyl-1H-tetrazol-5-yl)-2-(4-fluorophenyl)-1,1-dipyridin-3-ylethanol | 391.1683 |
| VII-6 | | (±)-2-(2-ethyl-2H-tetrazol-5-yl)-2-(4-fluorophenyl)-1,1-dipyridin-3-ylethanol | 391.1688 |

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward $K^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K⁺ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the 10$^{th}$ pulse than for the 1$^{st}$ pulse of the train. A Kv1.5 blocker may exhibit both use-dependence and rate-dependence.

A Kv1.5 blocker may also be identified through electrophysiological studies of native $I_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135,2003) and Schroeder et al. (J. of Biomol. Screen., 8(1);50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 µg/ml streptomycin, 1000 µg/ml G-418 sulfate. Cells are subcultured by treatment with Versene, then suspended in phosphate-buffered saline (PBS) and centrifuged. The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxylethylpiperazine-N$^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, K$_3$PO$_4$ 1.47, MgCl$_2$ 0.50, NaCl 138, Na$_3$PO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 µL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 µm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the 27$^{th}$ depolarization to +40 mV (in the 5 Hz train) is plotted as a function of antagonist concentration. The concentrations of drug required to inhibit current by 50% (IC$_{50}$) are determined by fitting of the Hill equation to the concentration response data: % of Control=100× $(1+([\text{Drug}]/\text{IC}_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the 1$^{st}$ depolarization to +40 mV minus the pre-compound mean current amplitude during the 27$^{th}$ depolarization to +40 mV)
4) peak current (maximum current amplitude during the 27$^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide ≧20% inhibition at a concentration of 33 µM or less in the high throughput Kv1.5 planar patch clamp assay described above.

Atomic Absorption Spectroscopy Protocol:

This assay identifies agents that specifically block the human Kv1.5 K+ channel heterologously expressed in CHO cells as measured by Rb⁺ efflux using Flame Atomic Absorption Spectroscopy (FAAS). The application of FAAS for measuring ion channel activity was adapted from Terstappen et al, *Anal. Biochem.*, 272:149-155, 1999.

CHO cells expressing human Kv1.5 are cultured as described above, then harvested with trypsin-EDTA and washed with medium.

1. 40,000 cells per well are seeded in a 96-well cell culture plate (assay plate) and the cells are allowed to grow for 48 hours at 37° C.
2. The medium is removed and 200 µl of Rb Load Buffer (Aurora Biomed, Vancouver, BC) is added for 3 hours at 37° C. under 5% CO$_2$.
3. The cells are washed 5 times with 200 µl Hank's Balanced Salt Solution (HBSS) followed by the addition of 100 µl HBSS containing test compound or 0.5% DMSO.

4. After 10 min, 100 µl of HEPES-buffered saline containing 140 mM KCl is added and plate is incubated at RT for 5 min. with gentle shaking.
5. Immediately thereafter, 150 µl of supernatant is transferred to a fresh 96 well plate and the remaining supernatant aspirated.
6. 120 µl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1-(A-B)/(C-B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 µM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Compounds of the invention may optionally be administered to a patient in need of Kv1.5 inhibition by means of coronary stent placement in the patient. The stent may include the compound by any standard means known to persons skilled in the art, e.g., coating or other means for associating the compound to the stent surface, or impregnating the compound into the stent. Such stents may be used in both intrapericardial administration and intracardiac administration by means of a catheter or other device that monitors rhythm.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylnaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppresant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, SHT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:

1. A compound of formula I, or a pharmaceutically acceptable salt thereof, having the formula I:

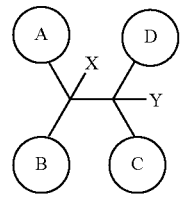

I wherein:
A and B are independently selected from the group consisting of
a pyridyl ring, wherein the point of attachment to the pyridyl ring is a carbon atom,
wherein said pyridyl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable N pyridyl ring atom is unsubstituted or substituted with oxo, said pyridyl ring $R^4$ substitutions being on one or more pyridyl ring carbon atoms
C is a phenyl ring, wherein said phenyl ring is unsubstituted, mono-substituted with $R^4$, disubstituted with groups independently selected from $R^4$, trisubstituted with groups independently selected from $R^4$, or tetrasubstituted with groups independently selected from $R^4$;
D is selected from the group consisting of:
a heteroaryl ring, wherein the point of attachment to the heteroaryl ring is a carbon atom, and the heteroaryl ring is selected from the group consisting of: a 4-6 membered saturated heterocyclic ring with 1, 2 or 3 heteroatom ring atoms selected from the group consisting of N, O and S, wherein the point of attachment to the heterocyclic ring is a carbon atom,
wherein said heteroaryl or saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;
X and Y are independently selected from the group consisting of H and $OR^5$ and $—NHS(O)R^5$;
$R^a$, in each instance in which it appears, is independently selected from the group consisting of
1) hydrogen,
2) $C_1$-$C_6$ alkyl,
3) halogen,
4) aryl,
5) heterocycly,
6) $C_3$-$C_{10}$ cycloalkyl, and
7) $OR^5$,
said alkyl, aryl, heterocyclyl and cycloalkyl is unsubstituted or substituted with at least one substituent selected from $R^6$,
$R^4$, in each instance in which it appears, is independently selected from the group consisting of
1) hydrogen,
2) halogen, 3) NO$_2$,
4) CN,
5) CR$^4$=C(R$^5$)$_2$,
6) C≡CR$^5$,
7) (CR$^a_2$)$_n$OR$^5$,
8) (CR$^a_2$)$_n$N(R$^5$)$_2$,
9) (CR$^a_2$)$_n$C(O)R$^5$,
10) (CR$^a_2$)$_n$C(O)OR$^5$,
11) (CR$^a_2$)$_n$R$^5$,
12) (CR$^a_2$)$_n$S(O)mR$^5$,
13) (CR$^a_2$)$_n$S(O)$_m$N(R$^5$)$_2$,
14) OS(O)$_m$R$^5$,
15) N(R$^5$)C(O)R$^5$,
16) N(R$^5$)S(O)$_m$R$^5$,
17) (CR$^a_2$)$_n$N(R$^6$)R$^5$,
18) (CR$^a_2$)$_n$N(R$^5$)(CR$^a_2$)$_n$C(O)N(R$^5$)$_2$,
19) (CR$^a_2$)$_n$N(R$^5$)(CR$^a_2$)$_n$C(O)OR$^5$,
20) N(R$^5$)(CR$^a_2$)$_n$R$^5$,
21) N(R$^5$)(CR$^a_2$)$_n$N(R$^5$)$_2$,
22) (CR$^a_2$)$_n$C(O)N(R$^5$)$_2$,
23) N$_3$, and
22) =O;

R$^5$, in each instance in which it appears, is independently selected from the group consisting of
1) hydrogen,
2) unsubstituted or substituted C$_1$-C$_6$ alkyl,
3) unsubstituted or substituted C$_3$-C$_{10}$ cycloalkyl,
4) unsubstituted or substituted aryl,
5) unsubstituted or substituted heterocycle,
6) CF$_3$,
7) unsubstituted or substituted C$_2$-C$_6$ alkenyl, and
8) unsubstituted or substituted C$_2$-C$_6$ alkynyl,
or in the case where R$^5$ is attached to a nitrogen atom that is disubstituted with R$^5$, each R$^5$ is independently selected from C$_1$-C$_6$ alkyl, and the nitrogen atom together with each R$^5$ form a ring;

R$^6$, in each instance in which it appears, is independently selected from the group consisting of
1) hydrogen,
2) unsubstituted or substituted C$_1$-C$_6$ alkyl,
3) halogen,
4) OR$^5$,
5) CF$_3$,
6) unsubtituted or substituted aryl,
7) unsubstituted or substituted C$_3$-C$_{10}$ cycloalkyl,
8) unsubstituted or substituted heterocycle,
9) S(O)$_m$N(R$^5$)$_2$,
10) C(O)OR$^5$,
11) C(O)R$^5$,
12) CN,
13) C(O)N(R$^5$)$_2$,
14) N(R$^5$)C(O)R$^5$,
15) N(R$^5$)C(O)OR$^5$,
16) N(R$^5$)C(O)N(R$^5$)$_2$,
17) OC(O)N(R$^5$)$_2$,
18) S(O)$_m$R$^5$,
19) OS(O)$_m$R$^5$,
20) NO$_2$, and
21) N(R$^5$)$_2$;

m is independently 0, 1 or 2; and
n is independently 0, 1, 2, 3, 4, 5 or 6.

2. A compound of claim 1, or a pharmaceutically acceptable salt thereof, wherein:
A is a pyridyl ring, wherein the point of attachment to the pyridyl ring is a carbon atom
wherein said pyridyl ring is unsubstituted, mono-substituted with R$^4$, disubstituted with groups independently selected from R4, trisubstituted with groups independently selected from R$^4$, or tetrasubstituted with groups independently selected from R$^4$, and wherein any stable N pyridyl ring atom is unsubstituted or substituted with oxo, said pyridyl ring R$^4$ substitutions being on one or more pyridyl ring carbon atoms;

B is a pyridyl ring, wherein the point of attachment to the pyridyl ring is a carbon atom, and the heteroaryl ring is selected from the group consisting of:
wherein said pyridyl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable N pyridyl ring atom is unsubstituted or substituted with oxo, said pyridyl ring R$^4$ substitutions being on one or more pyridyl ring carbon atoms;

C a phenyl ring,
wherein said phenyl ring is unsubstituted, mono-substituted with R$^4$, disubstituted with groups independently selected from R$^4$, trisubstituted with groups independently selected from or tetrasubstituted with groups independently selected from R$^4$;

D is selected from the group consisting of:
1) a heteroaryl ring, wherein the point of attachment to the heteroaryl ring is a carbon atom, and the heteroaryl ring is selected from the group consisting of:
a) a 5-membered unsaturated monocyclic ring with 1, 2, 3, or 4 heteroatom ring atoms selected from the group consisting of N, O or S, and
b) a 6-membered unsaturated monocyclic ring with 1, 2, 3, or 4 heteroatom ring atoms selected from the group consisting of N, O or 5, and
2) a 5-membered saturated heterocyclic ring with 1, 2 or 3 heteroatom ring atoms selected from the group consisting of N, O and S, wherein the point of attachment to the heterocyclic ring is a carbon atom,
wherein said heteroaryl or saturated heterocyclic ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable S or N heteroaryl or heterocyclic ring atom is unsubstituted or substituted with oxo, said heteroaryl ring R$^4$ substitutions being on one or more heteroaryl ring carbon atoms; and X and Y are independently selected from the group consisting of H, OR$^5$, and —NHS(O)R$^5$.

3. A compound of claim 2, or a pharmaceutically acceptable salt thereof, wherein
A is a pyridyl ring, wherein the point of attachment to the pyridyl ring is a carbon atom,
wherein said pyridyl ring is unsubstituted, mono-substituted with R$^4$, disubstituted with groups independently selected from R$^4$, trisubstituted with groups independently selected from R$^4$, or tetrasubstituted with groups independently selected from R$^4$, and wherein any stable N pyridyl ring atom is unsubstituted or substituted with oxo, said heteroaryl ring R$^4$ substitutions being on one or more heteroaryl ring carbon atoms;
B is a pyridyl ring, wherein the point of attachment to the pyridyl ring is a carbon atom, wherein said pyridyl ring is unsubstituted, mono-substituted with R⁴, disubstituted with groups independently selected from R⁴, trisubstituted with groups independently selected from R⁴, or tetrasubstituted with groups independently selected from R⁴, and wherein any stable N pyridyl ring atom is unsubstituted or substituted with oxo, said pyridyl ring R⁴ substitutions being on one or more pyridyl ring carbon atoms;

C is a phenyl ring
wherein said phenyl ring is unsubstituted, mono-substituted with R⁴, disubstituted with groups independently selected from R⁴, trisubstituted with groups independently selected from R⁴, or tetrasubstituted with groups independently selected from R⁴, ; and D is selected from the group consisting of:
1) a heteroaryl ring, wherein the point of attachment to the heteroaryl ring is a carbon atom, and the heteroaryl ring is selected from the group consisting of:
   a) a 5-membered unsaturated monocyclic ring with 4 N ring atoms, and
   b) a 6-membered unsaturated monocyclic ring with 1 or 2 N ring atoms, and
2) a 5-membered saturated heterocyclic ring with I N ring atom, wherein the point of attachment to the heterocyclic ring is a carbon atom,
wherein said heteroaryl or saturated heterocyclic ring is unsubstituted, mono-substituted with R⁴, disubstituted with groups independently selected from R⁴, trisubstituted with groups independently selected from R⁴, or tetrasubstituted with groups independently selected from R⁴, and wherein any stable N heteroaryl or heterocyclic ring atom is unsubstituted or substituted with oxo, said heteroaryl ring R⁴ substitutions being on one or more heteroaryl ring carbon atoms.

4. A compound of claim 3, or a pharmaceutically acceptable salt thereof, wherein
X is selected from the group consisting of hydrogen and —OH;
Y is selected from the group consisting of hydrogen, —OH and —NHS(O)C(CH₃)₃;
A is selected from the group consisting of

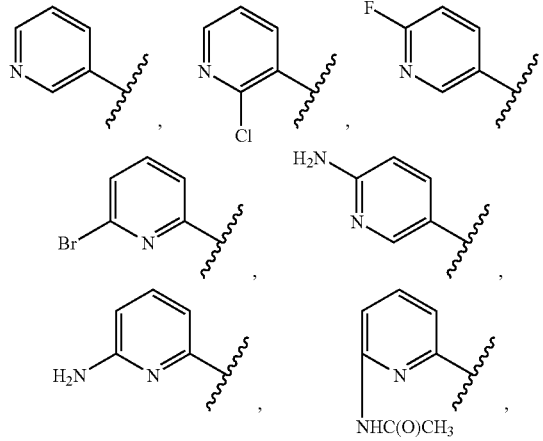

B is selected from the group consisting of

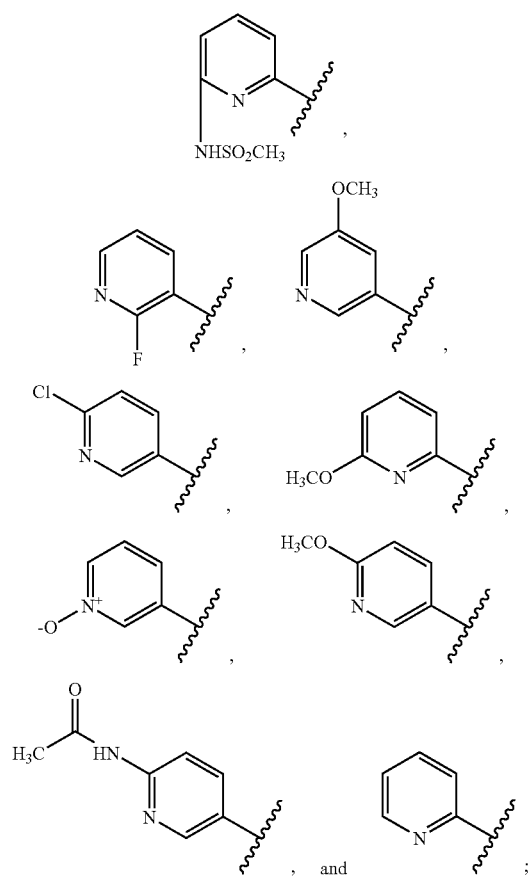

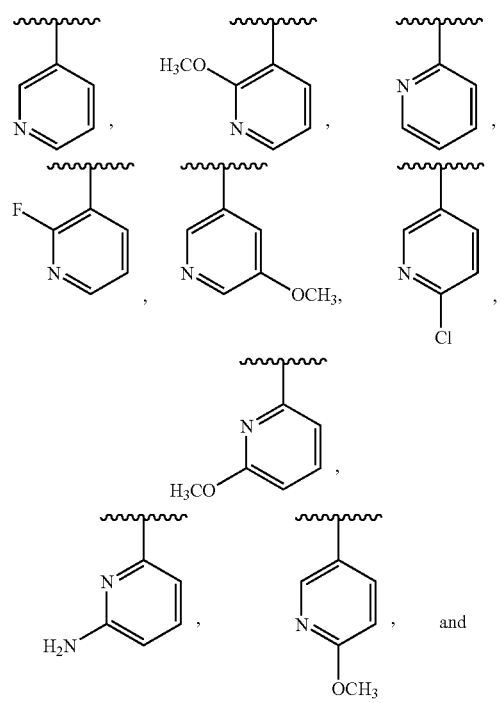

-continued
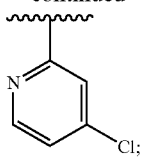
C is selected from the group consisting of
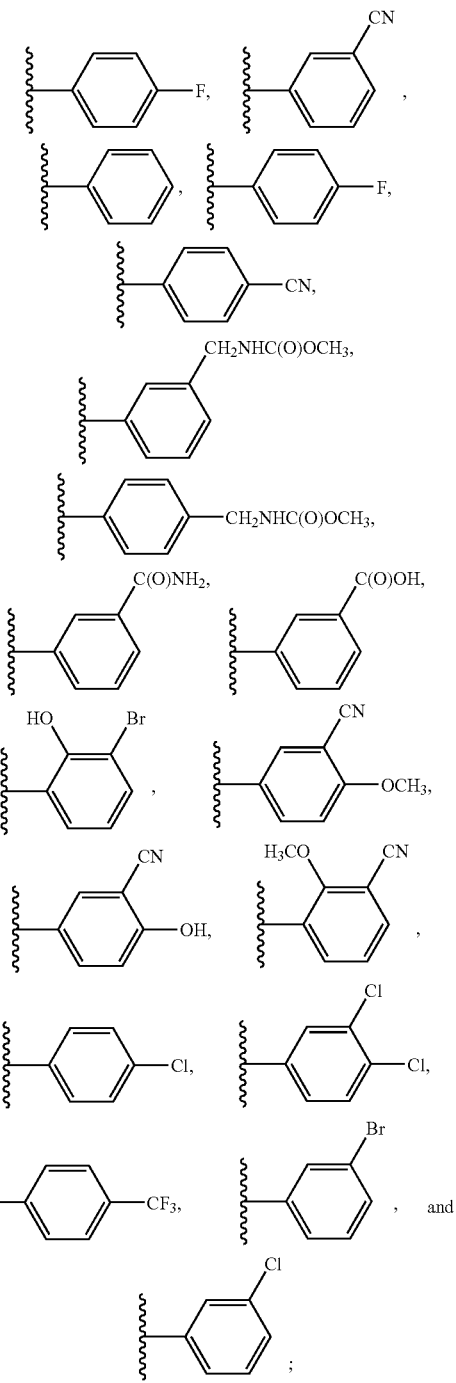
D is selected from the group consisting of
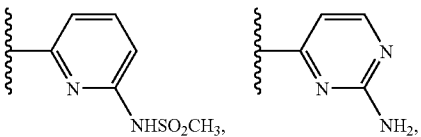
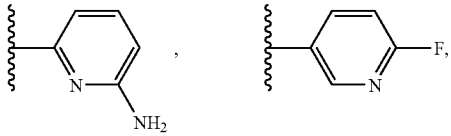
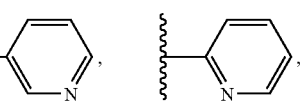
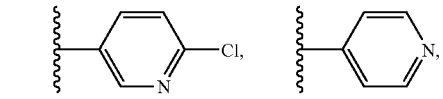
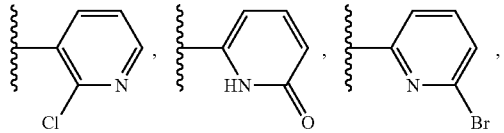
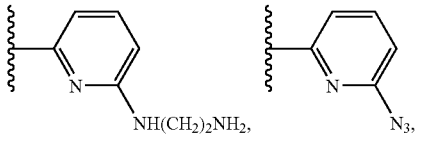
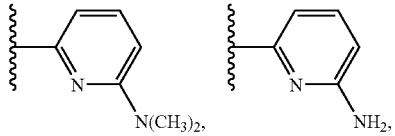
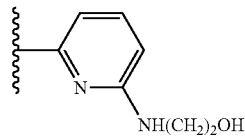
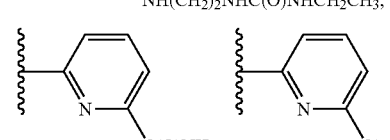
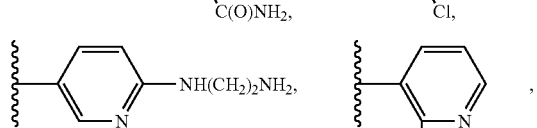
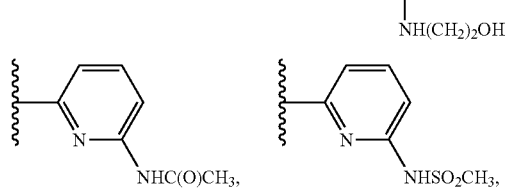

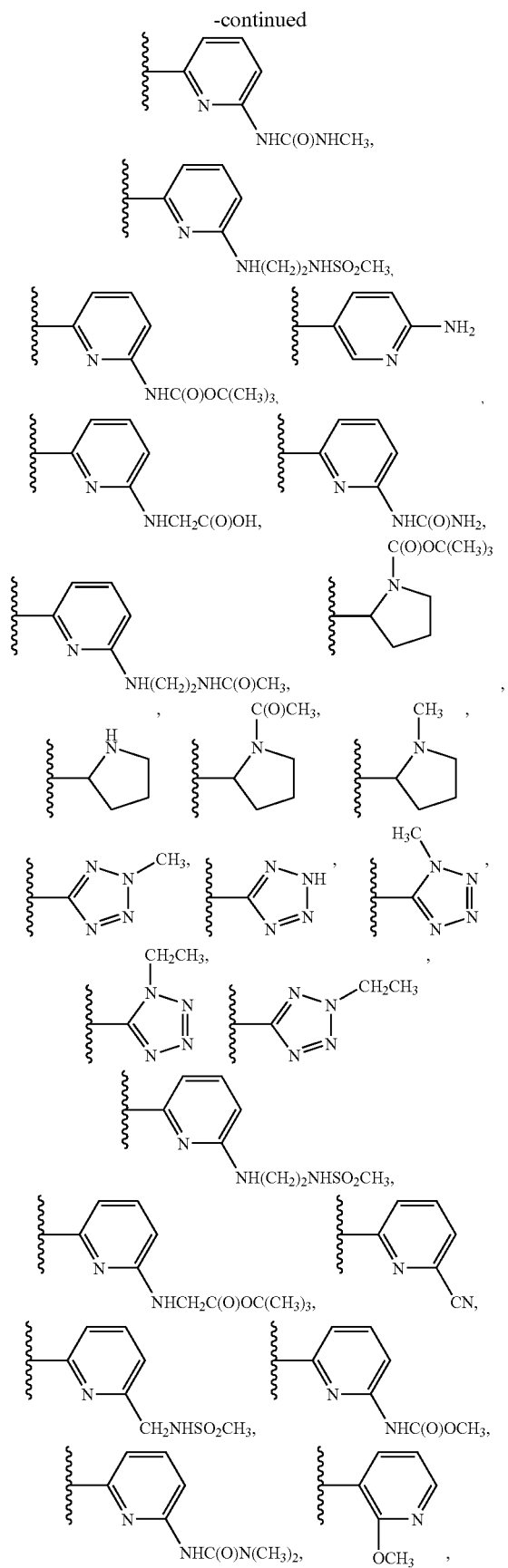
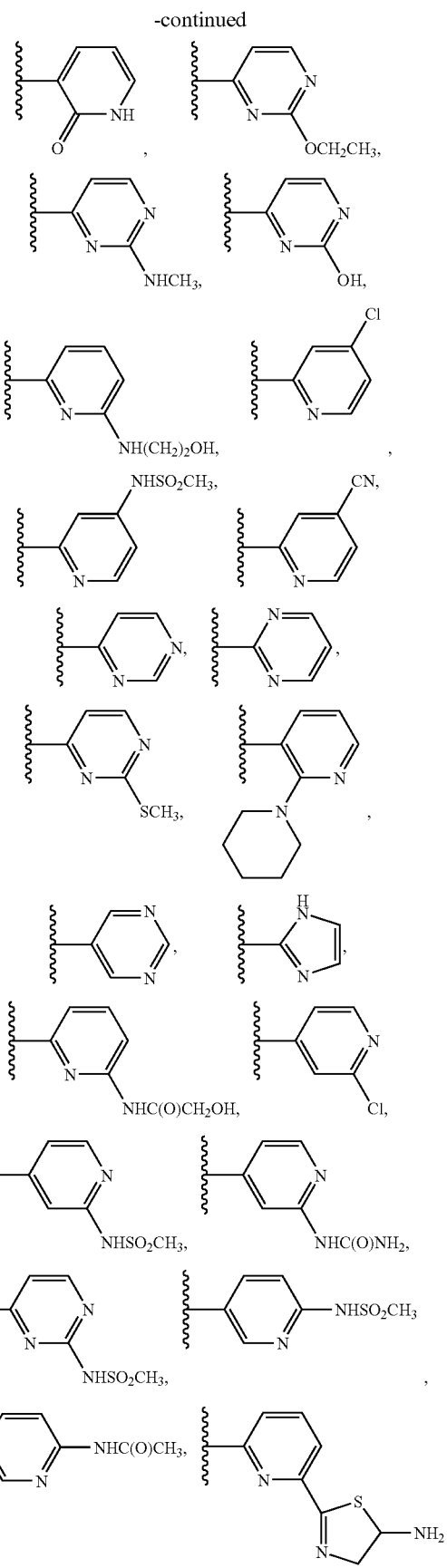

-continued

-continued

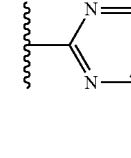 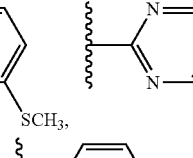

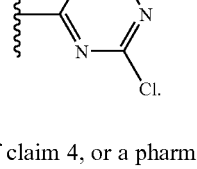

5. A compound of claim 4, or a pharmaceutically acceptable salt thereof, selected from the group consisting of
(R)-N-{6-[1-(4-fluorophenyl)-2,2-dipyridin-3-ylethyl]pyridin-2-yl}methanesulfonamide,
(S)-N-{6-[1-(4-fluorophenyl)-2,2-dipyridin-3-ylethyl]pyridin-2-yl}methanesulfonamide,
(R)-N-{6-[1-(3-cyanophenyl)-2,2-dipyridin-3-ylethyl]pyridin-2-yl}methanesulfonamide,
(S)-N-{6-[1-(3-cyanophenyl)-2,2-dipyridin-3-ylethyl]pyridin-2-yl}methanesulfonamide,
(±)-2-fluoro-5-[1-(4-fluorophenyl)-2,2-dipyridin-3-ylethyl]pyridine,
(±)-3-[1-(4-fluorophenyl)-2,2-dipyridin-3-ylethyl]pyridine,
(±)-2-[1-(4-fluorophenyl)-2,2-dipyridin-3-ylethyl]pyridine,
(±)-3-[2-(4-fluorophenyl)-1-pyridin-3-yl-2-pyridin-4-ylethyl]pyridine,
(±)-2-chloro-3-[2-(4-fluorophenyl)-2-pyridin-2-yl-1-pyridin-3-ylethyl]pyridine,
(±)-2-chloro-3-[2-(4-fluorophenyl)-2-pyridin-2-yl-1-pyridin-3-ylethyl]pyridine,
(±)-2-chloro-3-[1-(4-fluorophenyl)-2,2-dipyridin-3-ylethyl]pyridine,
(±)-2-fluoro-5-[2-(4-fluorophenyl)-2-pyridin-2-yl-1-pyridin-3-ylethyl]pyridine,
(±)-6-[1-(4-fluorophenyl)-2,2-dipyridin-3-ylethyl]-N,N-dimethylpyridin-2-amine,
(±)-6-[1-(4-fluorophenyl)-2,2-dipyridin-3-ylethyl]pyridin-2-amine,
(±)-2-({6-[1-(4-fluorophenyl)-2,2-dipyridin-3-ylethyl]pyridin-2-yl}amino)ethanol,
(±)-N-ethyl-N'-1[2-({6-[1-(4-fluorophenyl)-2,2-dipyridin-3-ylethyl]pyridin-2-yl}amino)ethyl]urea,
(±)-6-[1-(4-fluorophenyl)-2,2-dipyridin-3-ylethyl]pyridine-2-carboxamide,
(±)-methyl 3-(1-pyridin-2-yl-2,2-dipyridin-3-ylethyl)benzylcarbamate,
(±)-methyl 4-(1-pyridin-2-yl-2,2-dipyridin-3-ylethyl)benzylcarbamate,
(±)-3-(1-pyridin-2-yl-2,2-dipyridin-3-ylethyl)benzamide,
(±)-3-(1-pyridin-2-yl-2,2-dipyridin-3-ylethyl)benzoic acid,
(±)-6-[1-(4-fluorophenyl)-2,2-dipyridin-3-ylethyl]pyridin-2-amine,
(±)-2-({3-[1-(4-fluorophenyl)-2,2-dipyridin-3-ylethyl]pyridin-2-yl}amino)ethanol,
(±)-N-{6-[1-(4-fluorophenyl)-2,2-dipyridin-3-ylethyl]pyridin-2-yl}acetamide,
(±)-N-{6-[1-(4-fluorophenyl)-2,2-dipyridin-3-ylethyl]pyridin-2-yl}methanesulfonamide,
(±)-N-[2-({6-[1-(4-fluorophenyl)-2,2-dipyridin-3-ylethyl]pyridin-2-yl}amino)ethyl]methanesulfonamide, (±)-5-[2-(4-fluorophenyl)-2-pyridin-2-yl-1-pyridin-3-yl-ethyl]pyridin-2-amine,
(±)-5-[1-(4-fluorophenyl)-2,2-dipyridin-3-ylethyl]pyridin-2-amine,
(±)-N-{6-[1-(4-fluorophenyl)-2,2-dipyridin-3-ylethyl]pyridin-2-yl}glycine,
(±)-N-{6-[1-(3-cyanophenyl)-2,2-dipyridin-3-ylethyl]pyridin-2-yl}urea,
(±)-N-{6-[1-(3-cyanophenyl)-2,2-dipyridin-3-ylethyl]pyridin-2-yl}acetamide,
(±)-N-[2-({6-[1-(3-cyanophenyl)-2,2-dipyridin-3-ylethyl]pyridin-2-yl}amino)ethyl]acetamide,
(±)-N-[2-({6-[1-(3-cyanophenyl)-2,2-dipyridin-3-ylethyl]pyridin-2-yl}amino)ethyl]methanesulfonamide,
(±)-N-{6-[1(4-cyanophenyl)-2,2-dipyridin-3-ylethyl]pyridin-2-yl}-N'-methylurea,
(±)-tert-butyl N-{6-[1-(3-cyanophenyl)-2,2-dipyridin-3-ylethyl]pyridin-2-yl}glycinate,
(±)-N-{6-[2-(3-cyanophenyl)-2-pyridin-2-yl-1-pyridin-3-ylethyl]pyridin-2-yl}acetamide,
(±)-N-{6-[2-(3-cyanophenyl)-2-pyridin-2-yl-1-pyridin-3-ylethyl]pyridin-2-yl}methanesulfonamide,
(±)-N-[6-(2-phenyl-2-pyridin-2-yl-1-pyridin-3-ylethyl)pyridin-2-yl]methanesulfonamide,
(±)-N-[6-(2-phenyl-1,2-dipyridin-3-ylethyl)pyridin-2-yl]methanesulfonamide,
(±)-N-{6-[1-(4-fluorophenyl)-2,2-dipyridin-3-ylethyl]pyridin-2-yl}urea,
(±)-6-(2-phenyl-1,2-dipyridin-3-ylethyl)pyridin-2(1H)-one,
(±)-1-phenyl-2,2-dipyridin-3-yl-1-pyrimidin-2-ylethanol,
(±)-tert-Butyl 2-(2-hydroxy-1-phenyl-2,2-dipyridin-3-ylethyl)pyrrolidine-1-carboxylate,
(±)-methyl 6-[1-(4-fluorophenyl)-2,2-bis(2-fluoropyridin-3-yl)ethyl]pyridin-2-ylcarbamate,
(±)-N-{6-[1-(4-fluorophenyl)-2,2-bis(2-fluoropyridin-3-yl)ethyl]pyridin-2-yl}methanesulfonamide,
(±)-N-{6-[1-(4-fluorophenyl)-2,2-bis(2-fluoropyridin-3-yl)ethyl]pyridin-2-yl}urea,
(±)-methyl 6-[1-(4-fluorophenyl)-2,2-bis(5-methoxypyridin-3-yl)ethyl]pyridin-2-ylcarbarnate,
(±)-N-{6-[2,2-bis(6-chloropyridin-3-yl)-1-(4-fluorophenyl)ethyl]pyridin-2-yl}methanesulfonamide,
(±)-N-{6-[2,2-bis(6-aminopyridin-3-yl)-1-(4-fluorophenyl)ethyl]pyridin-2-yl}methanesulfonamide,
3-[1-(4-fluorophenyl)-2,2-dipyridin-3-ylethyl]-2-piperidin-1-ylpyridine,
N-{4-[1-(4-fluorophenyl)-2,2-dipyridin-3-ylethyl]pyrimidin-2-yl}methanesulfonamide,
N-{5-[1-(4-fluorophenyl)-2,2-dipyridin-3-ylethyl]pyridin-2-yl}methanesulfonamide,
N-{5-[1-(4-fluorophenyl)-2,2-dipyridin-3-ylethyl]pyridin-2-yl}acetamide,
5-{6-[1-(4-fluorophenyl)-2,2-dipyridin-3-ylethyl]pyridin-2-yl}-1,3,4-thiadiazol-2-amine,
6-[1-(4-fluorophenyl)-2,2-dipyridin-3-ylethyl]-N-pyridin-3-ylpyridin-2-amine,
4-[2-(6-aminopyridin-2-yl)-1-(4-chlorophenyl)-2-pyridin-3-ylethyl]pyrimidin-2-amine,
4-[1,2,2-tris(6-aminopyridin-2-yl)ethyl]fluorobenzene,
N-{6-[1-(4-fluorophenyl)-2,2-bis(6-methoxypyridin-3-yl)ethyl]pyridin-2-yl}methanesulfonamide,
(±)-6-[1-(4-fluorophenyl)-2-(6-aminopyridin-3-yl)-2-(6-methoxypyridin-2-ylethyl]pyridin-2-amine,
N~2~-{4-[1-(3-cyanophenyl)-2,2-dipyridin-3-ylethyl]pyrimidin-2-yl}-N1,N1-dimethylglycinamide,
N-{6-[1-(4-fluorophenyl)-2-(2-fluoropyridin-3-yl)-2-pyridin-3-ylethyl]pyridin-2-yl}methanesulfonamide,
N-{6-[1-(4-fluorophenyl)-2-(2-fluoropyridin-3-yl)-2-pyridin-3-ylethyl]pyridin-2-yl}methanesulfonamide,
methyl 6-[1-(4-fluorophenyl)-2-(2-fluoropyridin-3-yl)-2-pyridin-3-ylethyl]pyridin-2-ylcarbamate,
methyl 6-[1-(4-fluorophenyl)-2-(2-fluoropyridin-3-yl)-2-pyridin-3-ylethyl]pyridin-2-ylcarbarnate,
N-{6-[1-(3,4-dichlorophenyl)-2,2-dipyridin-3-ylethyl]pyridin-2-yl}methanesulfonamide,
N-{6-[1-(4-chlorophenyl)-2,2-dipyridin-3-ylethyl]pyridin-2-yl}methanesulfonamide,
N-(6-{2,2-dipyridin-3-yl-1-[4-(trifluoromethyl)phenyl]ethyl}pyridin-2-yl)methanesulfonamide,
4-[1-(4-chlorophenyl)-2,2-dipyridin-3-ylethyl]pyrimidin-2-amine,
N-{6-[1-(4-chlorophenyl)-2-(2-fluoropyridin-3-yl)-2-pyridin-3-ylethyl]pyridin-2-yl}methanesulfonamide,
4-[1-(4-chlorophenyl)-2,2-dipyridin-3-ylethyl]-n-methylpyrimidin-2-amine,
N-{6-[1-(4-cyanophenyl)-2-(2-fluoropyridin-3-yl)-2-pyridin-3-ylethyl]pyridin-2-yl}methanesulfonamide,
N-{6-[1-(4-cyanophenyl)-2-(2-fluoropyridin-3-yl)-2-pyridin-3-ylethyl]pyridin-2-yl}methanesulfonamide,
4-[1-(3,4-dichlorophenyl)-2,2-dipyridin-3-ylethyl]pyrimidin-2-amine,
4-{2,2-dipyridin-3-yl-1-[4-(trifluoromethyl)phenyl]ethyl}pyrimidin-2-amine,
methyl 6-[1-(2-aminopyrimidin-4-yl)-2-(4-chlorophenyl)-2-pyridin-3-ylethyl]pyridin-2-ylcarbamate,
N-{2-[1-(4-fluorophenyl)-2,2-dipyridin-3-ylethyl]pyrimidin-4-yl}methanesulfonamide,
N-{4-[1-(3-bromophenyl)-2,2-dipyridin-3-ylethyl]pyrimidin-2-yl}methanesulfonamide,
2-[1-(3-chlorophenyl)-2,2-dipyridin-3-ylethyl]-4-(methylthio)pyrimidine, and
2-[1-(3-chlorophenyl)-2,2-dipyridin-3-ylethyl]pyrimidin-4-amine.

6. A compound of claim 5, or a pharmaceutically acceptable salt thereof, selected from the group consisting of
(R)-N-{6-[1-(4-fluorophenyl)-2,2-dipyridin-3-ylethyl]pyridin-2-yl}methanesulfonamide,
(S)-N-{6-[1-(4-fluorophenyl)-2,2-dipyridin-3-ylethyl]pyridin-2-yl}methanesulfonamide,
(R)-N-{6-[1-(3-cyanophenyl)-2,2-dipyridin-3-ylethyl]pyridin-2-yl}methanesulfonamide, and
(S)-N-{6-[1-(3-cyanophenyl)-2,2-dipyridin-3-ylethyl]pyridin-2-yl}methanesulfonamide.

7. A compound or a pharmaceutically acceptable salt thereof, which is

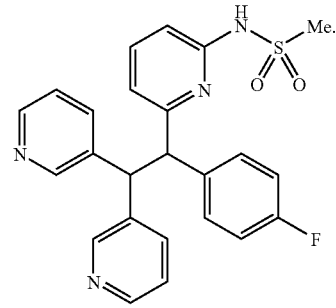

8. A method of treating a condition in a mammal, the treatment of which is effected or facilitated by K$_v$1.5 inhibition, which comprises administering a compound of claim 1 in an amount that is effective at inhibiting $K_v1.5$ wherein the condition is cardiac arrythmia and atrial ffibrillation.

9. A method of claim 8, wherein the condition is cardiac arrythmia.

10. A method of claim 9, wherein the cardiac arrythmia is atrial fibrillation.

11. A method of treating cardiac arrythmia comprising administering a compound of claim 1 with a compound selected from one of the classes of compounds consisting of antiaffhythmic agents having Kv1.5 blocking activities, ACE inhibitors, angiotensin II antagonists, cardiac glycosides, L-type calcium channel blockers, T-type calcium channel blockers, selective and nonselective beta blockers, endothelin antagonists, thrombin inhibitors, aspirin, nonselective NSAIDs, warfarin, factor Xa inhibitors, low molecular weight heparin, unfractionated heparin, clopidogrel, ticlopidine, IIb/IIIa receptor antagonists, 5HT receptor antagonists, integrin receptor antagonists, thromboxane receptor antagonists, TAFI inhibitors and P2T receptor antagonists.

12. A pharmaceutical formulation comprising a pharmaceutically acceptable carrier and the compound claim 1 or a pharmaceutically acceptable crystal form or hydrate thereof.

13. A pharmaceutical formulation comprising a pharmaceutically acceptable carrier and the compound claim 1 or a pharmaceutically acceptable crystal form orhydrate thereof.

* * * * *